United States Patent
Darlak et al.

(10) Patent No.: US 9,604,919 B2
(45) Date of Patent: Mar. 28, 2017

(54) DISUBSTITUTED AMINO ACIDS AND METHODS OF PREPARATION AND USE THEREOF

(71) Applicant: Aileron Therapeutics, Inc., Cambridge, MA (US)

(72) Inventors: Krzysztof Darlak, Newton, MA (US); Noriyuki Kawahata, West Roxbury, MA (US); Sameer Ahmed Athamneh, Corvallis, OR (US)

(73) Assignee: AILERON THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/070,306

(22) Filed: Nov. 1, 2013

(65) Prior Publication Data
US 2014/0128581 A1    May 8, 2014

Related U.S. Application Data

(60) Provisional application No. 61/721,457, filed on Nov. 1, 2012, provisional application No. 61/799,917, filed on Mar. 15, 2013.

(51) Int. Cl.
| | | |
|---|---|---|
| C07C 271/34 | (2006.01) | |
| C07C 269/08 | (2006.01) | |
| C07K 1/00 | (2006.01) | |
| C07C 271/22 | (2006.01) | |

(52) U.S. Cl.
CPC .......... *C07C 271/34* (2013.01); *C07C 269/08* (2013.01); *C07C 271/22* (2013.01); *C07K 1/006* (2013.01); *C07B 2200/07* (2013.01); *C07C 2103/18* (2013.01)

(58) Field of Classification Search
None
See application file for complete search history.

(56) References Cited

U.S. PATENT DOCUMENTS

| | | |
|---|---|---|
| 4,000,259 A | 12/1976 | Garsky |
| 4,191,754 A | 3/1980 | Nutt et al. |
| 4,438,270 A | 3/1984 | Bey et al. |
| 5,120,859 A | 6/1992 | Webb |
| 5,245,009 A | 9/1993 | Kornreich et al. |
| 5,310,910 A | 5/1994 | Drtina et al. |

(Continued)

FOREIGN PATENT DOCUMENTS

| | | |
|---|---|---|
| CN | 1252808 A | 5/2000 |
| CN | 1583730 A | 2/2005 |

(Continued)

OTHER PUBLICATIONS

"Purification of Laboratory Chemicals" fifth edition, 2003, Armarego et al.*

(Continued)

*Primary Examiner* — Clinton Brooks
(74) *Attorney, Agent, or Firm* — Wilson Sonsini Goodrich & Rosati

(57) ABSTRACT

Provided are crystalline α, α-disubstituted amino acids and their crystalline salts containing a terminal alkene on one of their side chains, as well as optionally crystalline halogenated and deuterated analogs of the α, α-disubstituted amino acids and their salts; methods of making these, and methods of using these.

26 Claims, 9 Drawing Sheets

(56) References Cited

U.S. PATENT DOCUMENTS

| | | |
|---|---|---|
| 5,364,851 A | 11/1994 | Joran |
| 5,446,128 A | 8/1995 | Kahn |
| 5,650,133 A | 7/1997 | Carvalho et al. |
| 5,672,584 A | 9/1997 | Borchardt et al. |
| 5,702,908 A | 12/1997 | Picksley et al. |
| 5,708,136 A | 1/1998 | Burrell et al. |
| 5,731,408 A | 3/1998 | Hadley et al. |
| 5,756,669 A | 5/1998 | Bischoff et al. |
| 5,770,377 A | 6/1998 | Picksley et al. |
| 5,811,515 A | 9/1998 | Grubbs et al. |
| 5,817,752 A | 10/1998 | Yu |
| 5,824,483 A | 10/1998 | Houston, Jr. et al. |
| 5,840,833 A | 11/1998 | Kahn |
| 5,859,184 A | 1/1999 | Kahn et al. |
| 5,893,397 A | 4/1999 | Peterson et al. |
| 6,030,997 A | 2/2000 | Eilat et al. |
| 6,031,073 A | 2/2000 | Yu |
| 6,043,339 A | 3/2000 | Lin et al. |
| 6,046,289 A | 4/2000 | Komazawa et al. |
| 6,051,554 A | 4/2000 | Hornik et al. |
| 6,054,556 A | 4/2000 | Huby et al. |
| 6,118,010 A | 9/2000 | Ueda et al. |
| 6,169,073 B1 | 1/2001 | Halazonetis et al. |
| 6,177,076 B1 | 1/2001 | Lattime et al. |
| 6,177,542 B1 | 1/2001 | Ruoslahti et al. |
| 6,184,344 B1 | 2/2001 | Kent et al. |
| 6,204,361 B1 | 3/2001 | Carpino et al. |
| 6,245,886 B1 | 6/2001 | Halazonetis et al. |
| 6,287,787 B1 | 9/2001 | Houghten et al. |
| 6,348,558 B1 | 2/2002 | Harris et al. |
| 6,420,118 B1 | 7/2002 | Halazonetis et al. |
| 6,420,136 B1 | 7/2002 | Riabowol et al. |
| 6,495,674 B1 | 12/2002 | Lemke et al. |
| 6,569,993 B1 | 5/2003 | Sledeski et al. |
| 6,610,657 B1 | 8/2003 | Goueli |
| 6,686,148 B1 | 2/2004 | Shen et al. |
| 6,784,157 B2 | 8/2004 | Halazonetis et al. |
| 6,875,594 B2 | 4/2005 | Muir et al. |
| 7,083,983 B2 | 8/2006 | Lane et al. |
| 7,115,372 B2 | 10/2006 | Shen et al. |
| 7,183,059 B2 | 2/2007 | Verdine et al. |
| 7,189,801 B2 | 3/2007 | Halazonetis et al. |
| 7,192,713 B1 | 3/2007 | Verdine et al. |
| 7,202,332 B2 | 4/2007 | Arora et al. |
| 7,666,983 B2 | 2/2010 | Halazonetis et al. |
| 7,705,118 B2 | 4/2010 | Arora et al. |
| 7,723,469 B2 | 5/2010 | Walensky et al. |
| 7,737,174 B2 | 6/2010 | Wang et al. |
| 7,759,383 B2 | 7/2010 | Wang et al. |
| 7,786,072 B2 * | 8/2010 | Verdine et al. ............... 514/21.4 |
| 7,884,107 B2 | 2/2011 | Ma et al. |
| 7,893,278 B2 | 2/2011 | Haley et al. |
| 7,927,813 B2 | 4/2011 | Geneste et al. |
| 7,932,397 B2 | 4/2011 | Hock et al. |
| 7,960,506 B2 | 6/2011 | Nash |
| 7,964,724 B2 | 6/2011 | Fotouhi et al. |
| 7,981,998 B2 | 7/2011 | Nash |
| 7,981,999 B2 | 7/2011 | Nash |
| 8,017,607 B2 | 9/2011 | Bartkovitz et al. |
| 8,058,269 B2 | 11/2011 | Chen et al. |
| 8,071,541 B2 | 12/2011 | Arora et al. |
| 8,076,482 B2 | 12/2011 | Chen et al. |
| 8,088,815 B2 | 1/2012 | Bartkovitz et al. |
| 8,088,931 B2 | 1/2012 | Wang et al. |
| 8,124,726 B2 | 2/2012 | Robinson et al. |
| 8,198,405 B2 | 6/2012 | Walensky et al. |
| 8,217,051 B2 | 7/2012 | Zhang et al. |
| 8,324,428 B2 | 12/2012 | Verdine et al. |
| 8,343,760 B2 | 1/2013 | Lu et al. |
| 8,389,484 B2 | 3/2013 | Shen et al. |
| 8,399,405 B2 | 3/2013 | Nash et al. |
| 8,524,653 B2 | 9/2013 | Nash et al. |
| 8,592,377 B2 | 11/2013 | Verdine et al. |
| 8,609,809 B2 | 12/2013 | Nash |
| 8,637,686 B2 | 1/2014 | Nash |
| 8,796,418 B2 | 8/2014 | Walensky et al. |
| 8,808,694 B2 | 8/2014 | Nash et al. |
| 8,859,723 B2 | 10/2014 | Guerlavais et al. |
| 8,871,899 B2 | 10/2014 | Wang et al. |
| 8,889,632 B2 | 11/2014 | Bernal et al. |
| 8,895,699 B2 | 11/2014 | Verdine et al. |
| 8,927,500 B2 | 1/2015 | Guerlavais et al. |
| 8,987,414 B2 | 3/2015 | Guerlavais et al. |
| 9,023,988 B2 | 5/2015 | Nash |
| 2002/0098580 A1 | 7/2002 | Nandabalan et al. |
| 2002/0132977 A1 | 9/2002 | Yuan et al. |
| 2003/0027766 A1 | 2/2003 | Ioannides et al. |
| 2003/0060432 A1 | 3/2003 | Tocque et al. |
| 2003/0144331 A1 | 7/2003 | Gudkov et al. |
| 2003/0166138 A1 | 9/2003 | Kinsella et al. |
| 2003/0176318 A1 | 9/2003 | Gudkov et al. |
| 2004/0106159 A1 | 6/2004 | Kern et al. |
| 2004/0106548 A1 | 6/2004 | Schmidt et al. |
| 2004/0115135 A1 | 6/2004 | Quay |
| 2004/0146971 A1 | 7/2004 | Lane et al. |
| 2004/0152708 A1 | 8/2004 | Li et al. |
| 2004/0170653 A1 | 9/2004 | Stanislawski et al. |
| 2004/0170971 A1 | 9/2004 | Kinzler et al. |
| 2004/0228866 A1 | 11/2004 | Lu |
| 2004/0235746 A1 | 11/2004 | Hawiger et al. |
| 2004/0248198 A1 | 12/2004 | Kriwacki et al. |
| 2004/0265931 A1 | 12/2004 | Gu et al. |
| 2005/0013820 A1 | 1/2005 | Holoshitz et al. |
| 2005/0037383 A1 | 2/2005 | Taremi et al. |
| 2005/0089511 A1 | 4/2005 | Roth et al. |
| 2005/0119167 A1 | 6/2005 | Abbenante et al. |
| 2005/0137137 A1 | 6/2005 | Lane et al. |
| 2005/0176075 A1 | 8/2005 | Jones et al. |
| 2005/0222224 A1 | 10/2005 | Gudkov et al. |
| 2005/0222427 A1 | 10/2005 | Sharpless et al. |
| 2005/0227932 A1 | 10/2005 | Lu et al. |
| 2005/0245764 A1 | 11/2005 | Yamashita et al. |
| 2005/0277764 A1 | 12/2005 | Boyd et al. |
| 2006/0008848 A1 | 1/2006 | Verdine et al. |
| 2006/0073518 A1 | 4/2006 | Timmerman et al. |
| 2006/0100143 A1 | 5/2006 | Lu et al. |
| 2006/0111411 A1 | 5/2006 | Cooper et al. |
| 2006/0149039 A1 | 7/2006 | Hunter et al. |
| 2006/0189511 A1 | 8/2006 | Koblish et al. |
| 2006/0233779 A1 | 10/2006 | Ben-Avraham et al. |
| 2006/0293380 A1 | 12/2006 | Nantermet et al. |
| 2007/0006332 A1 | 1/2007 | O'Neill |
| 2007/0020620 A1 | 1/2007 | Finn et al. |
| 2007/0032417 A1 | 2/2007 | Baell |
| 2007/0129324 A1 | 6/2007 | Boyd et al. |
| 2007/0274915 A1 | 11/2007 | Rao et al. |
| 2008/0081038 A1 | 4/2008 | Cho et al. |
| 2008/0085279 A1 | 4/2008 | Boyd et al. |
| 2008/0132485 A1 | 6/2008 | Wang et al. |
| 2008/0161426 A1 | 7/2008 | Gudkov et al. |
| 2008/0213175 A1 | 9/2008 | Kolb et al. |
| 2008/0242598 A1 | 10/2008 | Fairlie et al. |
| 2008/0305490 A1 | 12/2008 | Burrell et al. |
| 2008/0311608 A1 | 12/2008 | Tocque et al. |
| 2009/0275519 A1 | 11/2009 | Nash et al. |
| 2009/0311174 A1 | 12/2009 | Allen |
| 2009/0326192 A1 | 12/2009 | Nash et al. |
| 2010/0010065 A1 | 1/2010 | Smith |
| 2010/0081611 A1 | 4/2010 | Bradner et al. |
| 2010/0093057 A1 | 4/2010 | Beattie et al. |
| 2010/0093086 A1 | 4/2010 | Lin et al. |
| 2010/0210515 A1 | 8/2010 | Nash et al. |
| 2010/0273704 A1 | 10/2010 | Korsmeyer et al. |
| 2010/0286362 A1 | 11/2010 | Boyd et al. |
| 2010/0298201 A1 | 11/2010 | Nash et al. |
| 2011/0021529 A1 | 1/2011 | Lain et al. |
| 2011/0046043 A1 | 2/2011 | Wang et al. |
| 2011/0065915 A1 | 3/2011 | Malcolmson et al. |
| 2011/0144303 A1 | 6/2011 | Nash et al. |
| 2011/0144306 A1 | 6/2011 | Verdine et al. |
| 2011/0183917 A1 | 7/2011 | Lu et al. |
| 2011/0218155 A1 | 9/2011 | Walensky et al. |
| 2011/0223149 A1 | 9/2011 | Nash et al. |
| 2011/0245175 A1 | 10/2011 | Arora et al. |

(56) References Cited

U.S. PATENT DOCUMENTS

| | | |
|---|---|---|
| 2011/0245477 A1 | 10/2011 | Hoveyda et al. |
| 2011/0250685 A1 | 10/2011 | Nash |
| 2011/0251252 A1 | 10/2011 | Wang et al. |
| 2011/0313167 A1 | 12/2011 | Doemling |
| 2012/0040889 A1 | 2/2012 | Nash et al. |
| 2012/0082636 A1 | 4/2012 | Walensky et al. |
| 2012/0101047 A1 | 4/2012 | Nash et al. |
| 2012/0115783 A1 | 5/2012 | Nash et al. |
| 2012/0115793 A1 | 5/2012 | Nash et al. |
| 2012/0156197 A1 | 6/2012 | Errico et al. |
| 2012/0178700 A1 | 7/2012 | Nash et al. |
| 2012/0238507 A1 | 9/2012 | Fairlie et al. |
| 2012/0264674 A1 | 10/2012 | Nash et al. |
| 2012/0264738 A1 | 10/2012 | Sugimoto et al. |
| 2012/0270800 A1 | 10/2012 | Verdine et al. |
| 2012/0283269 A1 | 11/2012 | Blagosklonny et al. |
| 2012/0328692 A1 | 12/2012 | Lu et al. |
| 2013/0005943 A1 | 1/2013 | Arora et al. |
| 2013/0023646 A1 | 1/2013 | Nash et al. |
| 2013/0072439 A1 | 3/2013 | Nash et al. |
| 2013/0123169 A1 | 5/2013 | Kawahata et al. |
| 2013/0123196 A1 | 5/2013 | Arora et al. |
| 2013/0210743 A1 | 8/2013 | Guerlavais et al. |
| 2013/0274205 A1 | 10/2013 | Guerlavais et al. |
| 2013/0330421 A1 | 12/2013 | Marine |
| 2014/0011979 A1 | 1/2014 | Verdine et al. |
| 2014/0018302 A1 | 1/2014 | Walensky et al. |
| 2014/0051828 A1 | 2/2014 | Arora et al. |
| 2014/0135255 A1 | 5/2014 | Nash et al. |
| 2014/0135473 A1 | 5/2014 | Nash |
| 2014/0162339 A1 | 6/2014 | Verdine et al. |
| 2014/0235549 A1 | 8/2014 | Moellering et al. |
| 2014/0256912 A1 | 9/2014 | Moellering et al. |
| 2014/0296160 A1 | 10/2014 | Walensky et al. |
| 2014/0323701 A1 | 10/2014 | Nash et al. |
| 2014/0378390 A1 | 12/2014 | Guerlavais et al. |
| 2015/0038430 A1 | 2/2015 | Nash et al. |
| 2015/0051155 A1 | 2/2015 | Guerlavais et al. |
| 2015/0183825 A1 | 7/2015 | Guerlavais et al. |

FOREIGN PATENT DOCUMENTS

| | | |
|---|---|---|
| CZ | 9700369 A3 | 9/1998 |
| EP | 0467699 A2 | 1/1992 |
| EP | 0467699 A3 | 2/1993 |
| EP | 0528312 A2 | 2/1993 |
| EP | 0552417 A1 | 7/1993 |
| EP | 0729972 A1 | 9/1996 |
| EP | 0643726 B1 | 8/1999 |
| EP | 0977580 B1 | 4/2003 |
| EP | 1321474 A1 | 6/2003 |
| EP | 1452868 A2 | 9/2004 |
| EP | 1541692 A1 | 6/2005 |
| EP | 1602663 A1 | 12/2005 |
| EP | 1609802 A1 | 12/2005 |
| EP | 1243923 B1 | 3/2006 |
| EP | 1180016 B1 | 9/2006 |
| EP | 0958305 B1 | 6/2008 |
| EP | 1597585 B1 | 6/2011 |
| EP | 2377849 A2 | 10/2011 |
| JP | 2002524391 A | 8/2002 |
| JP | 2010120881 A | 6/2010 |
| WO | WO-8909233 A1 | 10/1989 |
| WO | WO-9206998 A1 | 4/1992 |
| WO | WO-9301203 A1 | 1/1993 |
| WO | WO-9307170 A1 | 4/1993 |
| WO | WO-9422910 A1 | 10/1994 |
| WO | WO-9425482 A1 | 11/1994 |
| WO | WO-9500534 A1 | 1/1995 |
| WO | WO-9522546 A1 | 8/1995 |
| WO | WO-9628449 A1 | 9/1996 |
| WO | WO-9634878 A1 | 11/1996 |
| WO | WO-9700267 A1 | 1/1997 |
| WO | WO-9714794 A1 | 4/1997 |
| WO | WO-9730072 A1 | 8/1997 |
| WO | WO-9801467 A2 | 1/1998 |
| WO | WO-9817625 A1 | 4/1998 |
| WO | WO-9846631 A | 10/1998 |
| WO | WO-9963929 A2 | 12/1999 |
| WO | WO-02070547 A1 | 9/2002 |
| WO | WO-02072597 A2 | 9/2002 |
| WO | WO-03054000 A1 | 7/2003 |
| WO | WO-03059933 A2 | 7/2003 |
| WO | WO-03070892 A2 | 8/2003 |
| WO | WO-03102538 A2 | 12/2003 |
| WO | WO-03106491 A2 | 12/2003 |
| WO | WO-03059933 A3 | 1/2004 |
| WO | WO-2004077062 A2 | 9/2004 |
| WO | WO-03070892 A3 | 11/2004 |
| WO | WO-2004077062 A3 | 1/2005 |
| WO | WO-2005007675 A2 | 1/2005 |
| WO | WO-2004077062 B1 | 2/2005 |
| WO | WO-2005012335 A1 | 2/2005 |
| WO | WO-2005044839 A2 | 5/2005 |
| WO | WO-2005007675 A3 | 7/2005 |
| WO | WO-2005044839 A3 | 7/2005 |
| WO | WO-2005074521 A2 | 8/2005 |
| WO | WO-2005118620 A2 | 12/2005 |
| WO | WO-2005118634 A2 | 12/2005 |
| WO | WO-2005118634 A3 | 5/2006 |
| WO | WO-2005118620 A3 | 6/2006 |
| WO | WO-2006078161 A1 | 7/2006 |
| WO | WO-2008014216 A1 | 1/2008 |
| WO | WO-2008045238 A2 | 4/2008 |
| WO | WO-2008061192 A2 | 5/2008 |
| WO | WO-2008076904 A1 | 6/2008 |
| WO | WO-2007141533 A3 | 7/2008 |
| WO | WO-2008061192 A3 | 7/2008 |
| WO | WO-2008092281 A1 | 8/2008 |
| WO | WO-2008095063 A1 | 8/2008 |
| WO | WO-2008104000 A2 | 8/2008 |
| WO | WO-2008106507 A2 | 9/2008 |
| WO | WO-2008121767 A2 | 10/2008 |
| WO | WO-2008137633 A2 | 11/2008 |
| WO | WO-2008121767 A3 | 1/2009 |
| WO | WO-2009089004 A1 | 7/2009 |
| WO | WO-2009099677 A2 | 8/2009 |
| WO | WO-2009110952 A2 | 9/2009 |
| WO | WO-2009126292 A2 | 10/2009 |
| WO | WO-2009137532 A1 | 11/2009 |
| WO | WO-2009149214 A2 | 12/2009 |
| WO | WO-2009149339 A2 | 12/2009 |
| WO | WO-2010011313 A2 | 1/2010 |
| WO | WO-2010013011 A1 | 2/2010 |
| WO | WO-2010033879 A2 | 3/2010 |
| WO | WO-2010034026 A1 | 3/2010 |
| WO | WO-2010034028 A1 | 3/2010 |
| WO | WO-2010034029 A1 | 3/2010 |
| WO | WO-2010034031 A1 | 3/2010 |
| WO | WO-2010034032 A2 | 3/2010 |
| WO | WO-2010034034 A1 | 3/2010 |
| WO | WO-2010058819 A1 | 5/2010 |
| WO | WO-2010060112 A1 | 5/2010 |
| WO | WO-2010068684 A2 | 6/2010 |
| WO | WO-2010083347 A2 | 7/2010 |
| WO | WO-2010083501 A2 | 7/2010 |
| WO | WO-2010100351 A1 | 9/2010 |
| WO | WO-2010107485 A1 | 9/2010 |
| WO | WO-2010011313 A3 | 12/2010 |
| WO | WO-2011005219 A1 | 1/2011 |
| WO | WO-2011008260 A2 | 1/2011 |
| WO | WO-2011008260 A3 | 3/2011 |
| WO | WO-2011023677 A1 | 3/2011 |
| WO | WO-2011038049 A1 | 3/2011 |
| WO | WO-2011047215 A1 | 4/2011 |
| WO | WO-2011060049 A2 | 5/2011 |
| WO | WO-2011061139 A1 | 5/2011 |
| WO | WO-2011076786 A1 | 6/2011 |
| WO | WO-2011090297 A2 | 7/2011 |
| WO | WO-2011101297 A1 | 8/2011 |
| WO | WO-2011106650 A2 | 9/2011 |
| WO | WO-2011161699 A2 | 12/2011 |
| WO | WO-2012016186 A1 | 2/2012 |
| WO | WO-2012021874 A1 | 2/2012 |

(56) References Cited

FOREIGN PATENT DOCUMENTS

| | | |
|---|---|---|
| WO | WO-2012021875 A1 | 2/2012 |
| WO | WO-2012021876 A2 | 2/2012 |
| WO | WO-2012033525 A2 | 3/2012 |
| WO | WO-2012034954 A1 | 3/2012 |
| WO | WO-2012038307 A1 | 3/2012 |
| WO | WO-2012045018 A1 | 4/2012 |
| WO | WO-2012047587 A2 | 4/2012 |
| WO | WO-2012051405 A1 | 4/2012 |
| WO | WO-2012059696 A1 | 5/2012 |
| WO | WO-2012065022 A2 | 5/2012 |
| WO | WO-2012065181 A2 | 5/2012 |
| WO | WO-2012066095 A1 | 5/2012 |
| WO | WO-2012040459 A3 | 6/2012 |
| WO | WO-2012076513 A1 | 6/2012 |
| WO | WO-2012080376 A1 | 6/2012 |
| WO | WO-2012080389 A1 | 6/2012 |
| WO | WO-2012083078 A2 | 6/2012 |
| WO | WO-2012083181 A1 | 6/2012 |
| WO | WO-2012121057 A1 | 9/2012 |
| WO | WO-2012122059 A1 | 9/2012 |
| WO | WO-2012149563 A1 | 11/2012 |
| WO | WO-2012173846 A2 | 12/2012 |
| WO | WO-2012175962 A1 | 12/2012 |
| WO | WO-2013033645 A1 | 3/2013 |
| WO | WO-2013036208 A1 | 3/2013 |
| WO | WO-2013049250 A1 | 4/2013 |
| WO | WO-2013059525 A1 | 4/2013 |
| WO | WO-2013059530 A2 | 4/2013 |
| WO | WO-2013123266 A1 | 8/2013 |
| WO | WO-2013123267 A1 | 8/2013 |
| WO | WO-2014071241 A1 | 5/2014 |
| WO | WO-2014138429 A2 | 9/2014 |

OTHER PUBLICATIONS

Altschul et al., Basic local alignment search tool. J Mol Biol. Oct. 5, 1990;215(3):403-10.
Andrews et al. Forming Stable Helical Peptide Using Natural and Artificial Amino Acids. Tetrahedron. 1999;55:11711-11743.
Angell, et al. Peptidomimetics via copper-catalyzed azide-alkyne cycloadditions. Chem Soc Rev. Oct. 2007;36(10):1674-89.
Angell, et al. Ring closure to beta-turn mimics via copper-catalyzed azide/alkyne cycloadditions. J Org Chem. Nov. 11, 2005;70(23):9595-8.
Annis, et al. A general technique to rank protein-ligand binding affinities and determine allosteric versus direct binding site competition in compound mixtures. J Am Chem Soc. Dec. 1, 2004;126(47):15495-503.
Annis, et al. ALIS: An Affinity Selection-Mass Spectrometry System for the Discovery and Characterization of Protein-Ligand Interactions. In: Wanner, K. and Höfner, G. eds. Mass Spectrometry in Medicinal Chemistry. Wiley-VCH; 2007:121-156.
Armstrong et al., X=Y-ZH Systems as potential 1,3-dipoles. 5. Intramolecular cycloadditions of imines of a-amino acid esters. Tetrahedron. 1985;41(17):3547-58.
Arosio, et al. Click chemistry to functionalise peptidomimetics. Tetrahedron Letters. 2006; 47:3697-3700.
Austin et al., "A Template for Stabilization of a Peptide α-Helix: Synthesis and Evaluation of Conformational Effects by Circular Dichroism and NMR," J. Am. Chem. Soc. 119:6461-6472 (1997).
Baek, et al., Structure of the staples p53 peptide bound to Mdm2. J Am Chem Soc. Jan. 11, 2012; 134(1):103-6. doi: 10.1021/ja2090367. Epub Dec. 14, 2011.
Baell, J.B. Prospects for Targeting the Bcl-2 Family of Proteins to Develop Novel cytotoxic drugs. Biochem Pharmacol. Sep. 2002;64(5-6):851-63.
Bakhshi, et al. Cloning the chromosomal breakpoint of t(14;18) human lymphomas: clustering around JH on chromosome 14 and near a transcriptional unit on 18. Cell. Jul. 1985;41(3):899-906.
Banerji et al. Synthesis of Cyclic β-Turn Mimics from L-Pro-Phe/Phe-L-Pro Derived Di- and Tripeptides via Ring Closing Metathesis: The Role of Chirality of the Phe Residue During Cyclization. Tetrahedron Lett. 2002; 43:6473-6477.
Barandon et al., Reduction of infarct size and prevention of cardiac rupture in transgenic mice overexpressing FrzA. Circulation. Nov. 4, 2003;108(18):2282-9. Epub Oct. 27, 2003.
Barker, et al., Cyclic RGD peptide analogues as antiplatelet antithrombotics. J Med Chem. May 29, 1992;35(11):2040-8. (Abstract only).
Beloken et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon et al., Improved procedures for the synthesis of (S)-21N-(N'-benzyl-prolypaminolbenzophenone (BPB) and Ni(II) complexes of Schiff's bases derived from BPB and amino acids. Tetrahedron: Asymmetry. 1998;9:4249-52.
Belokon, Y. N., et al., "Halo-substituted (S)-N-(2-benzoylphenyl)-1-benzylpyrolidine-2 carboxamides as new chiral auxiliaries for the asymmetric synthesis of (S)-a-amino acids,"Russian Chemical Bulletin, International Edition, 51 (8): 1593-1599 (2002).
Berendsen et al., A glimpse of the Holy Grail? Science. Oct. 23, 1998;282(5389):642-3.
Bernal, et al. A stapled p53 helix overcomes HDMX-mediated suppression of p53. Cancer Cell. Nov. 16, 2010;18(5):411-22. doi: 10.1016/j.ccr.2010.10.024.
Blackwell, et al. Highly Efficient Synthesis of Covalently Cross-Linked Peptide Helices by Ring-Closing Metathesis. Angewandte Chemie International Edition.1998; 37(23):3281-3284.
Bock, et al. 1,2,3-Triazoles as peptide bond isosteres: synthesis and biological evaluation of cyclotetrapeptide mimics. Org Biomol Chem. Mar. 21, 2007;5(6):971-5.
Boguslavsky, et al. Effect of peptide conformation on membrane permeability. J Pept Res. Jun. 2003;61(6):287-97.
Bossy-Wetzel, et al. Assays for cytochrome c release from mitochondria during apoptosis. Methods Enzymol. 2000;322:235-42.
Bossy-Wetzel, et al. Detection of apoptosis by annexin V labeling. Methods Enzymol. 2000;322:15-8.
Bottger, et al. Molecular characterization of the hdm2-p53 interaction. J Mol Biol. Jun. 27, 1997;269(5):744-56.
Bracken et al. Synthesis and nuclear magnetic resonance structure determination of an alpha-helical, bicyclic, lactam-bridged hexapeptide. JACS. 1994;116:6431-6432.
Bradley et al., Limits of cooperativity in a structurally modular protein: response of the Notch ankyrin domain to analogous alanine substitutions in each repeat. J Mol Biol. Nov. 22, 2002;324(2):373-86.
Brown, et al. A spiroligomer α-helix mimic that binds HDM2, penetrates human cells and stabilizes HDM2 in cell culture. PLoS One. 2012;7(10):e45948. doi: 10.1371/journal.pone.0045948. Epub Oct. 18, 2012.
Brown, et al. Stapled peptides with improved potency and specificity that activate p53. ACS Chem Biol. Mar. 15, 2013;8(3):506-12. doi: 10.1021/cb3005148. Epub Dec. 18, 2012.
Brunel, et al. Synthesis of constrained helical peptides by thioether ligation: application to analogs of gp41. Chem Commun (Camb). May 28, 2005;(20):2552-4. Epub Mar. 11, 2005.
Burger et al., Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.
Burrage, et al. Biomimetic synthesis of Iantibiotics. Chemsitry. Apr. 14, 2000;6(8):1455-66.
Cabezas & Satterthwait, "The Hydrogen Bond Mimic Approach: Solid-phase Synthesis of a Peptide Stabilized as an α-Helix with a Hydrazone Link," J. Am. Chem. Soc. 121:3862-3875 (1999).
Cantel, et al. Synthesis and Conformational Analysis of a Cyclic Peptide Obtained via i to i+4 Intramolecular Side-Chain to Side-Chain Azide-Alkyne 1,3-Dipolar Cycloaddition. JOC Featured Article. Published on the web May 20, 2008.
Carillo et al., The Multiple Sequence Alignment Problem in Biology. SIAM J Applied Math. 1988;48:1073-82.
CAS Registry No. 2176-37-6. STN Entry Date Nov. 16, 1984.
CAS Registry No. 2408-85-7, STN Entry Date Nov. 16, 1984.

(56) References Cited

OTHER PUBLICATIONS

CAS Registry No. 4727-05-3, STN Entry Date Nov. 16, 1984.
CAS Registry No. 561321-72-0, STN Entry Date Aug. 6, 2003.
CAS Registry No. 721918-14-5, STN Entry Date Aug. 4, 2004.
Chakrabartty et al., "Helix Capping Propensities in Peptides Parallel Those in Proteins," Proc. Nat'l Acad. Sci. USA 90:11332-11336 (1993).
Chang, et al. Stapled α-helical peptide drug development: a potent dual inhibitor of MDM2 and MDMX for p53-dependent cancer therapy. Proc Natl Acad Sci U S A. Sep. 3, 2013;110(36):E3445-54. doi: 10.1073/pnas.1303002110. Epub Aug. 14, 2013.
Chapman et al., "A Highly Stable Short α-Helix Constrained by a Main-chain Hydrogen-bond Surrogate," J. Am. Chem. Soc. 126:12252-12253 (2004).
Chapman, et al. Optimized synthesis of hydrogen-bond surrogate helices: surprising effects of microwave heating on the activity of Grubbs catalysts. Org Lett. Dec. 7, 2006;8(25):5825-8.
Chin & Schepartz, "Design and Evolution of a Miniature Bcl-2 Binding Protein," Angew. Chem. Int. Ed. 40(20):3806-3809 (2001).
Chin et al., "Circular Dichroism Spectra of Short, Fixed-nucleus Alanine Helices," Proc. Nat'l Acad. Sci. USA 99(24):15416-15421 (2002).
Chittenden, et al. A conserved domain in Bak, distinct from BH1 and BH2, mediates cell death and protein binding functions. EMBO J. Nov. 15, 1995;14(22):5589-96.
Choi, et al. Application of azide-alkyne cycloaddition 'click chemistry' for the synthesis of Grb2 SH2 domain-binding macrocycles. Bioorg Med Chem Lett. Oct. 15, 2006;16(20):5265-9.
Chu, et al. Peptide-formation on cysteine-containing peptide scaffolds. Orig Life Evol Biosph. Oct. 1999;29(5):441-9.
Cleary, et al. Nucleotide sequence of a t(14;18) chromosomal breakpoint in follicular lymphoma and demonstration of a breakpoint-cluster region near a transcriptionally active locus on chromosome 18. Proc Natl Acad Sci U S A. Nov. 1985;82(21):7439-43.
Cline, et al. Effects of As(III) binding on alpha-helical structure. J Am Chem Soc. Mar. 12, 2003;125(10):2923-9.
Co-pending U.S. Appl. No. 13/494,846, filed Jun. 12, 2012.
Co-pending U.S. Appl. No. 13/655,442, filed Oct. 18, 2010.
Co-pending U.S. Appl. No. 13/784,345, filed Mar. 4, 2013.
Co-pending U.S. Appl. No. 14/483,905, filed Sep. 11, 2014.
Co-pending U.S. Appl. No. 14/677,679, filed Apr. 2, 2015.
Danial, et al. Cell death: critical control points. Cell. 2004; 116:204-219.
Definition of Analog from http://cancerweb.ncl.ac.uk/cgi-bin/omd?query=analog. pp. 1-5. Accessed Jul. 7, 2005.
Degterev et al., "Identification of Small-molecule Inhibitors of Interaction between the BH3 Domain and Bcl-xL," Nature Cell Biol. 3:173-182 (2001).
Deng, et al. Cross-Coupling Reaction of Iodo-1,2,3-triazoles Catalyzed by Palladium. Synthesis 2005(16): 2730-2738.
Designing Custom Peptide. from SIGMA Genosys, pp. 1-2. Accessed Dec. 16, 2004.
Dimartino et al. Solid-phase synthesis of hydrogen-bond surrogate-derived alpha-helices. Org Lett. Jun. 9, 2005;7(12):2389-92.
Erlanson, et al. Facile synthesis of cyclic peptides containing di-, tri-, tetra-, and Pentasulfides. Tetrahedron Letters. 1998; 39(38):6799-6802.
Felix et al., "Synthesis, Biological Activity and Conformational Analysis of Cyclic GRF Analogs," Int. J. Pep. Protein Res. 32:441-454 (1988).
Feng et al. Solid-phase SN2 macrocyclization reactions to form beta-turn mimics. Org Lett. Jul. 15, 1999;1(1):121-4.
Fields, et al. Chapter 3 in Synthetic Peptides: A User's Guide. Grant W.H. Freeman & Co. New York, NY. 1992. p. 77.
Fieser, et al. Fieser and Fieser's Reagents for Organic Synthesis. John Wiley and Sons. 1994.
Fischer, et al. Apoptosis-based therapies and drug targets. Cell Death and Differentiation. 2005; 12:942-961.
Fulda, et al. Extrinsic versus intrinsic apoptosis pathways in anticancer chemotherapy. Oncogene. Aug. 7, 2006;25(34):4798-811.

Galande, et al. Thioether side chain cyclization for helical peptide formation: inhibitors of estrogen receptor-coactivator interactions. Journal of Peptide Research. 2004; 63(3): 297-302.
Galande, et al. An effective method of on-resin disulfide bond formation in peptides. J Comb Chem. Mar.-Apr. 2005;7(2):174-7.
Galluzzi, et al. Guidelines for the use and interpretation of assays for monitoring cell death in higher eukaryotes. Cell Death Differ. Aug. 2009;16(8):1093-107. Epub Apr. 17, 2009.
Ghadiri & Choi, "Secondary Structure Nucleation in Peptides. Transition Metal Ion Stabilized α-Helices," J. Am. Chem. Soc. 112:1630-1632 (1990).
Goncalves, et al. On-resin cyclization of peptide ligands of the Vascular Endothelial Growth Factor Receptor 1 by copper(I)-catalyzed 1,3-dipolar azide-alkyne cycloaddition. Bioorg Med Chem Lett. Oct. 15, 2007;17(20):5590-4.
Greene, et al. Protective Groups in Organic Synthesis, 2nd Ed. John Wiley and Sons. 1991.
Greenlee et al., A General Synthesis of a-vinyl-a-amino acids. Tetrahedron Letters. 1978;42:3999-40002.
Grubbs et al. Ring Closing Metathesis and Related Processes in Organic Synthesis. Acc. Chem. Res. 1995;28:446-452.
Hanessian, et al. Structure-based design and synthesis of macroheterocyclic peptidomimetic inhibitors of the aspartic protease beta-site amyloid precursor protein cleaving enzyme (BACE). J Med Chem. Jul. 27, 2006;49(15):4544-67.
Hara, S. et al. 'Synthetic studies on halopeptins, anti-inflammatory cyclodepsipeptides', Peptide Science. 2006 (vol. date 2005), 42nd, pp. 39-42.
Hase; et al., "1,6-Aminosuberic acid analogs of lysine- and arginine-vasopressin and -vasotocin. Synthesis and biological properties. J Am Chem Soc. May 17, 1972;94(10):3590-600."
Hein, et al. Copper(I)-Catalyzed Cycloaddition of Organic Azides and 1-Iodoalkynes. Angew Chem Int Ed Engl. 2009;48(43):8018-21.
Hiroshige, et al. Palladium-mediated macrocyclisations on solid support and its applica-tions to combinatorial synthesis. J. Am. Chem. Soc. 1995; 117:11590-11591.
Horne, et al. Heterocyclic peptide backbone modifications in an alpha-helical coiled coil. J Am Chem Soc. Dec. 1, 2004;126(47):15366-7.
Hoveyda et al., "Ru Complexes Bearing Bidentate Carbenes: From Innocent Curiosity to Uniquely Effective Catalysts for Olefin Metathesis," Org. Biomolec. Chem. 2:8-23 (2004).
Hu, et al. Efficient p53 activation and apoptosis by simultaneous disruption of binding to MDM2 and MDMX. Cancer Res. Sep. 15, 2007;67(18):8810-7.
International search report and written opinion dated Mar. 3, 2014 for PCT/US2013/068147.
International search report and written opinion dated May 23, 2013 for PCT/US2013/026241.
International search report and written opinion dated May 29, 2013 for PCT/US2013/026238.
International search report and written opinion dated Oct. 12, 2011 for PCT/US2011/047692.
International search report dated Nov. 30, 2009 for PCT Application No. US2009/02225.
International search report dated Apr. 28, 2008 for PCT Application No. US2007/87615.
International search report dated May 18, 2005 for PCT Application No. US2004/38403.
International search report dated Sep. 25, 2008 for PCT Application No. US2008/54922.
International Search Report for PCT/US2014/025544, mailed Sep. 10, 2014.
Isidro-Llobet, et al. Amino acid-protecting groups. Chem Rev. Jun. 2009;109(6):2455-504. doi: 10.1021/cr800323s.
Jackson et al. General approach to the synthesis of short alpha-helical peptides. JACS. 1991;113:9391-9392.
Ji, et al. In vivo activation of the p53 tumor suppressor pathway by an engineered cyclotide. J Am Chem Soc. Aug. 7, 2013;135(31):11623-33. doi: 10.1021/ja405108p. Epub Jul. 25, 2013.

(56) References Cited

OTHER PUBLICATIONS

Jin, et al. Structure-based design, synthesis, and activity of peptide inhibitors of RGS4 GAP activity. Methods Enzymol. 2004;389:266-77.

Jin, et al. Structure-based design, synthesis, and pharmacologic evaluation of peptide RGS4 inhibitors. J Pept Res. Feb. 2004;63(2):141-6.

Johannasson, et al. Vinyl sulfide cyclized analogues of angiotensin II with high affinity and full agonist activity at the AT(1) receptor. J Med Chem. Apr. 25, 2002;45(9):1767-77.

Kallen, et al. Crystal structures of human MdmX(HdmX) in complex with p53 peptide analogues reveal surprising conformational changes. Journal of Biological Chemistry. Mar. 27, 2009; 284:8812-8821.

Kanan et al. Reaction discovery enabled by DNA-templated synthesis and in vitro selection. Nature. Sep. 30, 2004;431(7008):545-9.

Karle, et al. Structural charateristics of alpha-helical peptide molecules containing Aib residues. Biochemistry. Jul. 24, 1990;29(29):6747-56.

Karle. Flexibility in peptide molecules and restraints imposed by hydrogen bonds, the Aib residue, and core inserts. Biopolymers. 1996;40(1):157-80.

Kedrowski, B.L. et al. 'Thiazoline ring formation from 2-methylcysteines and 2-halomethylalanines', Heterocycles. 2002, vol. 58, pp. 601-634.

Kelso et al., "A Cyclic Metallopeptide Induces α Helicity in Short Peptide Fragments of Thermolysin," Angew. Chem. Int. Ed. 42(4):421-424 (2003).

Kelso et al., "α-Turn Mimetics: Short Peptide α-Helices Composed of Cyclic Metallopentapeptide Modules," J. Am. Chem. Soc. 126:4828-4842 (2004).

Kemp et al., "Studies of N-Terminal Templates for α-Helix Formation. Synthesis and Conformational Analysis of (2S,5S,8S,11S)-1-Acetyl-1,4-diaza-3-keto-5-carboxy-10-thiatricyclo[2.8.1.04,8]-tridecane (Ac-Hel1-OH)," J. Org. Chem. 56:6672-6682 (1991).

Kent. Advanced Biology. Oxford University Press. 2000.

Kilby et al., "Potent Suppression of HIV-1 Replication in Humans by T-20, a Peptide Inhibitor of gp41-Mediated Virus Entry," Nat. Med. 4(11):1302-1307 (1998).

Kinzler et al., Lessons from hereditary colorectal cancer. Cell. Oct. 18, 1996;87(2):159-70.

Kritzer et al., "Helical β-Peptide Inhibitors of the p53-hDM2 Interaction," J. Am. Chem. Soc. 126:9468-9469 (2004).

Kudaj, et al. An efficient synthesis of optically pure alpha-alkyl-beta-azido- and alpha-alkyl-beta-aminoalanines via ring opening of 3-amino-3-alkyl-2-oxetanones. Tetrahedron Letters. 2007; 48:6794-6797.

Kutzki et al., "Development of a Potent Bcl-xL Antagonist Based on α-Helix Mimicry," J. Am. Chem. Soc. 124:11838-11839 (2002).

Kwon, et al. Quantitative comparison of the relative cell permeability of cyclic and linear peptides. Chem Biol. Jun. 2007;14(6):671-7.

Larock, R.C. Comprehensive Organic Transformations, New York: VCH Publishers; 1989.

Leduc et al., Helix-stabilized cyclic peptides as selective inhibitors of steroid receptor-coactivator interactions. Proc Natl Acad Sci USA. 2003;100(20):11273-78.

Lee, et al. A Novel BH3 ligand that selectively targets Mcl-1 reveals that apoptosis can proceed without Mcl-1 degradation. J Cell Biol. Jan. 28, 2008;180(2):341-355.

Li, et al. A convenient preparation of 5-iodo-1,4-disubstituted-1,2,3-triazole: multicomponet one-pot reaction of azide and alkyne mediated by CuI-NBS. J Org Chem. May 2, 2008;73(9):3630-3. doi: 10.1021/0800035v. Epub Mar. 22, 2008.

Li; et al., "A versatile platform to analyze low-affinity and transient protein-protein interactions in living cells in real time.", 2014, 9(5):, 1946-58.

Li, et al. Structure-based design of thioether-bridged cyclic phosphopeptides binding to Grb2-SH2 domain. Bioorg Med Chem Lett. Mar. 10, 2003;13(5):895-9.

Li, et al. Systematic mutational analysis of peptide inhibition of the p53-MDM2/MDMX interactions. J Mol Biol. Apr. 30, 2010;398(2):200-13. doi:10.1016/j.jmb.2010.03.005. Epub Mar. 10, 2010.

Litowski & Hodges, "Designing Heterodimeric Two-stranded α-Helical Coiled-coils: Effects of Hydrophobicity and α-Helical Propensity on Protein Folding, Stability, and Specificity," J. Biol. Chem. 277(40):37272-37279 (2002).

Lu, et al. Proteomimetic libraries: design, synthesis, and evaluation of p53-MDM2 interaction inhibitors. J Comb Chem. May-Jun. 2006;8(3):315-25.

Luo, et al. Mechanism of helix induction by trifluoroethanol: a framework for extrapolating the helix-forming properties of peptides from trifluoroethanol/water mixtures back to water. Biochemistry. Jul. 8, 1997;36(27):8413-21.

Luo, et al. Wnt signaling and hunian diseases: What are the therapeutic implications? Lab Invest. Feb. 2007; 87(2):97-103. Epub Jan. 8, 2007.

Lyu, et al. Capping Interactions in Isolated α Helices: Position-dependent Substitution Effects and Structure of Serine-capped Peptide Helix. Biochemistry. 1993; 32:421-425.

Lyu et al, "α-Helix Stabilization by Natural and Unnatural Amino Acids with Alkyl Side Chains," Proc. Nat'l Acad. Sci. USA 88:5317-5320 (1991).

Mai, et al. A proapoptotic peptide for the treatment of solid tumors. Cancer Research. 2001; 61:7709-7712.

Mangold, et al. Azidoalanine mutagenicity in Salmonella: effect of homologation and alpha-Mutat Res. Feb. 1989 ;216(1):27-33. methyl substitution.

Mannhold, R., Kubinyi, H., Folkers, G., series eds. Molecular Drug Properties: Measurement and Prediction (Methods and Principles in Medicinal Chemistry). Wiley-VCH; 2007.

Martin, et al. Thermal [2+2] intramolecular cycloadditions of fuller-1,6-enynes. Angew Chem Int Ed Engl. Feb. 20, 2006;45(9):1439-42.

McGahon, et al. The end of the (cell) line: methods for the study of apoptosis in vitro. Methods Cell Biol. 1995;46:153-85.

Moellering et al., Abstract 69. Computational modeling and molecular optimization of stabilized alpha-helical peptides targeting NOTCH-CSL transcriptional complexes. Nov. 2010; 8(7):30. DOI: 10.1016/S1359-6349(10)71774-2. Abstract Only, European Journal of Cancer Supplements, 2010, 8(7).

Mosberg, et al. Dithioeter-containing cyclic peptides. J. Am. Chem. Soc. 1985;107(10):2986-2987.

Muchmore, et al. X-ray and NMR structure of human Bcl-xL, an inhibitor of programmed cell death. Nature. May 23, 1996;381(6580):335-41.

Mulqueen et al. Synthesis of the thiazoline-based siderophore (S)-desferrithiocin. 1993;48(24):5359-5364.

Mustapa, et al. Synthesis of a Cyclic Peptide Containing Norlanthionine: Effect of the Thioether Bridge on Peptide Conformation. J. Org. Chem. 2003;68(21):8193-8198.

Nelson & Kallenbach, "Persistence of the α-Helix Stop Signal in the S-Peptide in Trifluoroethanol Solutions," Biochemistry 28:5256-5261 (1989).

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

Non-Final Office Action dated Dec. 5, 2008 from U.S. Appl. No 10/981,873.

Notice of allowance Mar. 22, 2010 for U.S. Appl. No. 11/148,976.

Notice of allowance Jul. 7, 2009 for U.S. Appl. No. 10/981,873.

Notice of allowance dated Jan. 7, 2015 for U.S. Appl. No. 13/370,057.

Notice of allowance dated Jan. 27, 2014 for U.S. Appl. No. 12/233,555.

Notice of allowance dated May 4, 2004 for U.S. Appl. No. 09/574,086.

(56) References Cited

OTHER PUBLICATIONS

Notice of allowance dated May 8, 2012 for U.S. Appl. No. 12/182,673.
Notice of allowance dated Jun. 12, 2014 for U.S. Appl. No. 12/525,123.
Notice of allowance dated Jul. 28, 2014 for U.S. Appl. No. 13/680,905.
Notice of allowance dated Aug. 1, 2014 for U.S. Appl. No. 13/767,852.
Notice of allowance dated Nov. 6, 2014 for U.S. Appl. No. 13/767,857.
Notice of Allowance, mailed Aug. 6, 2012, for U.S. Appl. No. 12/796,212.
Office action dated Jan. 3, 2013 for U.S. Appl. No. 12/593,384.
Office action dated Jan. 13, 2014 for U.S. Appl. No. 13/767,857.
Office action dated Jan. 17, 2014 for U.S. Appl. No. 13/816,880.
Office action dated Jan. 26, 2009 for U.S. Appl. No. 11/148,976.
Office Action dated Jan. 30, 2008 for U.S. Appl. No. 10/981,873.
Office action dated Feb. 4, 2014 for U.S. Appl. No. 13/370,057.
Office action dated Feb. 6, 2014 for U.S. Appl. No. 13/680,905.
Office action dated Feb. 9, 2012 for U.S. Appl. No. 12/420,816.
Office action dated Feb. 17, 2011 for U.S. Appl. No. 12/796,212.
Office action dated Feb. 24, 2015 for U.S. Appl. No. 13/252,751.
Office action dated Mar. 18, 2013 for U.S. Appl. No. 13/097,930.
Office action dated Mar. 18, 2015 for U.S. Appl. No. 14/070,367.
Office action dated Mar. 22, 2013 for U.S. Appl. No. 12/233,555.
Office action dated Mar. 26, 2015 for U.S. Appl. No. 14/070,354.
Office action dated Apr. 9, 2014 for U.S. Appl. No. 13/767,852.
Office action dated Apr. 10, 2015 for U.S. Appl. No. 14/460,848.
Office action dated Apr. 18, 2011 for U.S. Appl. No. 12/182,673.
Office action dated Apr. 26, 2012 for U.S. Appl. No. 13/097,930.
Office action dated May 10, 2010 for U.S. Appl. No. 11/957,325.
Office action dated May 19, 2010 for U.S. Appl. No. 12/140,241.
Office action dated Jun. 28, 2012 for U.S. Appl. No. 12/233,555.
Office action dated Jun. 28, 2013 for U.S. Appl. No. 13/370,057.
Office action dated Jul. 15, 2013 for U.S. Appl. No. 13/570,146.
Office action dated Jul. 16, 2014 for U.S. Appl. No. 13/767,857.
Office action dated Jul. 21, 2014 for U.S. Appl. No. 13/370,057.
Office action dated Jul. 30, 2013 for U.S. Appl. No. 13/097,930.
Office action dated Aug. 9, 2010 for U.S. Appl. No. 12/182,673.
Office action dated Aug. 10, 2009 for U.S. Appl. No. 11/957,325.
Office action dated Aug. 11, 2009 for U.S. Appl. No. 12/140,241.
Office action dated Aug. 19, 2010 for U.S. Appl. No. 12/037,041.
Office action dated Sep. 18, 2013 for U.S. Appl. No. 13/767,857.
Office action dated Sep. 23, 2013 for U.S. Appl. No. 13/680,905.
Office action dated Oct. 10, 2013 for U.S. Appl. No. 13/816,880.
Office action dated Oct. 15, 2012 for U.S. Appl. No. 13/097,930.
Office action dated Oct. 18, 2011 for U.S. Appl. No. 12/796,212.
Office action dated Oct. 31, 2014 for U.S. Appl. No. 13/370,057.
Office action dated Nov. 5, 2002 for U.S. Appl. No. 09/574,086.
Office action dated Nov. 25, 2009 for U.S. Appl. No. 11/148,976.
Office action dated Dec. 13, 2012 for U.S. Appl. No. 12/690,076.
Office action dated Dec. 19, 2014 for U.S. Appl. No. 14/068,844.
Office action dated Dec. 29, 2011 for U.S. Appl. No. 12/233,555.
Office action dated Dec. 31, 2013 for U.S. Appl. No. 12/525,123.
O'Neil & DeGrado, "A Thermodynamic Scale for the Helix-forming Tendencies of the Commonly Occurring Amino Acids," Science 250:646-651(1990).
Or et al. Cysteine alkylation in unprotected peptides: synthesis of a carbavasopressin analogue by intramolecular cystein alkylation. J. Org. Chem. Apr. 1991;56(9):3146-3149.
Paquette, L.A., ed. Encyclopedia of Reagents for Organic Synthesis. New York; John Wiley & Sons; 1995.
Pattenden, et al. Enantioselective synthesis of 2-alkyl substituted cysteines. 1993;49(10):2131-2138.
Pattenden, et al. Naturally occurring linear fused thiazoline-thiazole containing metabolites: total synthesis of (-)-didehydromirabazole A, a cytotoxic alkaloid from blue-green algae. J Chem Soc. 1993;14:1629-1636.

Pazgier, et al. Structural basis for high-affinity peptide inhibition of p53 interactions with MDM2 and MDMX. Proc Natl Acad Sci U S A. Mar. 24, 2009;106(12):4665-70. doi: 10.1073/pnas.0900947106. Epub Mar. 2, 2009.
Perantoni, Renal development: perspectives on a Wnt-dependent process. Semin Cell Dev Biol. Aug. 2003;14(4):201-8.
Peryshkov, et al. Z-Selective olefin metathesis reactions promoted by tungsten oxo alkylidene complexes. Am Chem Soc. Dec. 28, 2011; 133(51):20754-7. doi:10.1021/ja210349m. Epub Nov. 30, 2011.
Phan, et al. Structure-based design of high affinity peptides inhibiting the interaction of p53 with MDM2 and MDMX. J Biol Chem. Jan. 15, 2010;285(3):2174-83. doi: 10.1074/jbc.M109.073056. Epub Nov. 12, 2009.
Phelan et al. A General Method for Constraining Short Peptides to an αHelical Conformation. J. Am. Chem. Soc. 1997;119:455-460.
Punna, et al. Head-to-tail peptide cyclodimerization by copper-catalyzed azide-alkyne cycloaddition. Angew Chem Int Ed Engl. Apr. 8, 2005;44(15):2215-20.
Qiu et al., Convenient, Large-Scale Asymmetric Synthesis of Enantiomerically Pure trans-Cinnamylglycine and -a-Alanine. Tetrahedron. 2000;56:2577-82.
Rink, et al. Lantibiotic Structures as Guidelines for the Design of Peptides That Can Be Modified by Lantibiotic Enzymes. Biochemistry. 2005; 44:8873-8882.
Roberts, et al. Efficient synthesis of thioether-based cyclic peptide libraries. Tetrahedon Letters. 1998; 39: 8357-8360.
Roberts, et al. Examination of methodology for the synthesis of cyclic thioether peptide libraries derived from linear tripeptides. J Pept Sci. Dec. 2007;13(12):811-21.
Roice, et al. High Capacity Poly(ethylene glycol) Based Amino Polymers for Peptide and Organic Synthesis. QSAR & Combinatorial Science. 2004;23(8):662-673.
Rojo, et al. Macrocyclic peptidomimetic inhibitors of β-secretase (BACE): First X-ray structure of a macrocyclic peptidomimetic-BACE complex. Bioorg. Med. Chem. Lett. 2006; 16:191-195.
Roof, et al. Mechanism of action and structural requirements of constrained peptide inhibitors of RGS proteins. Chem Biol Drug Des. Apr. 2006;67(4):266-74.
Ruan et al., "Metal Ion Enhanced Helicity in Synthetic Peptides Containing Unnatural, Metal-ligating Residues," J. Am. Chem. Soc. 112:9403-9404 (1990).
Rudinger J, "Characteristics of the amino acids as components of a peptide hormone sequence," Peptide Hormones, JA Parsons Edition, University Park Press, Jun. 1976, pp. 1-7.
Ruffolo and Shore. BCL-2 Selectively Interacts with the BID-Induced Open Conformer of BAK, Inhibiting BAK Auto-Oligomerization. J. Biol. Chern. 2003;278(27):25039-25045.
Saghiyan, A. S., et al., "New chiral Niii complexes of Schiffs bases of glycine and alanine for efficient asymmetric synthesis of a-amino acids," Tedrahedron: Asymmetry 17: 455-467 (2006).
Saghiyan, et al. Novel modified (S)-N-(benzoylphenyl)-1-(3,4-dichlorobenzyl)-pyrolidine-2-carboxamide derived chiral auxiliarie for asymmetric synthesis of (S)-alpha-amino acids. Chemical Journal of Armenia. Aug. 2002; 55(3):150-161 (abstract only).
Sanchez-Garcia, et al. Tumorigenic activity of the BCR-ABL oncogenes is mediated by BCL2. Proc Natl Aced Sci U S A. Jun. 6, 1995;92(12):5287-91.
Ösapay & Taylor, "Multicyclic Polypeptide Model Compounds. 2. Synthesis and Conformational Properties of a Highly α-Helical Uncosapeptide Constrained by Three Side-chain to Side-chain Lactam Bridges," J. Am. Chem. Soc. 114:6966-6973 (1992).
Sattler et al. Structure of Bcl-xL-Back peptide complex: recognition between regulators of apoptosis. Science. 1997;275:983-986.
Schafmeister et al. An all-hydrocarbon crosslinking system for enhancing the helicity and metabolic stability of peptides. J. Am Chem. Soc. 2000;122:5891-5892.
Schinzel et al., The phosphate recognition site of *Escherichia coli* maltodextrin phosphorylase. FEBS Lett. Jul. 29, 1991;286(1-2):125-8.
Scorrano, et al. A distinct pathway remodels mitochondrial cristae and mobilizes cytochrome c during apoptosis. Dev Cell. Jan. 2002;2(1):55-67.

(56) References Cited

OTHER PUBLICATIONS

Scott, et al. A Solid-Phase Synthetic Route to Unnatural Amino Acids with Diverse Side-Chain Substitutions. Journal of Organic Chemistry. 2002, vol. 67, No. 9, pp. 2960-2969.
Seebeck, et al. Ribosomal synthesis of dehydroalanine-containing peptides. J Am Chem Soc. Jun. 7, 2006;128(22):7150-1.
Shepherd et al., "Single Turn Peptide Alpha Helices with Exceptional Stability in Water," J. Am. Chem. Soc. 127:2974-2983 (2005).
Shi, et al. The role of arsenic-thiol interactions in metalloregulation of the ars operant. J Biol Chem. Apr. 19, 1996;271(16):9291-7.
Sia et al., "Short Constrained Peptides that Inhibit HIV-1 Entry," Proc. Nat'l Acad.Sci. USA 99(23):14664-14669 (2002).
Singh, et al. Efficient asymmetric synthesis of (S)- and (R)-N-Fmoc-S-trityl-alpha-methylcysteine using camphorsultam as a chiral auxiliary . . . J Org Chem. Jun. 25, 2004;69(13):4551-4.
Smith, et al. Design, Synthesis, and Binding Affinities of Pyrrolinone-Based Somatostatin Mimetics. Organic Letters. Jan. 8, 2005, vol. 7, No. 3, pp. 399-402, plus Supporting Information, pp. S1-S39.
Solution phase synthesis from http://www.combichemistry.com/solution_phase_synthesis.html. p. 1. Accessed Aug. 6, 2009.
Spierings, et al. Connected to death: the (unexpurgated) mitochondrial pathway of apoptosis. Science. 2005; 310:66-67.
Stewart, et al. Cell-penetrating peptides as delivery vehicles for biology and medicine. Org Biomol Chem. Jul. 7, 2008; 6(13):2242-55. doi: 10.1039/b719950c. Epub Apr. 15, 2008.
STN search notes for Lu reference, 4 pages, 2006.
Suzuki, et al. Structure of Bax: coregulation of dimer formation and intracellular localization. Cell. Nov. 10, 2000;103(4):645-54.
Szewczuk, et al. Synthesis and Biological activity of new conformationally restricted analogues of pepstatin. Int. J. Peptide Protein. Res. 1992; 40:233-242.
Tam, et al. Protein prosthesis: 1,5-disubstituted[1,2,3]triazoles as cis-peptide bond surrogates. J Am Chem Soc. Oct. 24, 2007;129(42):12670-1.
Tanaka, Design and synthesis of non-proteinogenic amino acids and secondary structures of their peptides. Yakugaku Zasshi. Oct. 2006:126(10):931-44.
Taylor. The synthesis and study of side-chain lactam-bridged peptides. Biopolymers. 2002;66(1):49-75.
Titus, et al. Human K/natural killer cells targeted with hetero-cross-linked antibodies specifically lyse tumor cells in vitro and prevent tumor growth in vivo. J Immunol. Nov. 1, 1987;139(9):3153-8.
Torres, et al. Peptide tertiary structure nucleation by side-chain crosslinking with metal complexation and double "click" cycloaddition. Chembiochem. Jul. 21, 2008;9(11):1701-5.
Trnka & Grubbs, "The Development of L2X2Ru=CHR Olefin Metathesis Catalysts: An Organometalli Success Story," Acc. Chem. Res. 34:18-29 (2001).
Tugyi, et al. The effect of cyclization on the enzymatic degradation of herpes simplex virus glycoprotein D derived epitope peptide. J Pept Sci. Oct. 2005;11(10):642-9.
Tyndall et al. Macrocycles mimic the extended peptide conformation recognized by aspartic, serine, cysteine and metallo proteases. Curr Med Chem. Jul. 2001;8(8):893-907.
Ueki, et al. Improved synthesis of proline-derived Ni(II) complexes of glycine: versatile chiral equivalents of nucleophilic glycine for general asymmetric synthesis of alpha-amino acids. J Org Chem. Sep. 5, 2003;68(18):7104-7.
U.S. Appl. No. 61/385,405, filed Sep. 22, 2010.
Van Maarseveen, et al. Efficient route to C2 symmetric heterocyclic backbone modified cyclic peptides. Org Lett. Sep. 29, 2005;7(20):4503-6.
Viallet, et al. Tallimustine is inactive in patients with previously treated small cell lung cancer. A phase II trial of the National Cancer Institute of Canada Clinical Trials Group. Lung Cancer. Nov. 1996;15(3):367-73.
Voet D, Voet JG, Biochemistry, Second Edition, John Wiley & Sons, Inc., 1995, pp. 235-241.
Walensky, et al. Activation of apoptosis in vivo by a hydrocarbon-stapled BH3 helix. Science. Sep. 3, 2004;305(5689):1466-70.
Walker, et al. General method for the synthesis of cyclic peptidomimetic compounds. Tetrahedron Letters. 2001; 42(34):5801-5804.
Wang, et al. BID: a novel BH3 domain-only death agonist. Genes Dev. Nov. 15, 1996;10(22):2859-69.
Wang et al. Cell permeable Bcl-2 binding peptides: a chemical approach to apoptosis induction in tumor cells. Cancer Res. Mar. 15, 2000;60(6):1498-502.
Wang, et al. "Click" synthesis of small molecule probes for activity-based fingerprinting of matrix metalloproteases. Chem Commun (Camb). Sep. 28, 2006;(36):3783-5.
Wang et al. Enhanced metabolic stability and protein-binding properties of artificial helices derived from a hydrogen-bond surrogate: application to Bcl-xL. Angew Chem Int Ed Engl. Oct. 14, 2005;44(40):6525-9.
Wang, et al. Evaluation of biologically relevant short alpha-helices stabilized by a main-chain hydrogen-bond surrogate. J Am Chem Soc. Jul. 19, 2006;128(28):2948-56.
Wang, et al. Nucleation and stability of hydrogen-bond surrogate-based alpha-helices. Org Biomol Chem. Nov. 21, 2006;4(22):4074-81.
Wei, et al. tBID, a membrane-targetes death ligand, oligomerizes BAK to release cytochrome c. Genes Dev. Aug. 15, 2000;14(16):2060-71.
Wels, et al. Synthesis of a novel potent cyclic peptide MC4-ligand by ring-closing metathesis. Bioorg. Med. Chem. Lett. 2005; 13: 4221-4227.
Wild et al., "Peptides Corresponding to a Predictive α-Helical Domain of Human Immunodeficiency Virus Type 1 gp41 are Potent Inhibitors of Virus Infections," Proc. Nat'l Acad. Sci. USA 91:9770-9774 (1994).
Wilen, Tables of Resolving Agents and Optical Resolutions. E.L. Eliel, ed. University of Notre Dame Press, Notre Dame, IN. 1972:268-98.
Williams and IM. Asymmetric Synthesis of Nonsubstituted and α,α-Disubstituted α-Amino Acids via Diastereoselective Glycine Enolate Alkylations. JACS. 1991;113:9276-9286.
Wu, et al. Regiospecific Synthesis of 1,4,5-Trisubstituted-1,2,3-triazole via One-Pot Reaction Promoted by Copoper(I) Salt. Synthesis. 2005(8): 1314-1318.
Wu, et al. Studies on New Strategies for the Synthesis of Oligomeric 1,2,3-Triazoles. Synlett 2006(4): 06045-0647.
Yang, et al. Calculation of protein conformation form circualr dichroism. Methods Enzymol. 1986;130:208-69.
Yu, et al. Synthesis of macrocyclic natural products by catalyst-controlled stereoselective ring-closing metathesis. Nature. Nov. 2, 2011;479(7371):88-93. doi:10.1038/nature10563.
Zamzami et al. The thiol crosslinking agent diamide overcomes the apoptosis-inhibitory effect of Bcl-2 by enforcing mitochondrial permeability transition. Oncogene. Feb. 26, 1998;16(8):1055-63.
Zhang, et al. 310 Helix versus alpha-helix: a molecular dynamics study of conformational preferences of Aib and Alanine. J. American Cancer Society. Dec. 1994; 116(26):11915-11921.
Co-pending U.S. Appl. No. 15/278,824, filed Sep. 28, 2016.

\* cited by examiner

Column Used: Chiralpak AD-H QC#167
Vial: 73   Injection: 1
Injection Volume: 5.00 ul
Sample Concentration: 48.0mg/25mL DS
Additional Sample Information: Finished Product Solvent A: 90%Hex.anes/10%IPA/0.1%TFA
Solvent B: 90%Hex.anes/10%IPA
Solvent C: IPA
Solvent C: EtOH

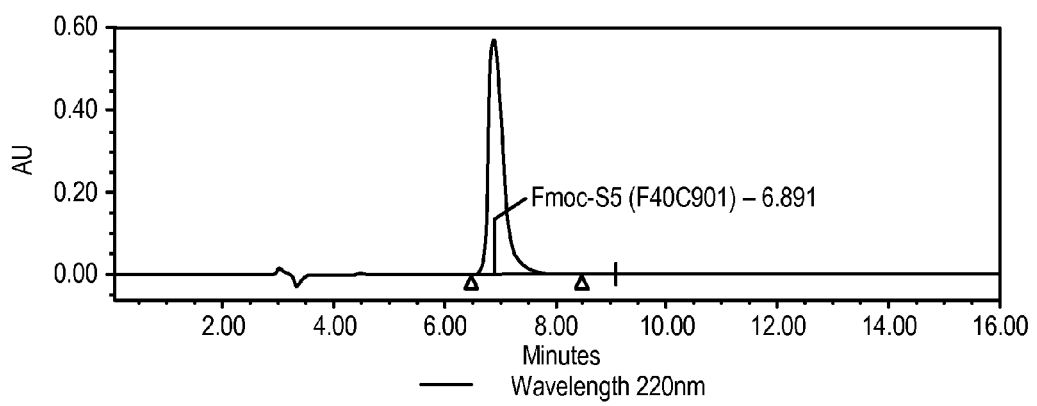

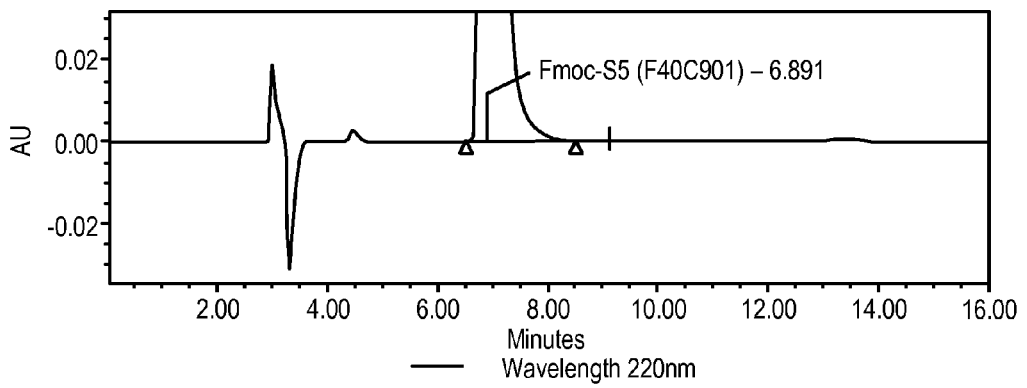

Results processed by 220nm

| | Peak Name | Retention Time | Peak Area | % Peak Area | | Peak Name | Retention Time | Peak Area | % Peak Area |
|---|---|---|---|---|---|---|---|---|---|
| 1 | Fmoc-S5 (F40C901) | 6.891 | 9858806 | 100.00 | 2 | Fmoc-S5 (F40C902) | 9.100 | | |

User Name: System                       Current Date: 12/19/2011 2:11:54 PM                       1 of 1

FIG. 1

Column Used: Chiralpak AD-H QC#167
Vial: 74   Injection: 1
Injection Volume: 5.00 ul
Sample Concentration: 48.0mg/25mL DS + 0.5% R5
Additional Sample Information: Sample+0.5% R5

Solvent A: 90%Hex.anes/10%IPA/0.1%TFA
Solvent B: 90%Hex.anes/10%IPA
Solvent C: IPA
Solvent C: EtOH

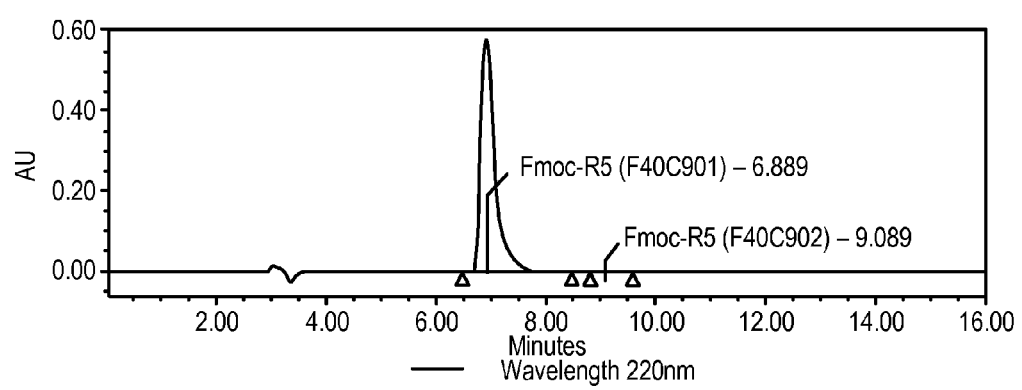

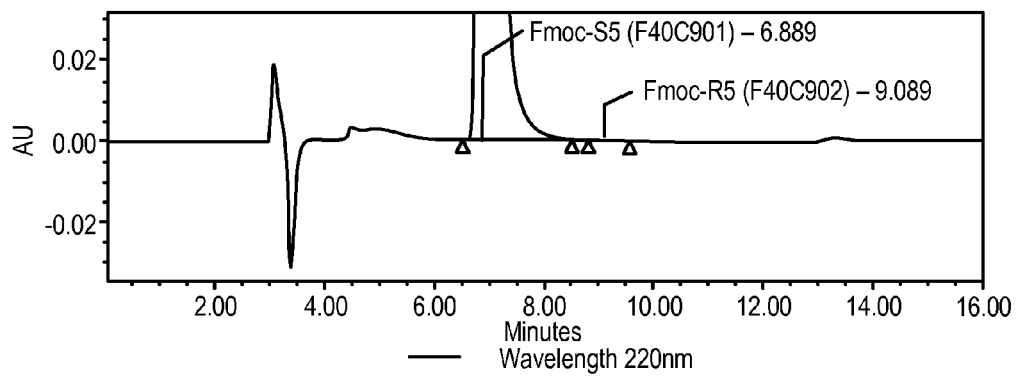

Results processed by 220nm

| | Peak Name | Retention Time | Peak Area | % Peak Area | | Peak Name | Retention Time | Peak Area | % Peak Area |
|---|---|---|---|---|---|---|---|---|---|
| 1 | Fmoc-S5 (F40C901) | 6.889 | 9847318 | 99.83 | 2 | Fmoc-S5 (F40C902) | 9.089 | 16328 | 0.17 |

User Name: System                Current Date: 12/19/2011 2:11:41 PM                1 of 1

FIG. 2

Column Used: Waters Spherisorb ODS2#131
Vial: 35   Injection: 1
Injection Volume: 5.00 ul
Sample Concentration: 26.1mg/25mL DS
Additional Sample Information: Sample Acq Method Set: F40C902_60to80in25min
Date Acquired: 12/20/2011 1:53:06 PM
Processing Method F40C902_60to80in25min
Date Processed: 12/20/2011 3:21:49 PM Data from Chromatogram 215nm

|   | Peak Name | Retention Time | Height (µV) | % Height | Peak Area | % Peak Area |
|---|---|---|---|---|---|---|
| 1 |  | 4.851 | 3099 | 0.33 | 24138 | 0.20 |
| 2 |  | 5.487 | 1580 | 0.17 | 21810 | 0.18 |
| 3 |  | 6.203 | 6569 | 0.71 | 62741 | 9.52 |
| 4 | F40C902 | 10.054 | 925370 | 98.56 | 11863328 | 98.49 |
| 5 |  | 11.060 | 2192 | 0.23 | 73331 | 0.61 |

Column Used: Waters Spherisorb ODS2#131  Date Acquired: 12/20/2011 1:53:06 PM
Vial: 35  Injection: 1  Processing Method F40C902_60to80in25min
Injection Volume: 5.00 ul  Date Processed: 12/20/2011 3:19:31 PM
Sample Concentration: 26.1mg/25mL DS
Additional Sample Information: Sample Data from Chromatogram 254nm

| | Peak Name | Retention Time | Height (μV) | % Height | Peak Area | % Peak Area |
|---|---|---|---|---|---|---|
| 1 | | 3.083 | 914 | 0.13 | 5380 | 0.06 |
| 2 | | 3.626 | 379 | 0.05 | 2548 | 0.03 |
| 3 | | 3.858 | 612 | 0.09 | 7057 | 0.08 |
| 4 | | 4.852 | 2303 | 0.32 | 17314 | 0.19 |
| 5 | | 5.484 | 967 | 0.14 | 8412 | 0.09 |
| 6 | | 6.206 | 2206 | 0.31 | 20714 | 0.23 |
| 7 | | 9.411 | 1420 | 0.20 | 14463 | 0.16 |
| 8 | F40C902 | 10.054 | 698574 | 98.50 | 8845126 | 98.36 |
| 9 | | 11.195 | 1818 | 0.26 | 71822 | 0.80 |

Column Used: Waters Spherisorb ODS2 #131
Vial: 36   Injection: 1
Injection Volume: 5.00 ul
Sample Concentration: 0.5mg/25mL DS
Additional Sample Information: Customer Control Date Acquired: 12/20/2011 2:44:05 PM
Processing Method F40C902_60to80in25min
Date Processed: 12/20/2011 3:24:26 PM Data from Chromatogram 215nm

| | Peak Name | Retention Time | Height (µV) | % Height | Peak Area | % Peak Area |
|---|---|---|---|---|---|---|
| 1 | F40C902 | 10.086 | 273598 | 100.00 | 3562385 | 100.00 |

Column Used: Waters Spherisorb ODS2 #131
Vial: 46  Injection: 1
Injection Volume: 5.00 ul Date Processed: 11/16/2011 7:19:45 PM
Processing Method F40C902_60to80in25min
Date Processed: 11/17/2011 4:04:32 PM Sample Concentration: 14.6mg/10mL DS
Additional Sample Information: N-Fmoc-(R)-a-Me-a-
    Aminodec-9-enoic Acid; FP;

Data from Chromatogram 215nm

|   | Peak Name | Retention Time | Height (µV) | % Height | Peak Area | % Peak Area |
|---|---|---|---|---|---|---|
| 1 | Fmoc-OnSu | 8.800 | | | | |
| 2 | | 15.504 | 494 | 0.04 | 9432 | 0.05 |
| 3 | 40C902 | 16.100 | | | | |
| 4 | | 16.149 | 1013 | 0.09 | 13695 | 0.08 |
| 5 | F40C902 | 18.334 | 1106791 | 99.81 | 17679588 | 99.82 |
| 6 | | 25.283 | 552 | 0.05 | 8025 | 0.05 |

Column Used: Waters Spherisorb ODS2 #131
Vial: 46  Injection: 1
Injection Volume: 5.00 ul
Sample Concentration: 14.6mg/10mL DS
Additional Sample Information:
N-Fmoc-(R)-a-Me-a-Aminodec-9-enoic Acid; FP;

Date Acquired: 11/16/2011 7:19:45 PM
Processing Method F40C902_60to80in25min
Date Processed: 11/17/2011 6:11:21 PM Data from Chromatogram 254nm

| | Peak Name | Retention Time | Height (µV) | % Height | Peak Area | % Peak Area |
|---|---|---|---|---|---|---|
| 1 | Fmoc-OnSu | 8.800 | | | | |
| 2 | 40C902 | 16.100 | | | | |
| 3 | F40C902 | 18.334 | 856815 | 99.96 | 13404558 | 99.95 |
| 4 | | 25.289 | 382 | 0.04 | 7053 | 0.05 |

DISUBSTITUTED AMINO ACIDS AND METHODS OF PREPARATION AND USE THEREOF

CROSS-REFERENCE

This application claims the benefit of U.S. Provisional Application No. 61/721,457, filed Nov. 1, 2012, and U.S. Provisional Application No. 61/799,917, filed Mar. 15, 2013, each of which is incorporated herein by reference in its entirety.

BACKGROUND OF THE INVENTION

α, α-Disubstituted amino acids bearing a terminal alkene on one of their side chains and their salts ("alkene α, α-disubstituted amino acids") are useful for making cross-linked macrocyclic peptides. For example, International Application No. PCT/US2004/038403 ("the '403 application") discloses incorporating into a peptide two α, α-disubstituted amino acids that each contain a side-chain bearing a terminal alkene, and cross-linking the terminal alkene groups to form a cross-linked ("stapled") macrocyclic peptide. The cross-link can, for example, stabilize a secondary structure (e.g., an α-helix) present in the stapled macrocyclic peptide.

International Application Publication No. WO2008/121767 ("the '767 publication") discloses using alkene α, α-disubstituted amino acids to form stitched polypeptides (e.g., multiple and tandem crosslinked polypeptides) having secondary structures stabilized by stitching. The '403 application, the '767 publication, and other applications, publications, and patents, disclose that stapled and stitched macrocyclic peptides are useful for treating and preventing various diseases including cancer.

Alkene α, α-disubstituted amino acids are thus important and useful building blocks for forming stitched and stapled polypeptides and their precursors. The use of alkene α, α-disubstituted amino acids, however, has been limited by an inability to provide these important molecules in crystalline form. For example, commercially available preparations of alkene α, α-disubstituted amino acids are typically sold as pre-made solutions. The pre-made solutions limit the amount of α, α-disubstituted amino acid that can be shipped per unit volume, limit the chemical reactions that are available to be run with the alkene α, α-disubstituted amino acids, subject the alkene α, α-disubstituted amino acids to an enhanced degradation rate, and are environmentally unfriendly. Thus, there remains a compelling need for crystalline alkene α, α-disubstituted amino acids and their crystalline salts, and processes for producing and using these crystalline amino acids.

In addition, substituting one or more hydrogen atoms of an alkene α, α-disubstituted amino acid with deuterium or a halogen atom can change one or more of the amino acid's properties. For example dipole moment, hydrophobicity, hydrophilicity, steric bulk, or reactivity of an alkene α, α-disubstituted amino acid can be changed by substituting one or more hydrogen atoms thereon with one or more deuterium or halogen atoms. Thus, there also remains a need for optionally crystalline alkene α, α-disubstituted amino acids and their optionally crystalline salts having one or more hydrogen atoms thereon substituted with deuterium or halogen, and methods of making and using these.

SUMMARY OF THE INVENTION

The above needs, and others, are addressed herein. The inventive embodiments provided in this Summary of the Invention are meant to be illustrative only and to provide an overview of selected inventive embodiments disclosed herein. The Summary of the Invention, being illustrative and selective, does not limit the scope of any claim, does not provide the entire scope of inventive embodiments disclosed or contemplated herein, and should not be construed as limiting or constraining the scope of this disclosure or any claimed inventive embodiment.

Provided herein are crystalline compounds of Formula (I) and crystalline salts thereof:

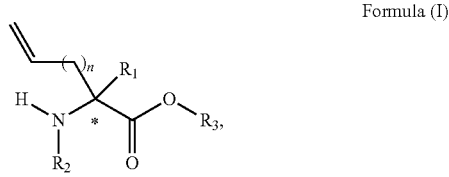

Formula (I)

wherein $R_1$ is $C_1$-$C_3$ alkyl, $C_1$-$C_3$ deuteroalkyl, or $C_1$-$C_3$ haloalkyl; * is a stereocenter; n is an integer from 1 to 20; $R_2$ is —H or a nitrogen protecting group; and $R_3$ is —H or a protecting or activating group.

Also provided herein are methods of preparing a polypeptide, comprising making the polypeptide with one or more crystalline compounds of Formula (I) or their crystalline salts.

Further provided herein are methods of making crystalline compounds of Formula (I) or their crystalline salts, comprising at least one of the following purifications:
1) Crystallizing a metal complex of Formula (XIb)

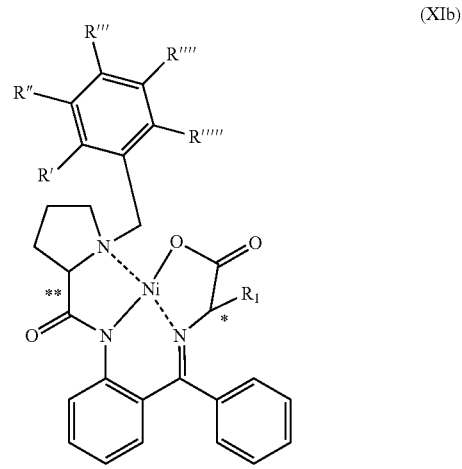

(XIb)

from one or more solvents, optionally a cyclic ether, optionally tetrahydrofuran and methyl tert-butyl ether, or optionally an alcohol, optionally isopropyl alcohol, optionally an ester, optionally isopropyl acetate, optionally ethyl acetate, wherein $R_1$ is $C_1$-$C_3$ alkyl, $C_1$-$C_3$ deuteroalkyl, or $C_1$-$C_3$ haloalkyl, * and ** are each independently stereocenters, and R', R'', R''', R'''', and R''''' are, in the order going around the aromatic ring from R' to R''''', selected from
  H, H, Cl, Cl, H;
  F, F, F, F, F;
  F, F, OiPr, F, F;
  F, F, OMe, F, F;
  Cl, H, H, H, H; or
  H, H, Me, Me, H;

2) Precipitating a compound of Formula (Ia) as its HCl salt:

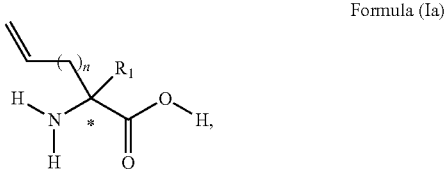

Formula (Ia)

wherein $R_1$ is $C_1$-$C_3$ alkyl, $C_1$-$C_3$ deuteroalkyl, or $C_1$-$C_3$ haloalkyl, n is an integer from 1 to 20, and * is a stereocenter;

3) Forming an addition salt of Formula (XIVb):

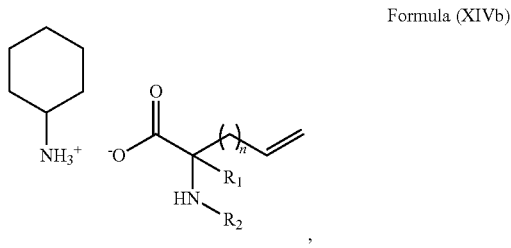

Formula (XIVb)

wherein $R_1$ is $C_1$-$C_3$ alkyl, $C_1$-$C_3$ deuteroalkyl, or $C_1$-$C_3$ haloalkyl, $R_2$ is a nitrogen protecting group, n is an integer from 1 to 20, and * is a stereocenter; or 4) Crystallizing a compound of Formula (I) or a salt thereof from one or more solvents, optionally chloroform and hexanes.

In some embodiments, the compound of Formula (XIb) is crystallized in a mixture of tetrahydrofuran and methyl t-butyl ether. In some embodiments, the ratio of tetrahydrofuran and methyl t-butyl ether is between: 1:10 and 3:10. For example, the ratio is 1.5:10.

In some embodiments, the compound of Formula (I) or a salt thereof is crystallized in a mixture of chloroform and hexanes. In some embodiments, the ratio of chloroform to hexanes is between 1:5 and 1:1. For example, the ratio is 1:3 or 1:2. Also provided herein are methods of preparing a polypeptide, comprising making the polypeptide with one or more crystalline compounds of Formula (I) or their crystalline salts.

BRIEF DESCRIPTION OF THE DRAWINGS

FIG. 1 is a chiral HPLC trace of N-Fmoc-(S)-alpha-methyl-alpha-amino-6-enoic acid.

FIG. 2 is a chiral HPLC trace of N-Fmoc-(S)-alpha-methyl-alpha-amino-6-enoic acid spiked with N-Fmoc-(R)-alpha-methyl-alpha-amino-6-enoic acid.

INCORPORATION BY REFERENCE

Figure 3:
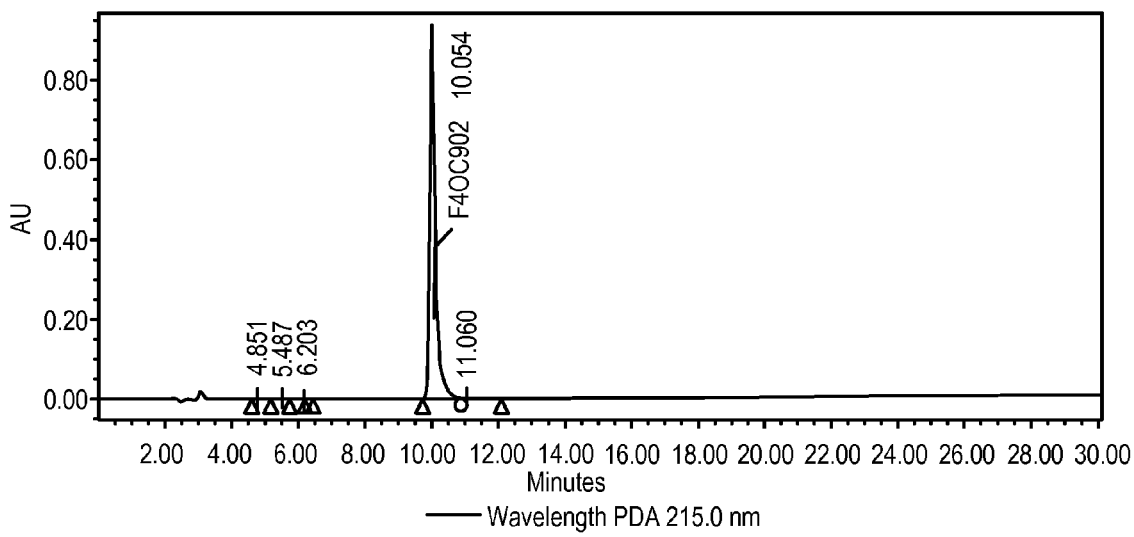
FIG. 3 is an HPLC trace of N-Fmoc-(S)-alpha-methyl-alpha-amino-6-enoic acid with the detector set to 215 nm.
Figure 4:
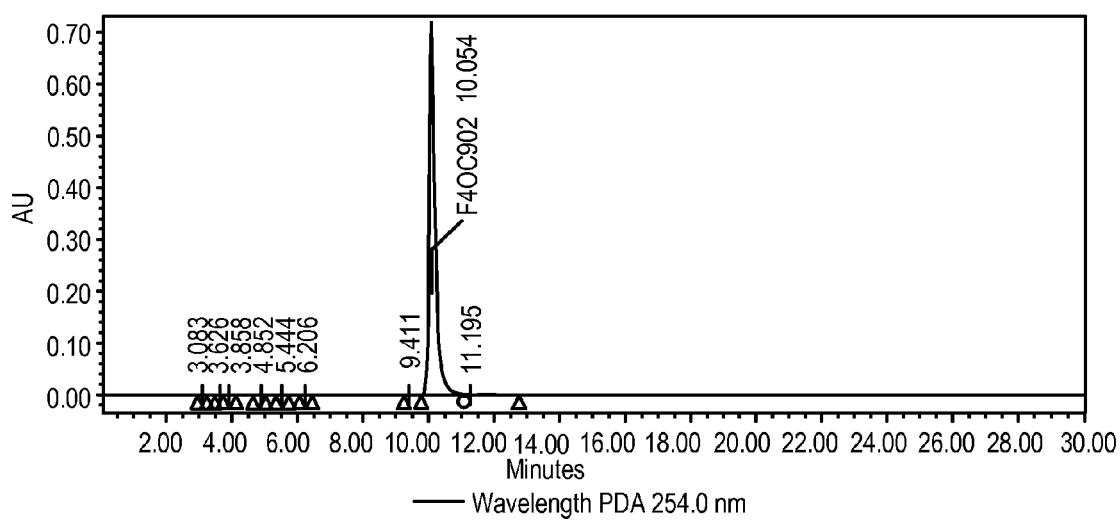
FIG. 4 is an HPLC trace of N-Fmoc-(S)-alpha-methyl-alpha-amino-6-enoic acid with the detector set to 254 nm.
Figure 5:
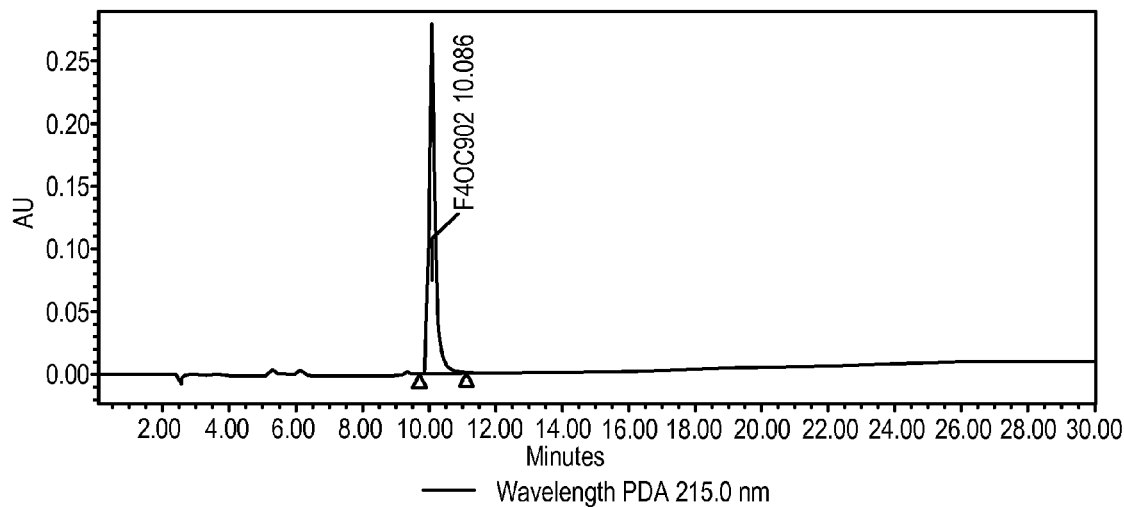
FIG. 5 is an HPLC trace of an N-Fmoc-(S)-alpha-methyl-alpha-amino-6-enoic acid standard.
Figure 6:
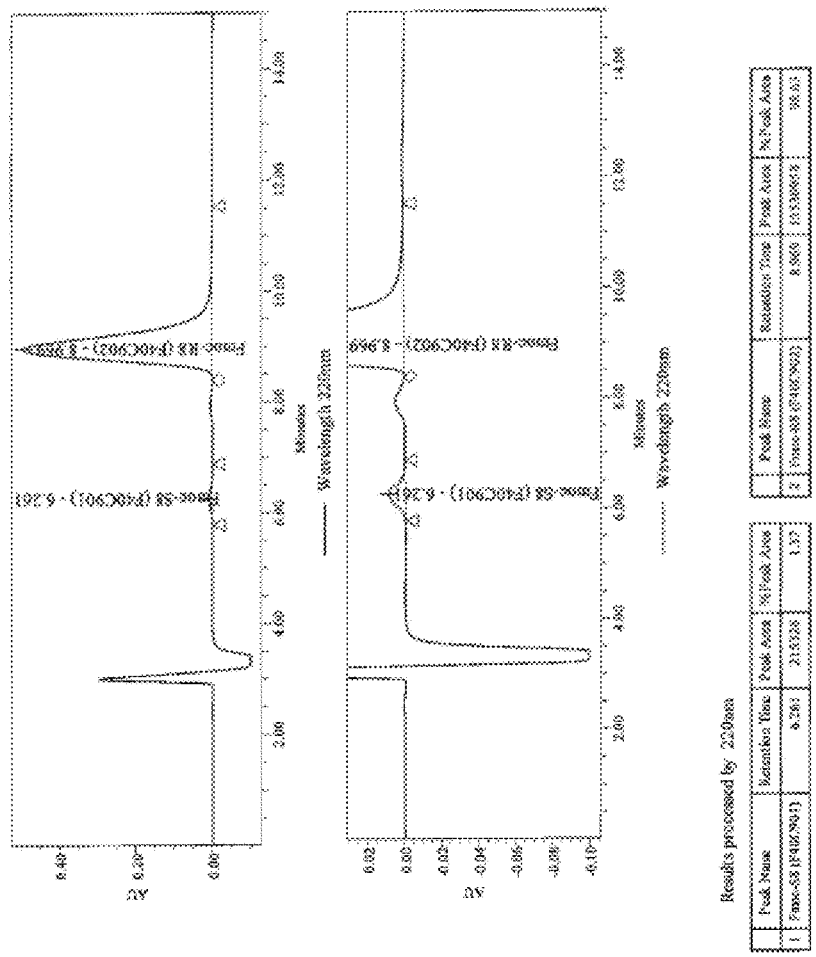
FIG. 6 is a chiral HPLC trace of N-Fmoc-(R)-alpha-methyl-alpha-aminodec-9-enoic acid.
Figure 7:
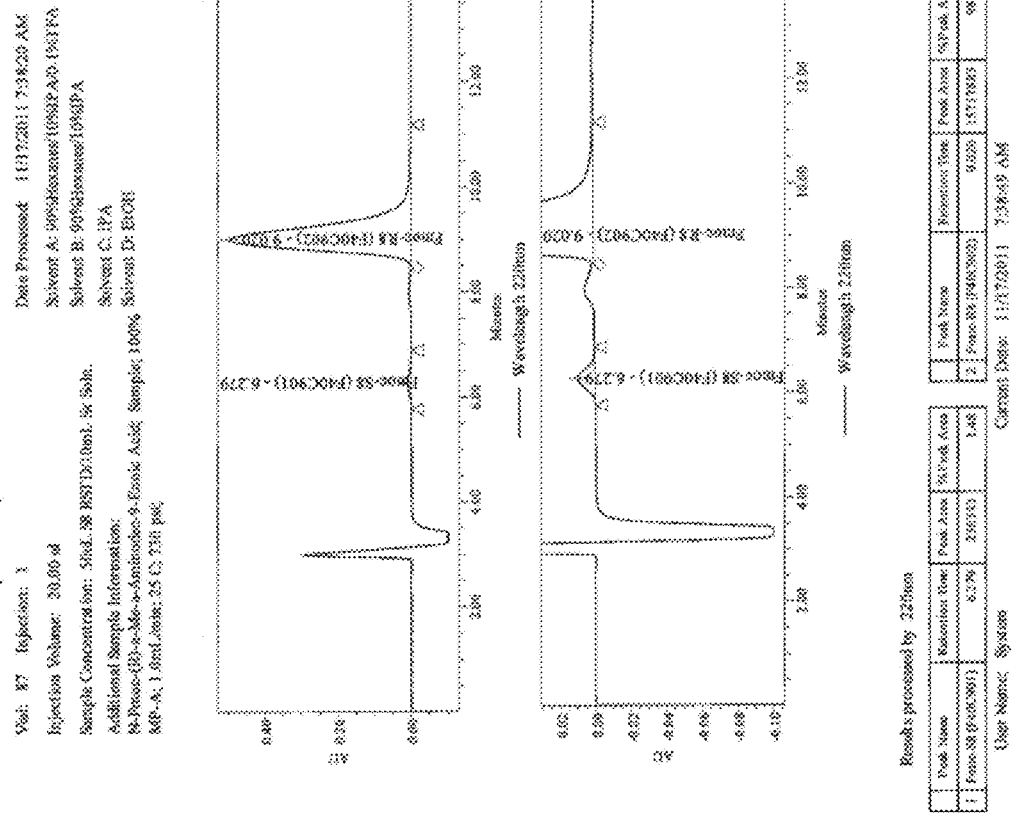
FIG. 7 is a chiral HPLC trace of N-Fmoc-(R)-alpha-methyl-alpha-aminodec-9-enoic acid spiked with N-Fmoc-(S)-alpha-methyl-alpha-aminodec-9-enoic acid.
Figure 8:
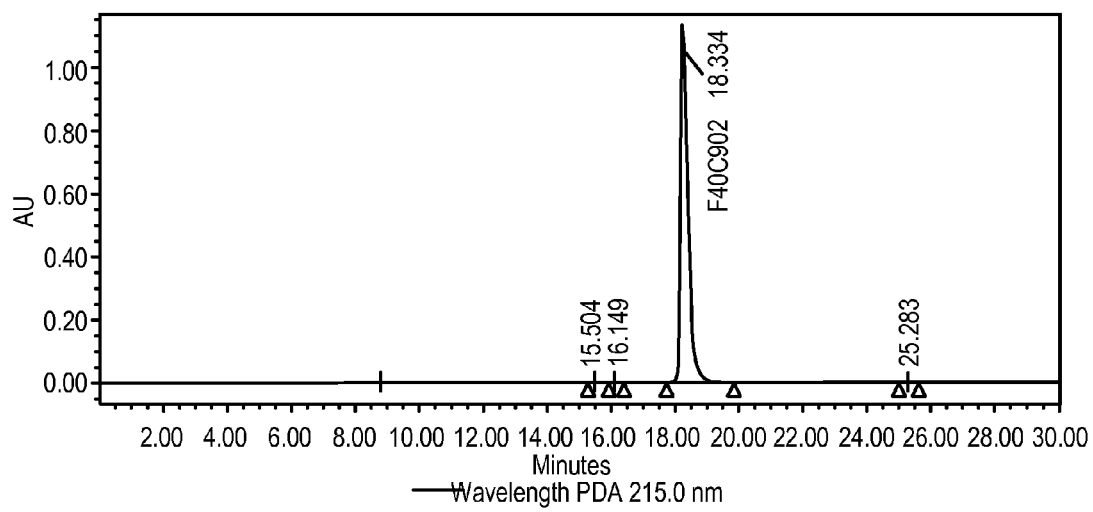
FIG. 8 is an HPLC trace of N-Fmoc-(R)-alpha-methyl-alpha-aminodec-9-enoic acid with the detector set to 215 nm.
Figure 9:
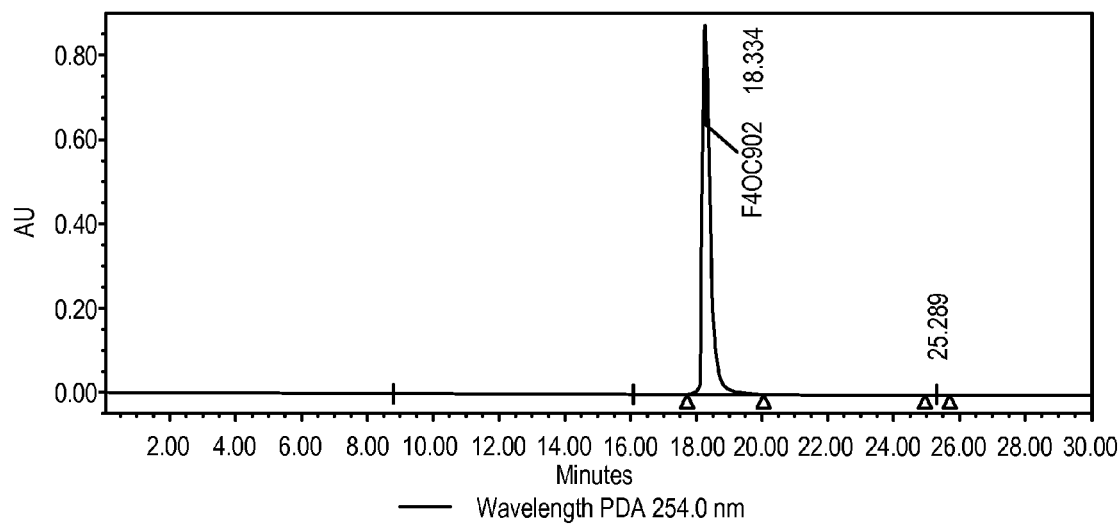
FIG. 9 is an HPLC trace of N-Fmoc-(R)-alpha-methyl-alpha-aminodec-9-enoic acid with the detector set to 254 nm.

All publications, patents, and patent applications referenced herein are incorporated by reference in their entireties. In the event of a conflict between a term herein and a term incorporated by reference, the term herein controls.

DETAILED DESCRIPTION OF THE INVENTION

The details of one or more inventive embodiments are set forth in the accompanying drawings, the claims, and in the description herein. Other features, objects, and advantages of inventive embodiments disclosed and contemplated herein will be apparent from the description and drawings, and from the claims.

INITIAL DEFINITIONS

As used herein, unless otherwise indicated, the article "a" means one or more unless explicitly otherwise provided for.

As used herein, unless otherwise indicated, terms such as "contain," "containing," "include," "including," and the like mean "comprising."

As used herein, unless otherwise indicated, the term "or" can be conjunctive or disjunctive.

Herein, unless otherwise indicated, any embodiment can be combined with any other embodiment.

Herein, unless otherwise indicated, some inventive embodiments herein contemplate numerical ranges.

When ranges are present, the ranges include the range endpoints. Additionally, every subrange and value within the range is present as if explicitly written out.

Herein, unless otherwise indicated, the symbol "D" stands for deuterium or a radical thereof.

Herein, unless otherwise indicated, the term "halo" or the term "halogen" each refer to fluorine, chlorine, bromine or iodine, or a radical thereof.

Herein, unless otherwise indicated, the term "alkyl" refers to a hydrocarbon chain that is a straight chain or branched chain, containing the indicated number of carbon atoms. For example, $C_1$-$C_3$ alkyl group indicates that the group has from 1 to 3 (inclusive) carbon atoms in it.

"Deuteroalkyl" refers to a deuterated alkyl chain, where the alkyl chain hydrogen atoms are replaced at least the 90% level with deuterium atoms.

Herein, unless otherwise indicated, the term "haloalkyl" refers to a halogenated alkyl chain where the alkyl chain hydrogen atoms are replaced with halogen atoms. In some embodiments, the halogen atoms are all the same (e.g., all F or all Cl).

Herein, unless otherwise indicated, ⫽ is a double (e.g., alkene) bond.

As used herein, unless otherwise indicated, the term "peptidomimetic macrocycle" or "crosslinked polypeptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycles include embodiments where the macrocycle-forming linker connects an α-carbon of the first amino acid residue (or analog) to the α-carbon of the second amino acid residue (or analog) in the peptide. Peptidomimetic macrocycles include one or more non-peptide bonds between one or more amino acid residues and/or amino acid analog residues, and optionally include one or more non-naturally-occurring amino acid residues or amino acid analog residues in addition to any which form the macrocycle.

As used herein, unless otherwise indicated, a "corresponding uncrosslinked polypeptide" when referred to in the context of a peptidomimetic macrocycle is understood to relate to a polypeptide of the same length as the macrocycle and comprising the equivalent natural amino acids of the wild-type sequence corresponding to the macrocycle.

As used herein, unless otherwise indicated, the term "amino acid" refers to a molecule containing both an amino group and a carboxyl group. Suitable amino acids include, for example, both the D- and L-isomers of the naturally-occurring amino acids, as well as non-naturally occurring amino acids prepared by organic synthesis or other metabolic routes. The term amino acid contemplates, for example, α-amino acids, natural amino acids, non-natural amino acids, and amino acid analogs.

As used herein, unless otherwise indicated, the term "α-amino acid" refers to a molecule containing both an amino group and a carboxyl group bound to a carbon atom which is designated the α-carbon atom.

As used herein, unless otherwise indicated, the term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

Herein, unless otherwise indicated, the term "amino acid side chain" refers to a moiety attached to the α-carbon atom (or another backbone atom) in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an α,α di-substituted amino acid).

Herein, unless otherwise indicated, the term "α,αdi-substituted amino" acid refers to a molecule or moiety containing both an amino group and a carboxyl group bound to a carbon atom (e.g., the α-carbon atom) that is also attached a natural and non-natural, to two natural, or to two non-natural amino acid side chains.

Herein, unless otherwise indicated, the term "polypeptide" can encompass two or more naturally or non-naturally-occurring amino acids joined by a covalent bond (e.g., an amide bond). Polypeptides, as described herein can include full length proteins (e.g., fully processed proteins) as well as shorter amino acid sequences (e.g., fragments of naturally-occurring proteins or synthetic polypeptide fragments).

Herein, unless otherwise indicated, the term "macrocyclization reagent" or "macrocycle-forming reagent" can refer to any reagent which can be used to prepare a peptidomimetic macrocycle by mediating the reaction between two reactive olefinic groups thereon. The reactive groups that, once reacted, close the linker, can be for example terminal olefins (alkenes), deuterated or non-deuterated.

Macrocyclization reagents or macrocycle-forming reagents can be metathesis catalysts including, but not limited to, stabilized, late transition metal carbene complex catalysts such as Group VIII transition metal carbene catalysts. For example, such catalysts can contain Ru and Os metal centers having a +2 oxidation state, an electron count of 16 and pentacoordinated. The catalysts can have W or Mo centers. Various catalysts are disclosed in Grubbs et al., "Ring Closing Metathesis and Related Processes in Organic Synthesis" *Acc. Chem. Res.* 1995, 28, 446-452; U.S. Pat. No. 5,811,515; U.S. Pat. No. 7,932,397; U.S. Pat. Application Pub. No. 2011/0065915; U.S. Pat. Application Pub. No. 2011/0245477; Yu et al., "Synthesis of Macrocyclic Natural Products by Catalyst-Controlled Stereoselective Ring-Closing Metathesis," *Nature* 2011, 479, 88; and Peryshkov et al., "Z-Selective Olefin Metathesis Reactions Promoted by Tungsten Oxo Alkylidene Complexes," *J. Am. Chem. Soc.* 2011, 133, 20754.

Herein, unless otherwise indicated, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

Provided herein are crystalline compounds of Formula (I) or their crystalline salts:

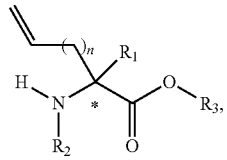

Formula (I)

wherein $R_1$ is $C_1$-$C_3$ alkyl, $C_1$-$C_3$ deuteroalkyl, or $C_1$-$C_3$ haloalkyl; * is a stereocenter; n is an integer from 1 to 20; $R_2$ is —H or a nitrogen protecting group; and $R_3$ is —H or a protecting or activating group.

$R_1$

In the crystalline compound of Formula (I) or its crystalline salt, $R_1$ can be $C_1$-$C_3$ alkyl. $R_1$ can be, for example, methyl, ethyl, n-propyl, or isopropyl.

In the crystalline compound of Formula (I) or its crystalline salt, $R_1$ can be $C_1$-$C_3$ deuteroalkyl. $R_1$ can be, for example, —$CD_3$, —$CD_2CD_3$, —$CD_2CD_2CD_3$, or —$CD(CD_3)_2$.

In the crystalline compound of Formula (I) or its crystalline salt, $R_1$ can be $C_1$-$C_3$ haloalkyl. The halogen can be, for example, —F, —Cl, —Br, or —I. $R_1$ can be, for example, —$CX_3$, —$CX_2CX_3$, —$CX_2CX_2CX_3$, or —$CX(CX_3)_2$, wherein X is a halogen.

$R_2$

In the crystalline compound of Formula (I) or its crystalline salt, $R_2$ can be, for example, —H, or a nitrogen protecting group selected from the group consisting of: 9-Fluorenylmethoxycarbonyl (Fmoc), Trityl (Trt), 4-Methoxytrityl (Mmt), 2-(3,5-Dimethoxyphenyl)propan-2-yloxycarbonyl (Ddz), 2-(p-Biphenylyl)-2-propyloxycarbonyl (Bpoc), 2-(4-Nitrophenylsulfonyl)ethoxycarbonyl (NSC), (1,1-Dioxobenzo[b]thiophene-2-yl)methyloxycarbonyl (Bsmoc), (1,1-Dioxonaphtho[1,2-b]thiophene-2-yl)methyloxycarbonyl (α-Nsmoc), 1-(4,4-dimethyl-2,6-dioxocyclohex-1-ylidene)-3-methylbutyl (ivDde), 2,-Di-tert-butyl-Fmoc (Fmoc*), 2-Fluoro-Fmoc (Fmoc(2F)), 2-Monoisooctyl-Fmoc (mio-Fmoc), 2,7-Diisooctyl-Fmoc (dio-Fmoc), 2-[Phenyl(methyl)sulfonio]ethyloxy carbonyl tetrafluoroborate (Pms), Ethanesulfonylethoxycarbonyl (Esc), 2-(4-Sulfophynylsulfonyl)ethoxy carbonyl (Sps), Tert-butyloxycarbonyl (Boc), Benzyloxycarbonyl (Z), Allyloxycarbonyl (Alloc), 2,2,2-Trichloroethyloxycarbonyl (Troc), p-Nitrobenzyloxycarbonyl (pNZ), Propargyloxycarbonyl (Poc), o-Nitrobenzenesulfonyl (oNBS), 2,4-Dinitrobenzenesulfonyl (dNBS), Benzothiazole-2-sulfonyl (Bts), o-Nitrobenzyloxycarbonyl (oNz), 4-Nitroveratryloxycarbonyl (NVCO), 2-(2-Nitrophenyl)propyloxycarbonyl (NPPOC), 2,(3,4-Methylethenedioxy-6-nitrophenyl)propyloxycarbonyl (MNPPOC), 9-(4-Bromophenyl)-9-fluorenyl (BrPhF), Azidomethoxycarbonyl (Azoc), Hexafluoroacetone (HFA), 2-Chlorobenzyloxycarbonyl (Cl-Z), 4-Methyltrityl (Mtt), Trifluoroacetyl (tfa), (Methylsulfonyl)ethoxycarbonyl (Msc), Phenyldisulphanylethyloxycarbonyl (Phdec), 2-Pyridyldisulphanylethyloxycarbonyl (Pydec), and o-Nitrobenzenesulfonyl (O-NBS).

Nitrogen protecting groups can be found, for example, in Isidro-Llobet, A., et al., "Amino Acid-Protecting Groups," *Chem. Rev.* 2455-2504 (2009).

In the crystalline compound of Formula (I) or its crystalline salt, $R_2$ can be, for example, a nitrogen protecting group selected from the group consisting of 9-Fluorenylmethoxycarbonyl (Fmoc), Trityl (Trt), 4-Methoxytrityl (Mmt), 2-(3,5-dimethoxyphenyl)propan-2-yloxycarbonyl (Ddz), 2-(p-biphenylyl)-2-propyloxycarbonyl (Bpoc), 2-(4-Nitrophenylsulfonyl)ethoxycarbonyl (NSC), 1,1-Dioxobenzo[b]thiophene-2-yl)methyloxycarbonyl (Bsmoc), 1-(4,4-dimethyl-2,6-dioxocyclohex-1-ylidene)-3-methylbutyl (ivDde), Tert-butyloxycarbonyl (Boc), Benzyloxycarbonyl (Z), Allyloxycarbonyl (Alloc), 2,2,2-Trichloroethyloxycarbonyl (Troc), p-Nitrobenzyloxycarbonyl (pNZ), o-Nitrobenzenesulfonyl (oNBS), 2,4-Dinitrobenzenesulfonyl (dNBS), o-Nitrobenzyloxycarbonyl (oNz), 4-Nitroveratryloxycarbonyl (NVCO), 2-(2-Nitrophenyl)propyloxycarbonyl (NPPOC), Hexafluoroacetone (HFA), 2-Chlorobenzyloxycarbonyl (Cl-Z), 4-Methyltrityl (Mtt), Trifluoroacetyl (tfa), (Methylsulfonyl)ethoxycarbonyl (Msc), and o-Nitrobenzenesulfonyl (O-NBS).

In the crystalline compound of Formula (I) or its crystalline salt, $R_2$ can be a nitrogen protecting group selected from the group consisting of 9-Fluorenylmethoxycarbonyl (Fmoc), Trityl (Trt), 4-Methoxytrityl (Mmt), 2-(3,5-dimethoxyphenyl)propan-2-yloxycarbonyl (Ddz), 2-(p-biphenylyl)-2-propyloxycarbonyl (Bpoc), Tert-butyloxycarbonyl (Boc), Benzyloxycarbonyl (Z), Allyloxycarbonyl (Alloc), 2,2,2-Trichloroethyloxycarbonyl (Troc), o-Nitrobenzenesulfonyl (oNBS), Trityl (Trt), 4-Methyltrityl (Mtt), and o-Nitrobenzenesulfonyl (O-NBS).

In the crystalline compound of Formula (I) or its crystalline salt, $R_2$ can be, for example, the nitrogen protecting group 9-Fluorenylmethoxycarbonyl (Fmoc).

$R_3$

In the crystalline compound of Formula (I) or its crystalline salt, $R_3$ can be, for example, —H or a protecting or activating group selected from the group consisting of: tert-Butyl (tBu), 2-Chlorotrityl (2-Cl-Trt), 2,4-Dimethoxybenzyl (DMB), Benzyl (Bn), 2-Phenylisopropyl (2-PhiPr), 5-Phenyl-3,4-ethylenedioxythenyl, 9-Fluorenylmethyl (Fm), 4-(N-[1-(4,4-dimethyl-2,6-dioxocyclohexylidene)-3-methylbutyl]-amino)benzyl (Dmab), Methyl (Me), Ethyl (Et), Carbamoylmethyl (Cam), Allyl (Al), Phenacyl (Pac), p-Nitrobenzyl (pNB), 2-Trimethylsilylethyl (TMSE), (2-Phenyl-2-trimethylsilyl)ethyl (PTMSE), 2-(Trimethylsilyl)isopropyl (Tmsi), Trimethylsilyl (TMS), 2,2,2-Trichloroethyl (Tce), p-Hydroxyphenacyl (pHP), 4,5-Dimethoxy-2-nitrobenzyl (Dmnb), 1,1-Dimethylallyl (Dma), Pentaamine cobalt (III), Succinimide, p-Nitrophenyl, Pentafluorophenyl, and 2,4,5-trichlorophenyl.

In the crystalline compound of Formula (I) or its crystalline salt, $R_3$ can be, for example —H.

n

In the crystalline compound of Formula (I) or its crystalline salt, n can range, for example, from 1-20, from 3-11, or from 3-6. n can be, for example 3 or 6 or 11. n can be 3. n can be 6. n can be 11.

*

In the crystalline compound of Formula (I) or its crystalline salt, the stereocenter * can be (R). In the crystalline compound of Formula (I) or its crystalline salt, the stereocenter * can be (S).

In one embodiment, in the crystalline compound of Formula (I) or it crystalline salt, $R_1$ can be $C_1$-$C_3$ alkyl; $R_2$ can be 9-Fluorenylmethoxycarbonyl (Fmoc); $R_3$ can be selected from the group consisting of —H tert-Butyl (tBu), 2-Chlorotrityl (2-Cl-Trt), 2,4-Dimethoxybenzyl (DMB), Benzyl (Bn), 2-Phenylisopropyl (2-PhiPr), 5-Phenyl-3,4-ethylenedioxythenyl, 9-Fluorenylmethyl (Fm), 4-(N-[1-(4,4-dimethyl-2,6-dioxocyclohexylidene)-3-methylbutyl]-amino)benzyl (Dmab), Methyl (Me), Ethyl (Et), Carbamoylmethyl (Cam), Allyl (Al), Phenacyl (Pac), p-Nitrobenzyl (pNB), 2-Trimethylsilylethyl (TMSE), (2-Phenyl-2-trimethylsilyl)ethyl (PTMSE), 2-(Trimethylsilyl)isopropyl (Tmsi), Trimethylsilyl (TMS), 2,2,2-Trichloroethyl (Tce), p-Hydroxyphenacyl (pHP), 4,5-Dimethoxy-2-nitrobenzyl (Dmnb), 1,1-Dimethylallyl (Dma), Pentaamine cobalt (III), Succinimide, p-Nitrophenyl, Pentafluorophenyl, and 2,4,5-trichlorophenyl; n can be an integer ranging from 3 to 11; and the stereocenter * can be (R).

In one embodiment, in the crystalline compound of Formula (I) or it crystalline salt, $R_1$ can be $C_1$-$C_3$ alkyl; $R_2$ can be 9-Fluorenylmethoxycarbonyl (Fmoc); $R_3$ can be selected from the group consisting of —H tert-Butyl (tBu), 2-Chlorotrityl (2-cl-Trt), 2,4-Dimethoxybenzyl (DMB), Benzyl (Bn), 2-Phenylisopropyl (2-PhiPr), 5-Phenyl-3,4-ethylenedioxythenyl, 9-Fluorenylmethyl (Fm), 4-(N-[1-(4,4-dimethyl-2,6-dioxocyclohexylidene)-3-methylbutyl]-amino)benzyl (Dmab), Methyl (Me), Ethyl (Et), Carbamoylmethyl (Cam), Allyl (Al), Phenacyl (Pac), p-Nitrobenzyl (pNB), 2-Trimethylsilylethyl (TMSE), (2-Phenyl-2-trimethylsilyl)ethyl (PTMSE), 2-(Trimethylsilyl)isopropyl (Tmsi), Trimethylsilyl (TMS), 2,2,2-Trichloroethyl (Tce), p-Hydroxyphenacyl (pHP), 4,5-Dimethoxy-2-nitrobenzyl (Dmnb), 1,1-Dimethylallyl (Dma), Pentaamine cobalt (III), Succinimide, p-Nitrophenyl, Pentafluorophenyl, and 2,4,5-trichlorophenyl; n can be an integer ranging from 3 to 11; and the stereocenter * can be (S).

In one embodiment, in the crystalline compound of Formula (I) or its crystalline salt, $R_1$ can be methyl, $R_2$ can be 9-Fluorenylmethoxycarbonyl (Fmoc); $R_3$ can be —H, n can be 3, 6, or 11, and the stereocenter * can be (R).

In one embodiment, in the crystalline compound of Formula (I) or its crystalline salt, $R_1$ can be methyl, $R_2$ can be 9-Fluorenylmethoxycarbonyl (Fmoc); $R_3$ can be —H, n can be 3, 6, or 11, and the stereocenter * can be (S).

Chemical Purity

Herein, unless otherwise indicated, any compound, its salt, crystalline compound, or crystalline salt of a compound, can have a chemical purity. Chemical purity can be defined, for example, as the degree to which a substance is undiluted or unmixed with extraneous material, and can be typically expressed as a percentage. Any compound, salt thereof, crystalline compound, or crystalline salt of a compound herein can have, for example, a chemical purity ranging from about 90% to 100%. The chemical purity can be, for example, about 92% to 100%, about 94% to 100%, about 96% to 100%, about 98% to 100%, about 90%, about 91%, about 92%, about 93%, about 94%, about 95%, about 96%, about 97%, about 98%, about 99%, or about 100%. The percentage can be, for example, based on the total weight of the compound, its salt, crystalline compound, or its salt. The percentage can be, for example, arrived at using HPLC. The percentage can be arrived at, for example, using NMR, for example proton NMR. The chemical purity can be arrived at, for example, using elemental analysis.

Enantiomeric Excess

Herein, unless otherwise indicated, any compound, salt thereof, crystalline compound, or crystalline salt of a compound, can have an enantiomeric excess. The enantiomeric excess can be, for example, from about 80% to 100%, from about 85% to 100%, from about 90% to 100%, from about 95% to 100%, from about 96% to 100%, from about 97% to 100%, from about 98% to 100%, from about 99% to 100%, about 95%, about 96%, about 97%, about 97.2%, about 98%, about 99%, or 100%. The enantiomeric excess can be, for example, greater than 95%, greater than 96%, greater than 97%, greater than 98%, or greater than 99%. Herein, unless otherwise indicated, enantiomeric excess can be calculated, for example, by the formula: enantiomeric excess (ee)=((P−S)/(P+S))×100%, where P and S represent the moles, respectively, of the predominant and subdominant enantiomer produced or present in a sample. For example, if the more moles of the (R) enantiomer are produced at than moles of the (S) enantiomer, moles of (R) enantiomer are designated as R, and moles of the (S) enantiomer are designated as S, then the enantiomeric excess formula becomes: ee (%)=((R−S)/(R+S))×100%. Herein, unless otherwise indicated, the amount (e.g., moles) or enantiomer produced can be determined, for example, by chiral HPLC, by chiral GC, or via a chiral NMR shift reagent using NMR spectroscopy.

Optical Purity

Herein, unless otherwise indicated, any compound, its salt, crystalline compound, or crystalline salt of a compound, can have an optical purity. The optical purity can be, for example, from about 80% to 100%, from about 85% to 100%, from about 90% to 100%, from about 95% to 100%, about 95%, about 96%, about 97%, about 98%, about 99%, or 100%. Herein, unless otherwise indicated, optical purity can be calculated using the formula: optical purity (%)= (Mobserved/Mmaximal)*100%, where [α]observed is the specific rotation of the sample, and [α]maximal is the specific rotation of the pure enantiomer. Herein, unless otherwise indicated, specific rotation can be defined as the observed angle of optical rotation, a, when plane-polarized light is passed through a sample with a path length of 1 decimeter and a sample concentration of 1 gram per 1 milliliter. The specific rotation can be obtained, for example, at 20° C. and at a wavelength of light of 589 nanometers (e.g., the sodium D line). Herein, unless otherwise indicated, the specific rotation can be obtained, for example, with a polarimeter. Herein, unless otherwise indicated, the solvent the sample is dissolved in can be any suitable solvent or solvent combination, for example, ethanol, methanol, chloroform, dichloromethane, carbon tetrachloride, water, DMSO, N,N-DMF, diethyl ether, tetrahydrofuran, hexane, pentane, acetone, or any combination thereof.

Diastereomeric Excess

Herein, unless otherwise indicated, the compounds, salts, crystalline compounds, or crystalline salts of compounds herein can be diastereomers. When this is so, the compounds, crystalline compounds, or crystalline salts of compounds herein can have a diastereomeric excess of, for example, from about 80% to 100%, from about 85% to 100%, from about 90% to 100%, from about 95% to 100%, about 95%, about 96%, about 97%, about 98%, about 99%, or 100%. Herein, unless otherwise indicated, the diastereomeric excess, for example, in a mixture of two diastereomers, can be calculated, for example, by the formula: diastereomeric excess de %=((D1−D2)/(D1+D2))*100%, wherein D1 represents, for example, the mole or percent weight of a first and most abundant diastereomer, and D2 represents for example, the mole or percent weight of a second and least abundant diastereomer, where mole percent is used consistently (e.g., alone) in the calculation, or where percent weight is used consistently (e.g., alone) in the calculation.

Converted Enantiomeric Excess or Optical Purity

Unless otherwise indicated, any compound, salt thereof, crystalline compound, or crystalline salt thereof, herein, that is a diastereomer, can be converted to an enantiomer or enantiomeric mixture having one stereocenter (e.g., * in Formula (I)) by, for example, removal of a nitrogen protecting group (e.g., removal of the nitrogen protecting group $R_2$ in the crystalline compound of Formula (I) or its crystalline salt that, together with the stereocenter *, creates a diastereomer), and the resulting enantiomer or enantiomeric mixture can then have its enantiomeric excess or optical purity determined as described herein. The resulting enantiomeric excess or optical purity, in these circumstances, is termed a converted enantiomeric excess or converted optical purity. The converted enantiomeric excess can be, for example, from about 80% to 100%, from about 85% to 100%, from about 90% to 100%, from about 95% to 100%, from about 96% to 100%, from about 97% to 100%, from about 98% to 100%, from about 99% to 100%, about 95%, about 96%, about 97%, about 97.2%, about 98%, about 99%, or 100%. The converted enantiomeric excess can be, for example, greater than 95%, greater than 96%, greater than 97%, greater than 98%, or greater than 99%. The converted optical purity can be, for example, from about 80% to 100%, from about 85% to 100%, from about 90% to 100%, from about 95% to 100%, about 95%, about 96%, about 97%, about 98%, about 99%, or 100%. Thus, any optionally crystalline diastereomer or its optionally crystalline salt herein, unless otherwise indicated, can have a converted enantiomeric excess or converted optical purity.

Specifically Exemplified Crystalline Compounds and Crystalline Salts Thereof

Herein, unless otherwise indicated, the crystalline compound of Formula (I) or its crystalline salt can be a compound of Formula (IIa) or its crystalline salt:

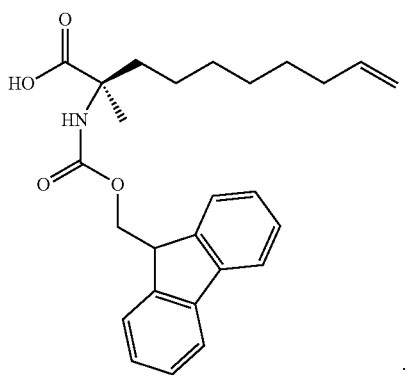

(IIa)

Herein, unless otherwise indicated, the crystalline compound of Formula (I) or its crystalline salt can be a compound of Formula (IIb) or its crystalline salt:

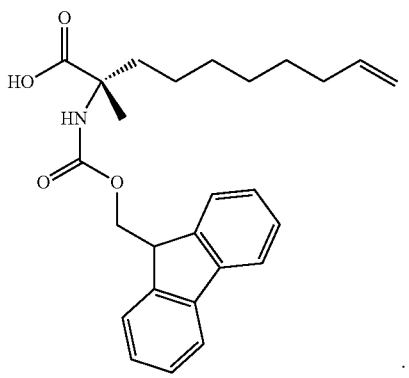

(IIb)

Herein, unless otherwise indicated, the crystalline compound of Formula (I) or its crystalline salt can be a compound of Formula (IIIa) or its crystalline salt:

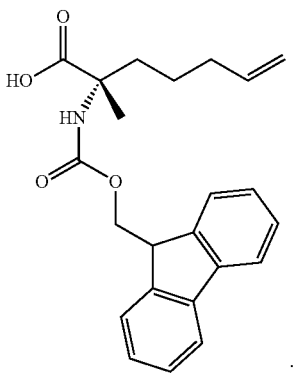

(IIIa)

Herein, unless otherwise indicated, the crystalline compound of Formula (I) or its crystalline salt can be a compound of Formula (IIIb) or its crystalline salt:

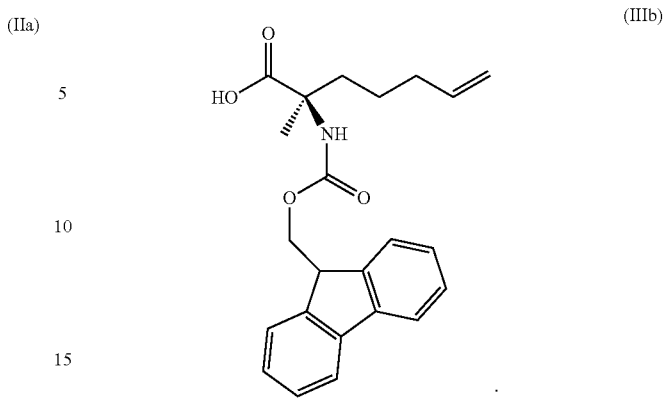

(IIIb)

Deuterated and Halogenated Compounds and their Salts

Also provided herein, unless otherwise indicated, are optionally crystalline compounds and their optionally crystalline salts of Formula (IV):

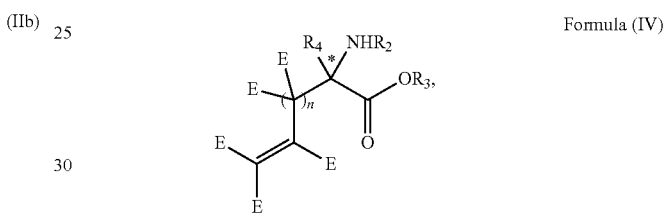

Formula (IV)

wherein $R_2$, $R_3$, n, and * are the same as in the crystalline compound or its crystalline salt of Formula (I), each E is independently selected from the group consisting of deuterium and halogen, and $R_4$ is selected from the group consisting of $C_1$-$C_3$ alkyl, $C_1$-$C_3$ deuteroalkyl and $C_1$-$C_3$ haloalkyl.

Deuterium

Herein, unless otherwise indicated, for any deuterated: compound, its salt, crystalline compound, or its crystalline salt; greater than 90%, greater than 92%, greater than 94%, greater than 96%, or greater than 98%, of the deuterated: compound, its salt, crystalline compound, or its crystalline salt; has a deuterium atom at each position designated as deuterium (D) in the deuterated: compound, its salt, the crystalline compound, or its crystalline salt.

Methods of Making

The compounds and their salts herein can be advantageously made by methods disclosed herein that result in at least one of the following advantages:

- the compounds or their salts that are produced are crystalline;
- the compounds and their salts (both of which can be crystalline) are advantageously produced in high yield;
- the compounds and their salts (both of which can be crystalline) are advantageously produced in high chemical purities;
- the compounds and their salts (both of which can be crystalline) are advantageously produced in high enantiomeric excess, optical purity, diastereomeric excess, high converted enantiomeric excess, or high converted optical purity; or
- the compounds and their salts (both of which can be crystalline) are produced without chromatographic purification (e.g., without chromatography).

Unless otherwise indicated, the compounds, their salts, crystalline compounds, and their crystalline salts, herein can be produced using for example exemplary Scheme I (with modifications that would be readily apparent to a skilled artisan). Scheme I depicts formation of the crystalline N-Fmoc-(R)-α-methyl-α-aminodec-9-enoic acid (i.e., the crystalline compound of Formula (IIa)). Sequence I starts with Boc-D-proline (i.e., the compound of Formula (V)). It is understood that by starting with Boc-L-proline, compounds with the opposite stereochemistry of the compound of Formula (IIa) can be produced (e.g., the compound of Formula (IIb) can be produced). It is also understood that the stereochemisty of the amino acid used to form the metal complex (e.g., alanine used to form the metal complex of Formula (XI) in Scheme I) is not dispositive of the stereochemistry in the resulting crystalline compound (e.g., of Formula (IIa)) or its crystalline salt.

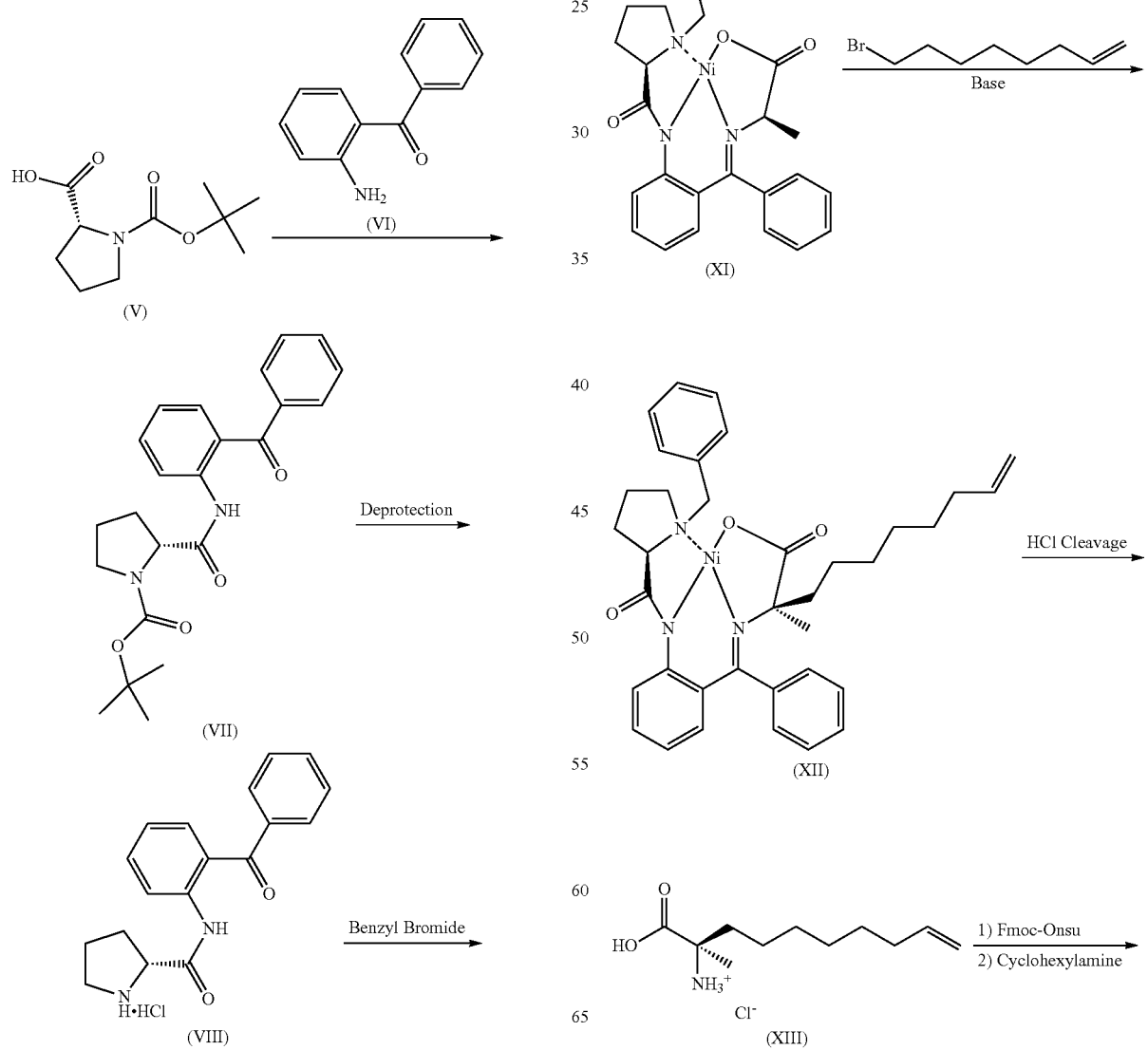

-continued

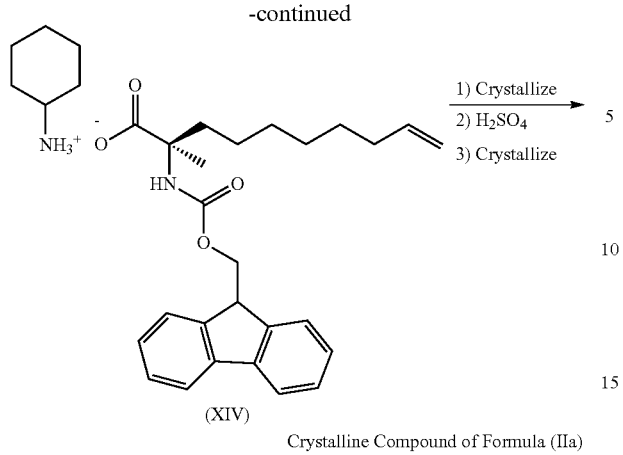

(XIV)

Crystalline Compound of Formula (IIa)

In Scheme I, Boc-D-proline (Compound of Formula (V)) is first reacted with 2-aminobenzophenone (compound of Formula (VI)) to form the compound of Formula (VII). Next, the compound of Formula (VII) is deprotected to form the HCl salt of the compound of Formula (VIII). A skilled artisan would readily understand that the synthetic scheme contemplates use of acids other than HCl, including organic acids and inorganic acids, for example, nitric acid, phosphoric acid, sulfuric acid, boric acid, hydrofloric acid, hydrobromic acid, and perchloric acid.

The salt of the compound of Formula (VIII) is next reacted with benzyl bromide, and for example, a base, to form the compound of Formula (IX). A skilled artisan would readily understand that substituted benzyl halides could be employed in place of benzyl bromide. For example, the following benzyl halides, where X=Cl, Br, or I, could be employed:

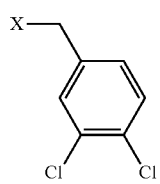
(X$_a$)

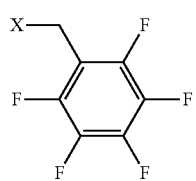
(X$_b$)

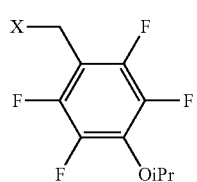
(X$_c$)

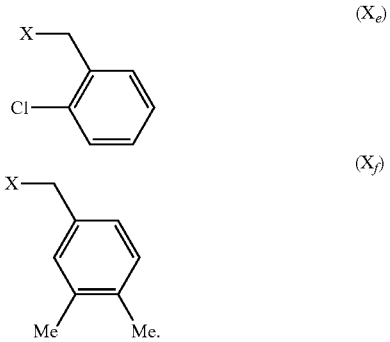

Representative benzyl halides are found in Belokon, Y. N., et al., "Halo-substituted (S)—N-(2-benzoylphenyl)-1-benzylpyrrolidine-2-carboxamides as new chiral auxiliaries for the asymmetric synthesis of (S)-α-amino acids,"*Russian Chemical Bulletin, International Edition*, 51(8): 1593-1599 (2002). Further and different benzyl halides could also be employed:

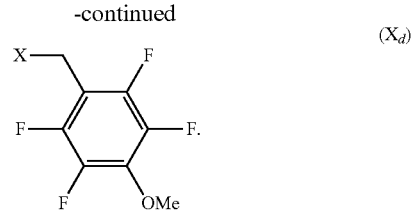

These representative benzyl halides are found in Saghiyan, A. S., et al., "New chiral NiII complexes of Schiff's bases of glycine and alanine for efficient asymmetric synthesis of α-amino acids," *Tedrahedron: Asymmetry* 17: 455-467 (2006).

Next, the compound of Formula (IX) is reacted with L-alanine and Ni(NO$_3$)$_2$ to form the metal complex of Formula (XI). The skilled artisan would understand that other amino acids other than alanine could be employed in Scheme I. For example, glycine; 2-aminobutanoic acid, 2-aminopentanoic acid, and valine, for example in their D or L forms, could be employed. The Ni(NO$_3$)$_2$ can be a hydrate, for example, a hexahydrate. The reaction can be run in an alcoholic solvent, for example, methanol. The reaction can be run at an elevated temperature, for example, from about 40° C. to about 60° C. The reaction can be run in the presence of a base, for example, a hydroxide, for example an inorganic hydroxide, for example, potassium hydroxide. Other hydroxides are contemplated, including sodium hydroxide, cesium hydroxide, lithium hydroxide, magnesium hydroxide, and ammonium hydroxide.

To increase purity of the final product from Scheme I, the metal complex of Formula (XI) can be crystallized one or more times from one or more solvents, for example a cyclic ether and a non-cyclic ether. In one embodiment, the solvent is tetrahydrofuran and methyl tert-butyl ether. In some cases the ratio of the cyclic ether to the non-cyclic ether is at most 0.5:10, 1.0:10, 1.5:10, 2.0:10, 2.5:10, 3.0:10, 3.5:10, 4.0:10, 4.5:10 or 5:10. In other cases the ratio of the cyclic ether to the non-cyclic ether is at least 0.5:10, 1.0:10, 1.5:10, 2.0:10, 2.5:10, 3.0:10, 3.5:10, 4.0:10, 4.5:10 or 5:10. For example, some cases the metal complex of Formula (XI) is crystallized from a mixture of tetrahydrofuran and methyl tert-butyl ether in ratio of at most 0.5:10, 1.0:10, 1.5:10, 2.0:10, 2.5:10, 3.0:10, 3.5:10, 4.0:10, 4.5:10 or 5:10. In other cases the ratio of and tetrahydrofuran and methyl tert-butyl ether is at least 0.5:10, 1.0:10, 1.5:10, 2.0:10, 2.5:10, 3.0:10, 3.5:10, 4.0:10, 4.5:10 or 5:10. In some cases the ratio of tetrahydrofuran and methyl tert-butyl ether is 1.5:10. The metal complex of Formula (XI) may also be crystallized with esters, for example with ethyl acetate or isopropyl acetate. The product or crystallized product of Formula (IX) can alternatively or additionally be crystallized or recrystallized from a solvent, for example an alcohol, for example isopropyl alcohol. Other alcohols are contemplated, including methanol, ethanol, n-propanol, a butanol, n-butanol, iso-butanol, sec-butanol, and tert-butanol.

The metal complex of Formula (XI) is then alkylated with 8-bromooct-1-ene to form the alkylated metal complex of Formula (XII). The skilled artisan would understand that other alkylating agents, including other halo alkyl olefins, could be used in place of 8-bromooct-1-ene. For example, alkylating agents of the Formula (XV) could be used:

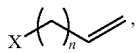
(XV)

wherein X is Cl, Br, or I, and n is an integer from 1 to 20. For example, n can be from 3 to 11, from 3 to 6, or 3 or 6. Some or all of the hydrogen atoms present in the compound of Formula (XV) can be replaced with deuterium atoms or halogen atoms. The alkylation can be performed in one or more solvents, for example a polar aprotic solvent, for example N,N-dimethyl formamide (DMF). The alkylation can be performed, for example, at a temperature of less than 20° C., for example, from less than 20° C. to 5° C., from less than 20° C. to 10° C., or at about 10° C. The skilled artisan would also understand that when glycine is used to form the metal complex, two alkylations could be performed one after the other. For example, the first alkylation could be performed using a $C_1$-$C_3$ alkane with a leaving group such as a halogen (e.g., methyl bromide, ethyl bromide, n-propyl bromide), or a $C_1$-$C_3$ deuteroalkane with a leaving group such as a halogen (e.g., $CD_3Br$, $CD_3CD_2Br$, $CD_3CD_2CD_2Br$), or a $C_1$-$C_3$ haloalkane with a leaving group such as a more reactive halogen than the other halogens in the haloalkane (e.g., $CF_3Br$, $CF_3CF_2Br$, $CF_3CF_2CF_2Br$). Then, the second alkylation could be performed using the alkylating agent of Formula (XV). The order of the first and second alkylations can be reversed.

Purification of Formula (XII) may be achieved by crystallization one or more times from one or more solvents including cyclic and non-cyclic ethers, esters, hexanes and heptanes. For example crystallization may be achieved using a combination of ethyl acetate and hexanes, ethyl acetate and heptanes, isopropyl acetate and hexanes, isopropyl acetate and heptanes, methyl tertiary-butyl ether and hexanes, methyl tertiary-butyl ether and heptanes or isopropyl acetate and methyl tertiary-butyl ether.

The metal complex of Formula (XII) is then cleaved with an acid, for example HCl, using one or more solvents, for example an ether, for example a cyclic ether, for example tetrahydrofuran, to form the amino acid HCl salt of Formula (XIII). The skilled artisan would understand that other acids in addition to HCl are contemplated, for example organic or inorganic acids, for example, nitric acid, phosphoric acid, sulfuric acid, boric acid, hydrofloric acid, hydrobromic acid, or perchloric acid. The salt of Formula (XIII) may be further purified by crystallization one or more times with one or more solvents. The solvent may be any suitable solvent including tetrahydrofuran, methyl tertiary-butyl ether, ethyl acetate, isopropyl acetate, ethanol, methanol, isopropanol, acetonitrile, or a combination thereof. In one embodiment, the solvent is acetonitrile.

The amino acid salt of Formula (XIII) is then nitrogen protected with a nitrogen protecting group, in this case an Fmoc group, and the cyclohexylamine addition salt of the protected amino acid is formed, yielding the protected amino acid cyclohexylamine salt of Formula (XIV). Formation of the salt of Formula (XIV) can be achieved in any suitable solvent including acetonitrile, methyl tertiary-butyl ether, tetrahydrofuran or a combination thereof. In one embodiment, the solvent is methyl tertiary-butyl ether. A skilled artisan would understand that other amines, for example other cyclic amines, for example cyclopropylamine, cyclobutyl amine, cyclopentylamine, cycloheptylamine, and cyclooctylamine, are contemplated. One of skill in the art would also readily understand that other nitrogen protecting groups are contemplated, for example the nitrogen protecting groups for $R_2$ in the crystalline compound of Formula (I) or its crystalline salt herein.

The protected amino acid cyclohexylamine salt of Formula (XIV) can then be crystallized from one or more ethers, for example, two ethers, for example a cyclic ether and a non cyclic ether, for example tetrahydrofuran and methyl tert-butyl ether.

The crystallized amino acid cyclohexylamine salt of Formula (XIV) is then treated with sulfuric acid, and subsequently crystallized to form the crystalline compound of Formula (IIa). The skilled artisan would understand that acids other than sulfuric acid are contemplated, for example organic or inorganic acids, for example, nitric acid, phosphoric acid, sulfuric acid, boric acid, hydrofloric acid, hydrobromic acid, or perchloric acid. The crystallization can be performed using one or more solvents, for example two solvents, for example an alkane and haloalkane, for example hexanes and chloroform. In some cases the ratio of the alkane to the haloalkane is at least 6:1, 5:1, 4:1, 3:1, 2:1, or 1:10. In some cases the ratio of the alkane to the haloalkane is at most 6:1, 5:1, 4:1, 3:1, 2:1, or 1:10. For example, the crystalline compound of Formula (IIa) may be obtained by crystallization from a mixture of hexanes and chloroform in the ratio of at least 6:1, 5:1, 4:1, 3:1, 2:1, or 1:1. The crystalised IIa may also obtained by crystallization from a mixture of hexanes and chloroform in the ratio of at most 6:1, 5:1, 4:1, 3:1, 2:1, or 1:1. In some cases the ratio of hexanes and chloroform is 3:1.

The crystallization can be performed at a temperature ranging from, for example, about −5° C. to about −20° C., about −10° C. to about −20° C., or about −15° C. to −20° C.

The skilled artisan would understand, for example, that the crystalline compound of Formula (IIa) could be further activated or protected at its carboxylic acid function with, for example, a protecting or activating group $R_3$ of the crystalline compound of Formula (I) or its crystalline salt.

Unless otherwise indicated, the compounds, their salts, crystalline compounds, and their crystalline salts, herein can be produced using exemplary Scheme II (with modifications that would be readily apparent to a skilled artisan). Scheme II depicts formation of the crystalline N-Fmoc-(S)-α-methyl-α-aminohept-6-enoic acid (i.e., the crystalline compound of Formula (IIIa)). Sequence II starts with Boc-L-Proline (i.e., the compound of Formula (Va)). It is understood that by starting with Boc-D-proline, compounds with the opposite stereochemistry of the compound of Formula (IIIa) can be produced (e.g., the compound of Formula (III) can be produced). It is also understood that the stereochemisty of the amino acid used to form the metal complex, and whose alpha carbon atom is subsequently alkylated by the haloolefin (e.g., alanine in Formula (XIa)) is not dispositive of the stereochemistry in the resulting crystalline compound (e.g., of Formula (III)) or its crystalline salt.

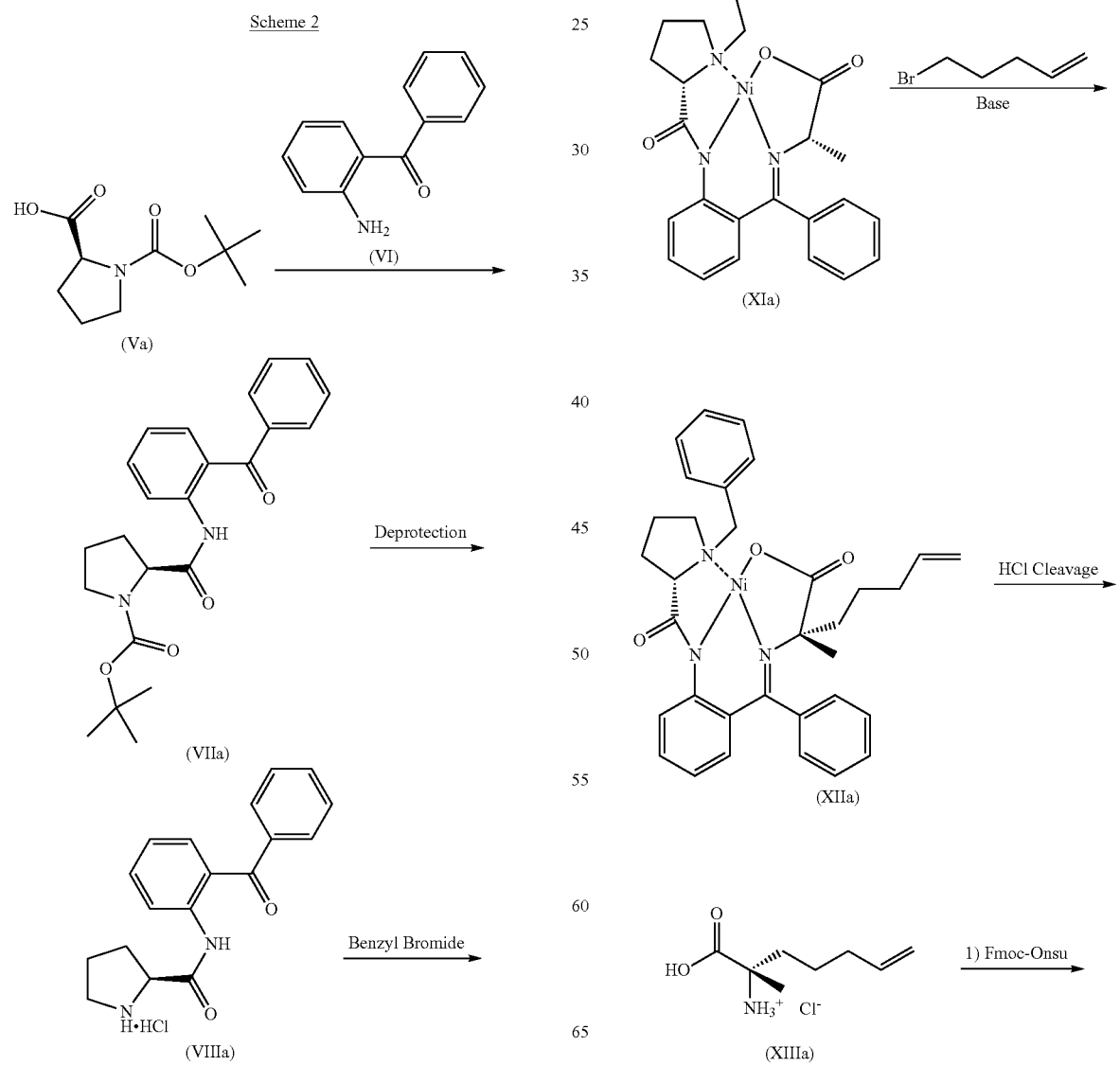

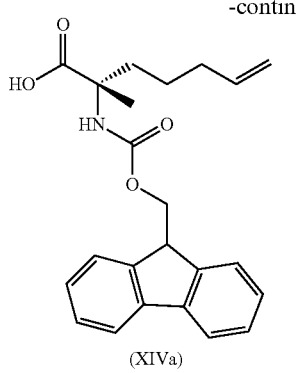

(XIVa)

In Scheme II, Boc-L-proline (Compound of Formula (Va)) is first reacted with 2-aminobenzophenone (compound of Formula (VI)) to form the compound of Formula (VIIa). Next, the compound of Formula (VIIa) is deprotected to form the HCl salt of the compound of Formula (VIIIa). A skilled artisan would readily understand that the synthetic scheme contemplates use of acids other than HCl, including organic acids and inorganic acids, for example, nitric acid, phosphoric acid, sulfuric acid, boric acid, hydrofloric acid, hydrobromic acid, and perchloric acid.

The salt of the compound of Formula (VIIIa) is next reacted with benzyl bromide, and for example a base, to form the compound of Formula (IXa). A skilled artisan would readily understand that substituted benzyl halides could be employed in place of benzyl bromide. For example, the following benzyl halides, where X=Cl, Br, or I, could be employed:

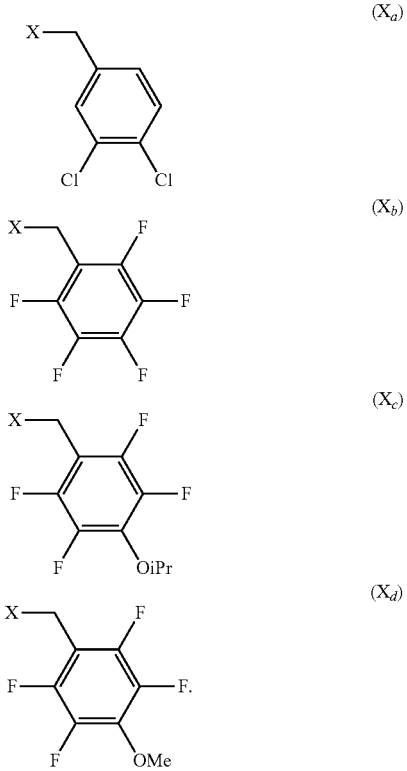

Representative benzyl halides are found in Belokon, Y. N., et al., "Halo-substituted (S)—N-(2 benzoylphenyl)-1-benzylpyrrolidine-2-carboxamides as new chiral auxiliaries for the asymmetric synthesis of (S)-α-amino acids,"*Russian Chemical Bulletin, International Edition,* 51(8): 1593-1599 (2002). Further and different benzyl halides could also be employed:

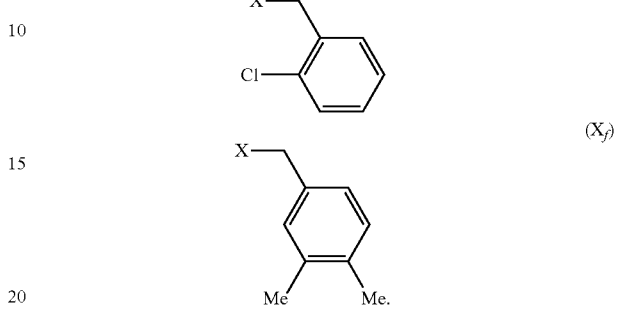

These representative benzyl halides are found in Saghiyan, A. S., et al., "New chiral NiII complexes of Schiff's bases of glycine and alanine for efficient asymmetric synthesis of α-amino acids," *Tedrahedron: Asymmetry* 17: 455-467 (2006).

Next, the compound of Formula (IXa) is reacted with L-alanine and Ni(NO$_3$)$_2$ to form the metal complex of Formula (XIa). The skilled artisan would understand that other amino acids other than alanine could be employed in Scheme II. For example, glycine; 2-aminobutanoic acid, 2-aminopentanoic acid, and valine could be employed, for example in their D or L forms. The Ni(NO$_3$)$_2$ can be a hydrate, for example, a hexahydrate. The reaction can be run in an alcoholic solvent, for example, methanol. The reaction can be run at an elevated temperature, for example, from about 40° C. to about 60° C. The reaction can be run in the presence of a base, for example, a hydroxide, for example an inorganic hydroxide, for example, potassium hydroxide. Other hydroxides are contemplated, including sodium hydroxide, lithium hydroxide, cesium hydroxide, and magnesium hydroxide.

To increase purity of the final product from Scheme II, the metal complex of Formula (XIa) can be crystallized one or more times from one or more solvents, for example a cyclic ether and a non-cyclic ether, for example tetrahydrofuran and methyl tert-butyl ether. In some cases the ratio of the cyclic ether to the non-cyclic ether is at most 0.5:10, 1.0:10, 1.5:10, 2.0:10, 2.5:10, 3.0:10, 3.5:10, 4.0:10, 4.5:10 or 5:10. In other cases the ratio of the cyclic ether to the non-cyclic ether is at least 0.5:10, 1.0:10, 1.5:10, 2.0:10, 2.5:10, 3.0:10, 3.5:10, 4.0:10, 4.5:10 or 5:10. For example, some cases the metal complex of Formula (XIa) is crystallized from a mixture of tetrahydrofuran and methyl tert-butyl ether in ratio of at most 0.5:10, 1.0:10, 1.5:10, 2.0:10, 2.5:10, 3.0:10, 3.5:10, 4.0:10, 4.5:10 or 5:10. In other cases the ratio of and tetrahydrofuran and methyl tert-butyl ether is at least 0.5:10, 1.0:10, 1.5:10, 2.0:10, 2.5:10, 3.0:10, 3.5:10, 4.0:10, 4.5:10 or 5:10. In some cases the ratio of tetrahydrofuran and methyl tert-butyl ether is 1.5:10. The product or crystallized product of Formula (IXa) can be crystallized or recrystallized from a solvent, for example an alcohol, for example isopropyl alcohol. Other alcohols are contemplated, including methanol, ethanol, n-propanol, a butanol, n-butanol, iso-butanol, sec-butanol, and t-butanol. Other solvents suitable for crystallization or recrystallization of Formula (XIa) include esters, for example ethyl acetate or isopropyl acetate.

The metal complex of Formula (XIa) is then alkylated with 5-bromopent-1-ene to form the alkylated metal complex of Formula (XIIa). The skilled artisan would understand that other alkylating agents, including other halo alkyl olefins, could be used in place of 5-bromopent-1-ene. For example, alkylating agents of the Formula (XV) could be used:

(XV)

wherein X is Cl, Br, or I, and n is an integer from 1 to 20. For example, n can be from 3 to 11, from 3 to 6, or 3 or 6. Some or all of the hydrogen atoms present in the compound of Formula (XV) can be replaced with deuterium atoms or halogen atoms. The alkylation can be performed in one or more solvents, for example a polar aprotic solvent, for example N,N-dimethyl formamide (DMF). The alkylation can be performed, for example, at a temperature of less than 20° C., for example, from less than 20° C. to 5° C., from less than 20° C. to 10° C., or at about 10° C. The skilled artisan would also understand that when glycine is used to form the metal complex, two alkylations could be performed one after the other. For example, the first alkylation could be performed using a $C_1$-$C_3$ alkane with a leaving group such as a halogen (e.g., methyl bromide, ethyl bromide, n-propyl bromide), or a $C_1$-$C_3$ deuteroalkane with a leaving group such as a halogen (e.g., $CD_3Br$, $CD_3CD_2Br$, $CD_3CD_2CD_2Br$), or a $C_1$-$C_3$ haloalkane with a leaving group such as a more reactive halogen than the other halogens in the haloalkane (e.g., $CF_3Br$, $CF_3CF_2Br$, $CF_3CF_2CF_2Br$). Then, the second alkylation could be performed using the alkylating agent of Formula (XV). The order of the first and second alkylations can be reversed.

Purification of Formula (XIIa) may be achieved by crystallization one or more times from one or more solvents including cyclic and non-cyclic ethers, esters, hexanes and heptanes. For example crystallization may be achieved by using a combination of ethyl acetate and hexanes, ethyl acetate and heptanes, isopropyl acetate and hexanes, isopropyl acetate and heptanes, methyl tertiary-butyl ether and hexanes, methyl tertiary-butyl ether and heptanes or isopropyl acetate and methyl tertiary-butyl ether.

The metal complex of Formula (XIIa) is then cleaved with an acid, for example HCl, using one or more solvents, for example an ether, for example a cyclic ether, for example tetrahydrofuran, to form the amino acid HCl salt of Formula (XIIIa). The skilled artisan would understand that other acids in addition to HCl are contemplated, for example organic or inorganic acids, for example, nitric acid, phosphoric acid, sulfuric acid, boric acid, hydrofloric acid, hydrobromic acid, or perchloric acid.

The salt of Formula (XIIIa) may be further purified by crystallization one or more times with one or more solvents. The solvent may be any suitable solvent including tetrahydrofuran, methyl tertiary-butyl ether, ethyl acetate, isopropyl acetate, ethanol, methanol, isopropanol, acetonitrile, or a combination thereof. In one embodiment, the solvent is acetonitrile.

The amino acid salt of Formula (XIIIa) is then nitrogen protected with a nitrogen protecting group, in this case an Fmoc group, yielding the protected amino acid of Formula (XIVa). In some embodiments, the compound of Formula (XIVa) is taken on to the crystallization step as is. In other embodiments, the compound of Formula (XIVa) is converted to a salt prior to crystallization. Formation of the salt of Formula (XIVa) may be achieved in any suitable solvent including acetonitrile, methyl tertiary-butyl ether, tetrahydrofuran or a combination thereof. One of skill in the art would also readily understand that other nitrogen protecting groups are contemplated, for example the nitrogen protecting groups for $R_2$ in the crystalline compound of Formula (I) or its crystalline salt herein. For example, a protected amino acid cyclohexylamine salt of Formula (XIVa) can then be crystallized from one or more ethers, for example, two ethers, for example a cyclic ether and a non cyclic ether, for example tetrahydrofuran and methyl tert-butyl ether.

The protected amino acid cyclohexylamine salt of Formula (XIVa) can then be crystallized to form the crystalline compound of Formula (IIIa).

The crystallization can be performed using one or more solvents, for example two solvents, for example an alkane and haloalkane, for example hexanes and chloroform. In some cases the ratio of the alkane to the haloalkane is at least 6:1, 5:1, 4:1, 3:1, 2:1, or 1:10. In some cases the ratio of the alkane to the haloalkane is at most 6:1, 5:1, 4:1, 3:1, 2:1, or 1:10. For example, the crystalline compound of Formula (IIIa) may be obtained by crystallization from a mixture of hexanes and chloroform in the ratio of at least 6:1, 5:1, 4:1, 3:1, 2:1, or 1:1. The crystalised IIIa may also obtained by crystallization from a mixture of hexanes and chloroform in the ratio of at most 6:1, 5:1, 4:1, 3:1, 2:1, or 1:1. In some cases the ratio of hexanes and chloroform is 2:1.

The crystallization can be performed at a temperature ranging from, for example, about −5° C. to about −20° C., about −10° C. to about −20° C., or about −15° C. to −20° C. Herein, unless otherwise indicated, any compound or its salt may be crystalline. Herein, unless otherwise indicated, any compound or its salt may be crystalline at a temperature, for example, of about 0° C. or less, about −5° C. or less, about −10° C. or less, about −15° C. or less, about −20° C. or less, about −5° C., about −6° C., about −7° C., about −8° C., about −9° C., about −10° C., about −11° C., about −12° C., about −13° C., about −14° C., about −15° C., about −16° C., about −17° C., about −18° C., about −19° C., or about −20° C.

The skilled artisan would understand, for example, that the crystalline compound of Formula (IIIa) could be further activated or protected at its carboxylic acid function with, for example, a protecting or activating group $R_3$ of the crystalline compound of Formula (I) or its crystalline salt.

Stapled and Stitched Polypeptides

The crystalline compounds and their crystalline salts of Formula (I), including the crystalline compounds and their crystalline salts of Formulae (IIa), (IIb), (IIIa) and (IIIb), as well as the optionally crystalline compounds and their optionally crystalline salts of Formula (IV), can be used to synthesize peptides, polypeptides, and crosslinked polypeptides that are useful for treating and preventing diseases.

The crosslinked polypeptides can contain secondary structures such as a helix, for example, an alpha helix. The crosslinker can stablize the secondary structures relative to an otherwise identical but uncrosslinked polypeptide. And the crosslinker can be formed by, for example, joining the terminal alkene side chains of, for example, two crystalline alkene α, α-disubstituted amino acids or their crystalline salts herein that are incorporated into a polypeptide through, for example, a metal catalyzed olefin metathesis reaction (e.g., forming a stapled peptide). This process is depicted in Scheme III, below:

Scheme III

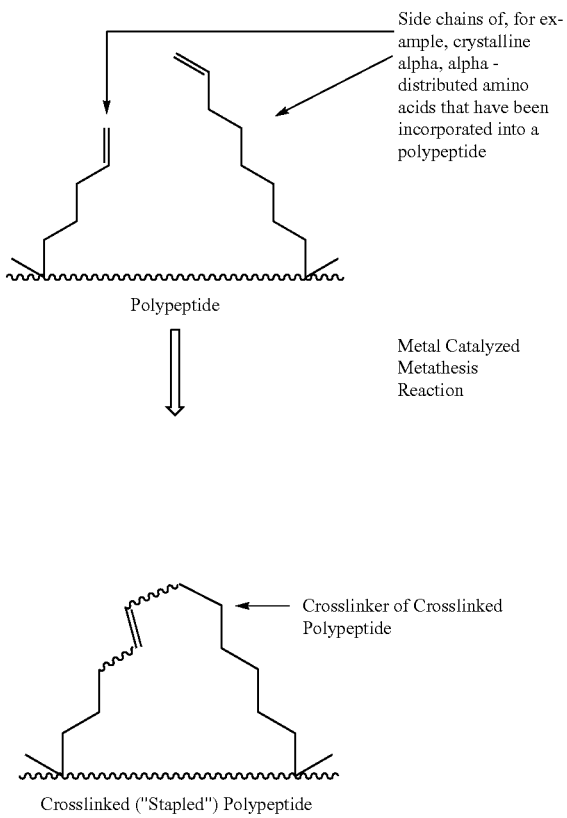

Crosslinked ("Stapled") Polypeptide

Scheme IV

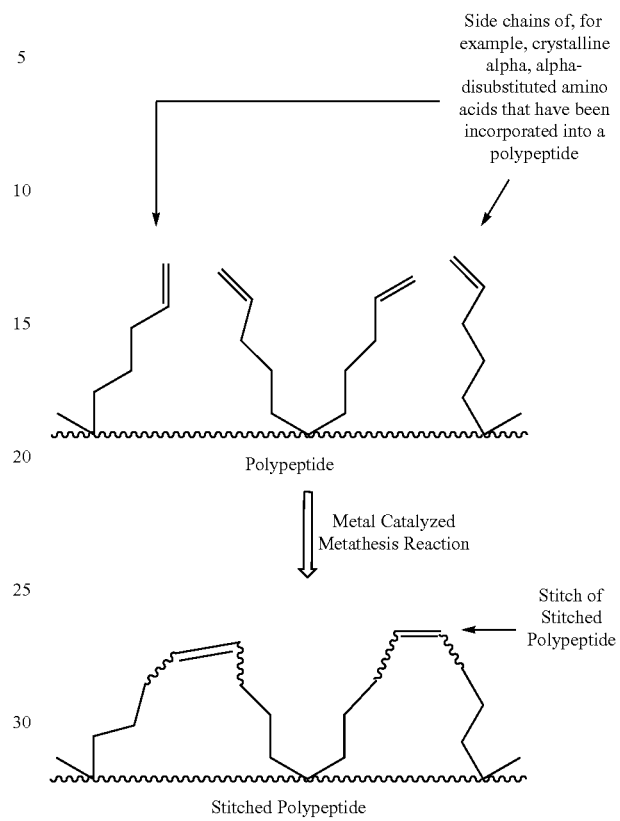

Stitched Polypeptide

Examples of stapled polypeptides are found, inter alia, for example, in International Application No. PCT/US2004/038403.

The crystalline compounds and their crystalline salts of Formula (I), including the crystalline compounds and their crystalline salts of Formulae (IIa), (IIb), (IIIa) and (IIIb), as well as the optionally crystalline compounds and their optionally crystalline salts of Formula (IV), can be used to synthesize peptides, polypeptides, and stitched polypeptides that are useful for treating and preventing diseases.

For example, two of the crystalline compounds and their crystalline salts of Formula (I), can be incorporated into a polypeptide backbone along with an α, α-disubstituted amino acid having terminal olefins on each of its side chains, for example the compound of Formula (XVI):

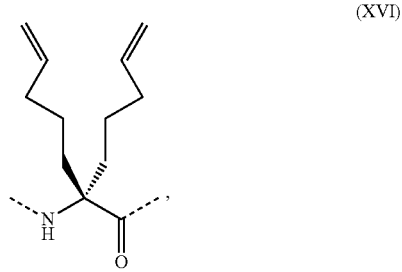

(XVI)

as shown in scheme IV. Metal catalyzed metathesis reaction of the olefins yields a stitched peptide.

Examples of stitched polypeptides are found, for example, in International Application Publication No. WO2008/121767.

Methods to effect formation of peptidomimetic macrocycles which are known in the art can be employed. For example, the preparation of peptidomimetic macrocycles are described in Schafmeister et al., *J. Am. Chem. Soc.* 122: 5891-5892 (2000); Schafineister & Verdine, *J. Am. Chem. Soc.* 122:5891 (2005); Walensky et al., *Science* 305:1466-1470 (2004); U.S. Pat. No. 7,192,713 and International Pat. App. Pub. No. WO 2008/121767.

Herein, unless otherwise indicated, the term "peptide synthesis" encompasses coupling of two or more amino acids with the aid of a coupling reagent. Peptide synthesis may be performed in "liquid" or "solution" phase where the coupling of the amino acids is performed in a solvent system. Peptide synthesis may also, or alternatively, be performed on "solid phase" where an amino acid is attached to a polymeric or solid support by a covalent bond at the N- or C-terminus of an amino acid. Peptides can be made, for example, by chemical synthesis methods, such as those described in Fields et al., Chapter 3 in *Synthetic Peptides: A User's Guide*, ed. Grant, W. H. Freeman & Co., New York, N.Y., 1992, p. 77; and Goodman, M., et al., Houben-Weyl Methods in Organic Chemistry: Synthesis of Peptides and Peptidomimetics, *Thieme Publishers, Volumes* 1-5, (1994). For example, peptides can be synthesized using automated Merrifield techniques of solid phase synthesis with the amino groups of the amino acids employed in the synthesis protected, for example by t-Boc or Fmoc protecting groups. An automated peptide synthesizer (e.g., Applied Biosystems (Foster City, Calif.), Model 430A, 431, or 433) can be employed in making peptides.

Herein unless otherwise indicated, peptidomimetic precursors and peptidomimetic macrocycles and their salts described herein can be produced using solid phase peptide synthesis (SPPS), where for example, a C-terminal amino acid is attached to a cross-linked polystyrene resin via an acid or base labile bond with a linker. The resin can be, for example, insoluble in the solvents used for synthesis, making it relatively simple and fast to wash away excess reagents and by-products. The N-terminus of each amino acid added to the growing peptide chain can be protected, for example, with an Fmoc group, which is stable in acid, but removable by base. Side chain functional groups can be protected, as necessary or desirable, for example, with base stable, acid labile groups.

Herein, unless otherwise indicated, the peptidomimetic precursors can be made, for example, in a high-throughput, combinatorial fashion using, for example, a high-throughput polychannel combinatorial synthesizer (e.g., Thuramed TETRAS multichannel peptide synthesizer from CreoSalus, Louisville, Ky. or Model Apex 396 multichannel peptide synthesizer from AAPPTEC, Inc., Louisville, Ky.).

Herein, unless otherwise indicated, solution peptide synthesis can be performed in a manner wherein reagents are fully or partially dissolved in, for example, an appropriate solvent, for example, a polar aprotic solvent. In a representative case employing, for example, a solid crystalline N-terminally protected olefinic amino acid with a removable protecting group (e.g., t-Butyloxycarbonyl, Benzyloxycarbonyl, Fluorenylmethoxycarbonyl) and a C-protected amino acid with a selectively removable ester (e.g., methyl, benzyl, t-butyl), the amino acids can be fully or partially dissolved in a solvent and an activating agent is added to accomplish peptide bond formation between the amino acids. Solution peptide synthesis can also utilize first formation of active esters of N-protected olefinic amino acids (e.g., N-hydroxysuccinamide, p-nitrophenyl, 2,4,6-trichlorophenyl, pentafluorophenyl) and then subsequent reaction of the activated amino acid with an unprotected or C-protected amino acid. The active esters of olefinic amino acids can be prepared, for example, by reacting a solid N-protected olefinic amino acid with an appropriate alcohol with help of the condensing agent (e.g., dicyclohexylcarbodiimide). These same procedures can also be used, for example, when one or both of the amino acids to be reacted are part of, and incorporated into, respectively, for example, one or two peptides.

Formation of C-terminally protected olefinic amino acids can easily be facilitated by reacting dry solid olefinic amino acid(s) with an appropriate alcohol (e.g., methyl, ethyl, benzyl) under, for example, anhydrous conditions. Formation of a peptide where olefinic amino acid is located in the C-terminal position can accomplished, for example, in the similar way. Solution methods of peptide preparation can be easily adapted to process scale. The starting materials and reagents used herein in preparing any compound herein and as above-and-below disclosed, unless otherwise indicated, for example, can be available from commercial sources such as Aldrich, Sigma or Bachem, or can be prepared by methods known to those skilled in the art following procedures set forth, for example, in references such as: Fieser and Fieser's Reagents for Org. Syn. Vol. 1-17, Organic Reactions Vol. 1-40, March's Advanced Organic Synthesis, Larock's Comprehensive Organic Transformations, Bodansky and Bodansky's The Practice of Peptide Synthesis, Greene's Protective Groups in Organic Synthesis, Wei, Q., et al., *Tetrahedron* 56: 2577-2582 (2000), Belokon, Y. N., et al., *Tetrahedron: Asymmetry* 9: 4249-4252 (1998), Belokon, Y., *Pure & App. Chem.* 64(12): 1917-1924 (1992), Ueki, H., et al., *J. Org. Chem.* 68: 7104-7107 (2003).

These schemes herein are illustrative of some methods by which compounds herein and their salts (which can be crystalline) can be synthesized, and various modifications to these schemes can be made and will be suggested to one skilled in the art having referred to this disclosure.

The starting materials and intermediates of the reactions of any embodiment herein, herein and as-above disclosed, unless otherwise indicated, may be isolated and purified if desired using conventional techniques, including, but not limited to filtration, distillation, crystallization, chromatogram, flash chromatography, HPLC, MPLC, Chromatotron®, ion exchange chromatography, crystallization with Mosher acids or Mosher esters, and the like. Such materials may be characterized using conventional means, including physical constructs and spectral data, for example proton NMR, carbon NMR, IR spectroscopy, polarimetry, atomic absorption, elemental analysis, UV spectroscopy, FTIR spectroscopy, and the like. In any embodiment here and as-above described, unless otherwise indicated, chromatography can be excluded in making any of the compounds or their salts.

Unless specified to the contrary, the reactions described herein can take place at, for example, from about 0.001 to about 100 atmospheres (atm), for example, about 0.001 atm, about 0.01 atm, about 0.1 atm, about 1 atm, about 2 atm, about 3 atm, about 4 atm, about 5 atm, about 10 atm, about 20 atm, about 50 atm, or about 100 atm.

Reactions in any embodiment herein, unless otherwise indicated, can be run, unless otherwise specified, for example, open to the atmosphere, or under an inert gas atmosphere such as, for example, nitrogen or argon.

Reactions in any embodiment herein, unless otherwise indicated, can be run, unless otherwise specified, for example, at temperatures from about −78° C. to about 150° C., for example from about −78° C., about −50° C., about −20° C., about 0° C., about 10° C., about 20° C., about 23° C., about 25° C., about 27° C., about 30° C., about 40° C., about 50° C., about 100° C., about 125° C., about 150° C., at about ambient temperature, or at about room temperature.

Reactions herein, unless otherwise indicated, can have a yield, unless otherwise explicitly stated, based on the theoretical yield, for example, ranging from about 1% to about 99%. The yield can be, for example, about 99%, about 98%, about 97%, about 96%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5%.

Reactions herein, unless otherwise indicated, can be run, unless otherwise specified, for example, for a time ranging from about 0.1 to about 96 hours, e.g., for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 48 hours, about 72 hours, or about 96 hours, Selective Uses of Crosslinked Peptidomimetic Macrocycles (Stitched and Stapled Peptides)

Crosslinked peptidomimetic macrocycles (stitched or stapled peptides), made with for example at least one of the crystalline compounds and their crystalline salts of Formula (I), including the crystalline compounds and their salts of Formulae (IIa), (IIb), (IIIa) and (IIIb), as well as the optionally crystalline compounds and their optionally crystalline salts of Formula (IV), can be used to treat or prevent diseases. For example, the crosslinked peptidomimetic macrocycles (stitched or stapled peptides) can be used to treat or prevent cancers. Selected examples of cancers include, for example, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Diseases which can be treated by stitched or stapled peptides can be found, for example, in International Application No. PCT/US2004/038403 ("the '403 application") and International Application Publication No. WO2008/121767 ("the '767 publication").

While inventive embodiments have been shown and described herein, such embodiments are provided by way of example only. Numerous variations, changes, and substitutions will now occur to those skilled in the art without departing from the inventive disclosure herein. The following Examples are illustrative and should not be construed as limiting.

EXAMPLES

Example 1

Preparation of crystalline N-Fmoc-(R)-α-methyl-α-aminodec-9-enoic acid

Example 1a

Preparation of (R)-2-[N—(N'-Boc-prolyl)amino]benzophenone

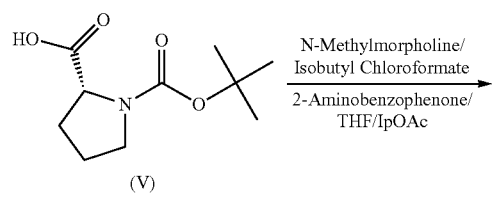

(V)

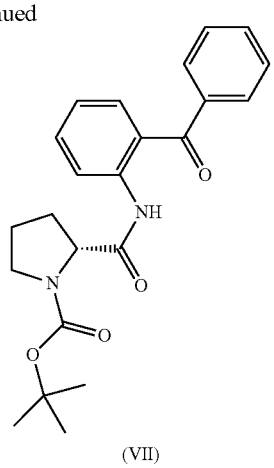

(VII)

Tetrahydrofuran and 9.6 kg (1.0 equivs.) of Boc-D-proline (V) were added to a reactor and cooled to −5° C. 5.3 kg (1.15 equivs.) of N-methylmorpholine were charged followed by a slow addition of 6.1 kg (1.0 equivs.) of isobutyl chloroformate in tetrahydrofuran while maintaining the internal temperature at <5° C. The mixture was allowed to agitate at 20-25° C. for 45-60 minutes and then was analyzed by TLC for completion. A solution of 8.2 kg (0.9 equvs.) of 2-aminobenzophenone/tetrahydrofuran was charged and the mixture was allowed to agitate at 20-25° C. until the reaction is deemed complete. The mixture was concentrated to ½ volume and isopropyl acetate was charged. The organic product layer was then washed with a 5% sodium bicarbonate solution, water was charged, then the pH was adjusted to 2.0-2.5 with 25% sulfuric acid. The layers were split and the organic product layer was washed again with water. The organic product solution was then concentrated and crystallized from isopropyl acetate and washed with methyl tert-butyl ether. Product (VII) was isolated and dried under heat and vacuum. Yield: 12 kg, 66.7%.

Example 1b

Preparation of D-Proline-2-Aminobenzophenone amide

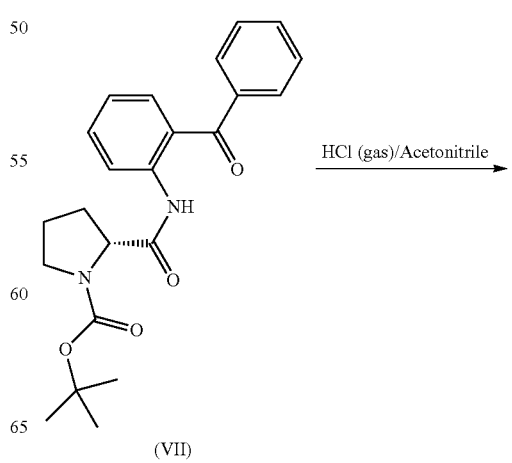

(VII)

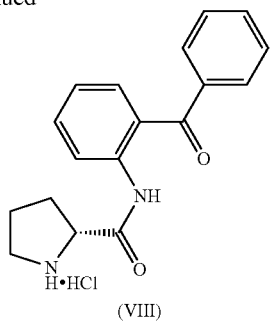

(VIII)

12.0 kg (1.0 equivs.) of Boc-D-proline-2-aminobenzophenone (VII) amide was dissolved into acetonitrile. 2.2 kg (2.0 equivs.) of hydrogen chloride gas was then charged/bubbled into the solution. The resulting mixture was then allowed to agitate at 20-25° C. until the reaction was complete. Methyl tert-butyl ether was added and the solid product was isolated out of the reaction solution and washed with additional methyl tert-butyl ether. The product (VIII) was dried under heat and vacuum. Yield: 9.1 kg, 100%.

Example 1c

Preparation of (R)-2-[N—(N'-benzylprolyl)amino]benzophenone (D-BPB)

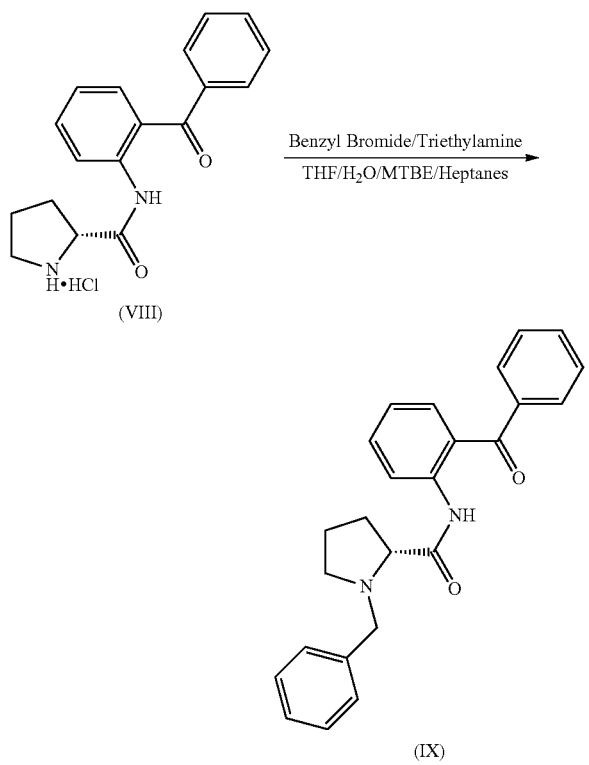

9.1 kg (1.0 equivs.) of D-proline-2-aminobenzophenone amide.HCl (VIII) was dissolved into tetrahydrofuran and water. 8.1 kg (2.4 equivs.) of triethylamine was then charged, followed by a slow addition of 7.9 kg (1.4 equivs.) of benzyl bromide. The mixture was then allowed to agitate at 20-25° C. until the reaction was complete. Methyl tert-butyl ether and water were added and the resulting solution was pH adjusted to 2.0-2.5 with a 1N hydrochloric acid solution. The mixture was concentrated to remove all the tetrahydrofuran. The product slurry was then isolated and washed with methyl tert-butyl ether. The product (IX) was dried under heat and vacuum Yield: 10.5 kg, 82.7%.

Example 1d

Preparation of (R)-Ala-Ni-BPB

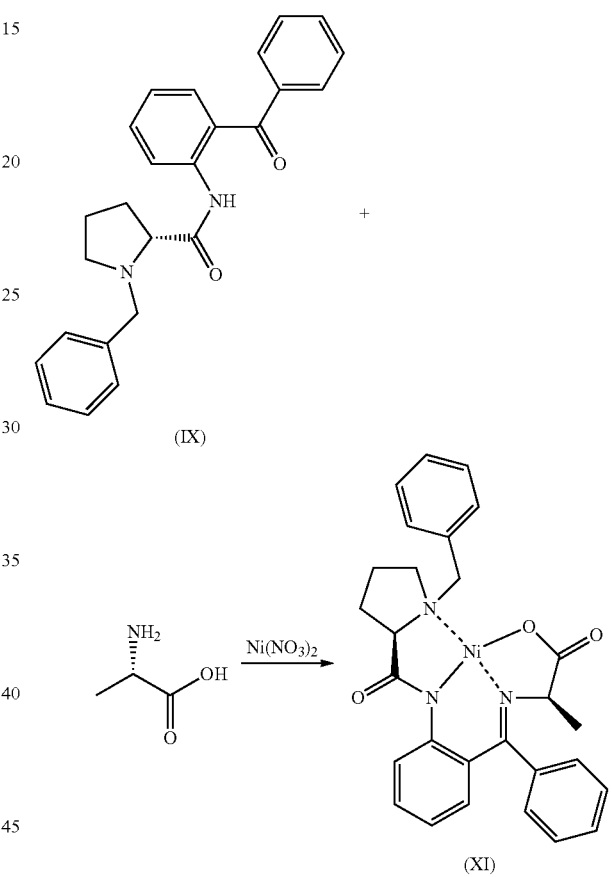

10.5 kg (1.0 equivs.) of D-BPB (IX), 14.1 kg (1.78 equivs.) nickel (II) nitrate hexahydrate, 4.9 kg (2.0 equivs) of L-alanine, and methanol were charged to a reactor. The mixture was heated to 40° C. and a solution of 12.2 kg (8.0 equivs.) of potassium hydroxide/methanol was slowly added while maintaining the internal temperature of <50° C. The reaction mixture was then heated up to 60° C. and allowed to agitate at temperature until the reaction was complete. The mixture was then cooled to 20-25° C. and 8.2 kg (5.0 equivs.) of acetic acid was slowly charged while maintaining an internal temperature of <35° C. The reaction solution was concentrated to a solid. Tetrahydrofuran and isopropyl acetate were then added to dissolve the solid(s) and the organic product layer was washed 2× with water. The solution was then concentrated again and material was subsequently crystallized out of tetrahydrofuran and methyl tert-butyl ether. The product was isolated, rinsed with additional methyl tert-butyl ether and analyzed for purity. To improve purity the product (XI) was recrystallized out of isopropyl alcohol and then isolated, and dried under heat and vacuum. Yield: 6.8 kg, 48.6%.

Recrystallization Procedure

THF was added to the crude product (15 mL per 10 g of starting material (D-BPB)) and the resulting mixture was heated to 50° C. The mixture was maintained at 50° C. for 1 h, then methyl tertiary-butyl ether was added (50 mL per 10 g of starting material (D-BPB)). The mixture was maintained at 50° C. for additional 1 h after which it was cooled to 35° C. The mixture was filtered and the resulting solid was washed with methyl tertiary-butyl ether (20 mL per 10 g of starting material (D-BPB)) to obtain the crystalline product XI.

Alternate Recrystallization Procedure

Isopropyl acetate was added to the crude product (40 mL per 4 g of starting material (D-BPB)) and the resulting mixture was maintained at room temperature for 30 min. The mixture was then filtered to obtain the crystalline product XI.

Example 1e

Preparation of R8-Ni-BPB

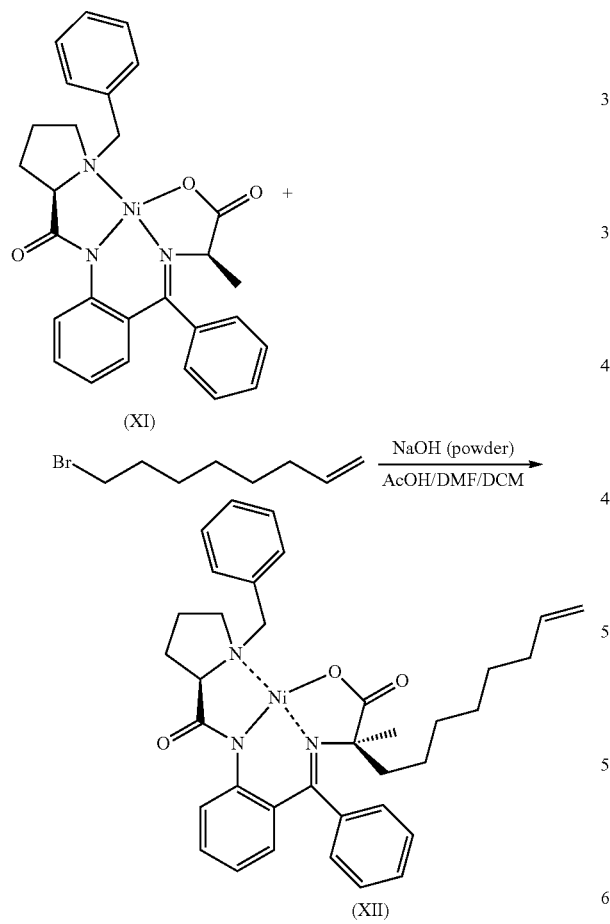

6.8 kg (1.0 equivs.) of (R)-Ala-Ni-BPB (XI) was charged to a reactor and dissolved up into dimethylformamide and cooled to 10° C. 1.4 kg (2.5 equivs.) of sodium hydroxide (powder) was then charged to the same reactor and the mixture was sparged with nitrogen and agitated until a solution formed at 10° C. 5.2 kg (2.0 equivs.) of 8-bromo-1-octene was charged to the reactor while maintaining an internal temperature of <20° C. The mixture was then allowed to agitate at 20-25° C. until the reaction was complete. Once the reaction was complete, the solution was cooled to 10° C. and 0.5 kg (0.6 equivs.) of acetic acid was charged maintaining the internal temperature <25° C. Water was then charged followed by methyl tert-butyl ether and the organic layer was washed. The organic layer was then washed 2 more times with water and then concentrated. The product oil was then co-stripped with methylene chloride and dissolved up in additional methylene chloride. The product (XII) solution was taken on into the next processing step.

Example 1f

Preparation of (R)-2-Amino-2-methyl-dec-9-enoic acid

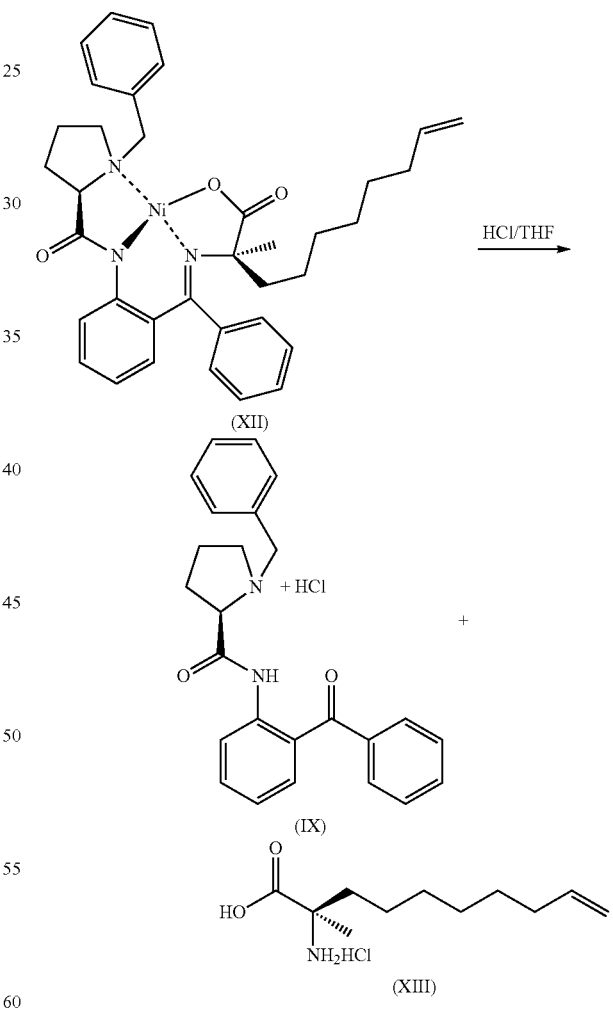

The R8-Ni-BPB (XII)/DCM solution was charged to a 50-L chem-glass reactor and stripped to an oil. Tetrahydrofuran was then added and the mixture was agitated at 20-25° C. until a solution formed. 7.8 kg (5.0 equvs.) of 32% hydrochloric acid was charged slowly while maintaining an internal temperature of <30° C. The mixture was then allowed to agitate for 6-8 hours at ambient temperature. The mixture was then concentrated to remove tetrahydrofuran to yield a slurry. Additional water was added and the slurry was agitated at ambient temperature for 1-2 hours. The solid BPB salts were isolated by filtration and rinsed with additional water followed by methyl tert-butyl ether. The product filtrates were then re-charged to the reactor yielding a tri-phased solution. The lower-most layer was split from the upper two layers. The combined two organic layers were then washed 3× with water and concentrated to an oil. Acetonitrile was then added and the mixture was warmed to 70° C. for 30 minutes. The mixture was then cooled to 25-30° C. and the solid product was isolated. The solid filter-cake was washed with acetonitrile and methyl tert-butyl ether, then analyzed for purity. The product was then re-slurried out of additional acetonitrile and washed with acetonitrile and methyl tert-butyl ether. The material (XIII) was isolated and dried under heat and vacuum. Yield: 1.55 kg, 48%.

Recrystallization Procedure

Acetonitrile (23 mL per 10 g of starting material (oil of (R)-Ala-Ni-BPB (XI))) was added to the crude product and the resulting mixture was heated to 70° C. for 30 min after which it was cooled to 20° C. The mixture was filtered and the resulting solid was washed with acetonitrile (5 mL) and methyl tertiary-butyl ether (8.5 mL) to obtain the crystalline product XIII.

Alternate Recrystallization Procedure to Prepare XIII-II

Acetonitrile (30 mL per 10 g of starting material (oil of (R)-Ala-Ni-BPB (XI))) was added to the crude product and the resulting mixture was heated at 60° C. for 30 min followed by cooling to 30° C. The mixture was then filtered and washed with 5 mL acetonitrile to obtain the crystalline product XIII.

Alternate Recrystallization Procedure to Prepare XIII-II

Acetonitrile (23 mL per 10 g of starting material (oil of (R)-Ala-Ni-BPB (XI))) was added to the crude product and the resulting mixture was heated at 40° C. for 30 min followed by cooling to room temperature. The mixture was then filtered and washed twice with 5 mL acetonitrile to obtain the crystalline product XIII.

Example 1g

Preparation of Crystalline N-Fmoc-(R)-α-methyl-α-aminodec-9-enoic acid

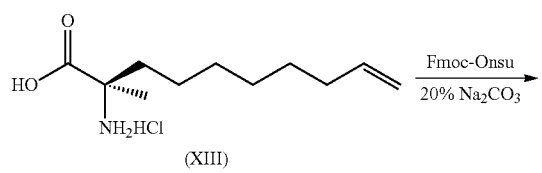

(XIII)

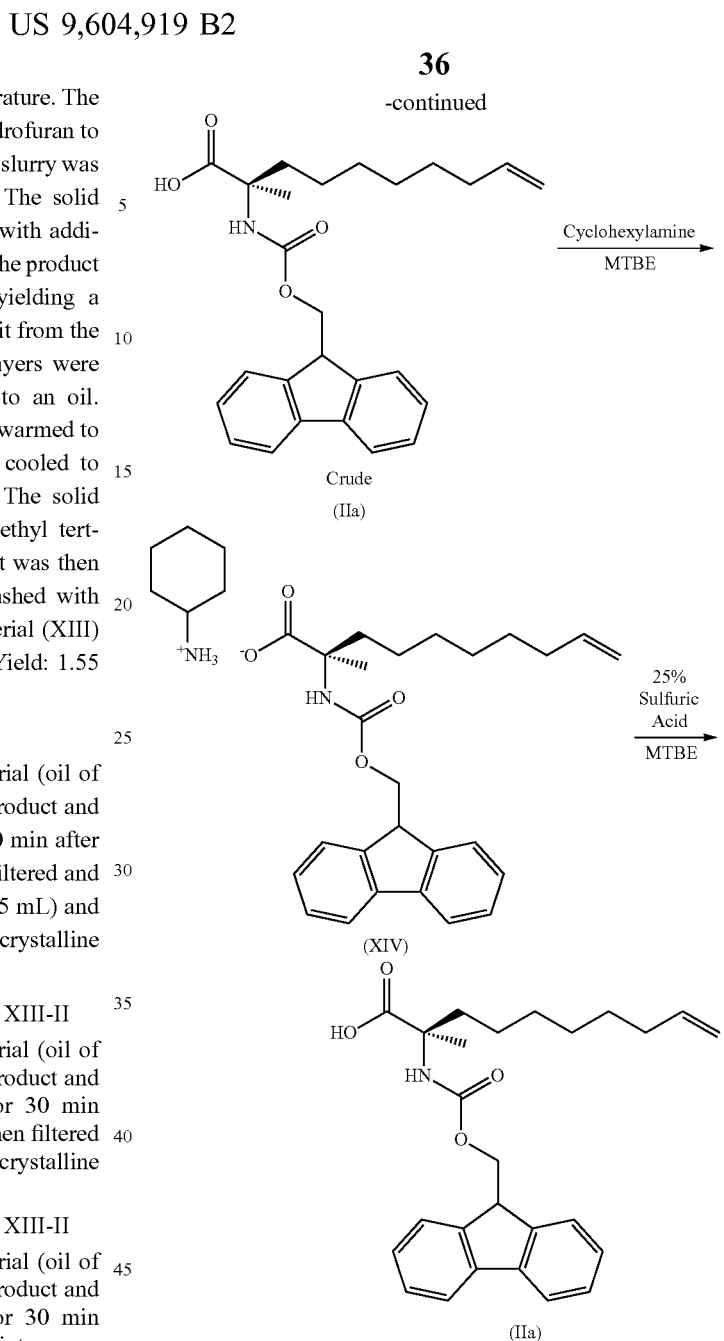

1.55 kg (1.0 equiv.) of 2-amino-2-methyl-dec-9-enoic acid.HCl (XIII) was suspended in water and polished filtered to remove trace amounts of D-BPB.HCl from the solution. Methyl tert-butyl ether was added and the aqueous product layer was extracted once with methyl tert-butyl ether. The aqueous product layer was re-charged and tetrahydrofuran was added. A 20% aqueous sodium carbonate solution (2.75 equiv.) was charged to the mixture followed by Fmoc-OSu (0.89 equiv.). The mixture was allowed to react at 20-25° C. while maintaining the pH between 8.5-9.0 with additional amounts of the 20% sodium carbonate solution until the reaction was complete. The mixture was pH adjusted down to pH 2.0-2.5 with conc. hydrochloric acid. Tetrahydrofuran was distilled off and methyl tert-butyl ether was charged. The layers were separated and the organic layer was washed 3 more times with additional water. The organic layer was then concentrated under vacuum and co-stripped with methyl tert-butyl ether. The resulting crude oil was redissolved in methyl tert-butyl ether and cyclohexylamine (1.10 equiv.) was added slowly to obtain a pH range of 8.5-9.0. The slurry was agitated at ambient temperature (20-25° C.) for 3 hours and the solid product salt (XIV) was isolated by filtration. The solids were rinsed twice with additional methyl tert-butyl ether and the solid wetcake was recharged to a clean reactor. The wetcake was recrystallized from tetrahydrofuran and methyl tert-butyl ether to improve the purity. The solid salt was suspended in methyl tert-butyl ether and water and the pH adjusted to 2.0-2.5 with 25% sulfuric acid. The organic product layer was washed with water until all of the cyclohexylamine was removed. The organic product layer was concentrated and co-stripped with hexanes to a loose oil. The product (IIa) was then crystallized out of chloroform and hexanes and dried at <0° C. under a 1.0 cfm nitrogen sweep. Yield: 1.12 kg, 41.5%

Recrystallization Procedure

Methyl tertiary-butyl ether (800 mL per 36 g of starting material XIII) was added to the crude product and the pH of the resulting mixture was adjusted to 8-9 using CHA at 20° C. The mixture was mixed at 20° C. and after 1 h crystals started forming. Additional methyl tertiary-butyl ether was added (200 mL) and the resulting slurry was mixed for 18 h. The mixture was filtered and the resulting solid was washed with twice methyl tertiary-butyl ether (200 mL and 8.5 mL) to obtain the crystalline product XIII. The product was analyzed for chiral purity, and if the results were less than 95% Fmoc-R8 vs. Fmoc-S8 then crystallization was performed to upgrade the chiral purity by dissolving dry FmocR/S (50 g) in THF (50 mL). Once FmocR/S was dissolved, methyl tertiary-butyl ether was added (900 mL) and the mixture was mixed at 20° C. for 18 h. The mixture was then filtered and washed twice with methyl tertiary-butyl ether (100 mL each). The chiral purity of the resulting crystalline product XIV was about 97.8%

Alternate Recrystallization Procedure for XIV-I

Methyl tertiary-butyl ether (1500 mL per 47 g of starting material XIII) was added to the crude product and the pH of the resulting mixture was adjusted to 8-9 using CHA at 20° C. The mixture was mixed at this temperature for 3 h after which it was filtered and the resulting solid was washed with methyl tertiary-butyl ether (250 mL).

Alternate Recrystallization Procedure for XIV-II

Methyl tertiary-butyl ether (400 mL per 20 g of starting material XIII) was added to the crude product and the pH of the resulting mixture was adjusted to 8-9 using CHA at 20° C. Additional 200 mL methyl tertiary-butyl ether was added and the mixture was mixed at this temperature for 2 h after which it was filtered and the resulting solid was washed with methyl tertiary-butyl ether (10 mL).

Alternate Recrystallization Procedure for XIV-III

Methyl tertiary-butyl ether (50 mL per 4 g of starting material XIII) was added to the crude product and the pH of the resulting mixture was adjusted to 8-9 using CHA at 20° C. The mixture was mixed at this temperature for 45 min after which it was filtered and the resulting solid was washed with methyl tertiary-butyl ether (10 mL).

Recrystallization Procedure for IIa

Chloroform (70 mL) was added to the crude product (25 g) and the resulting mixture was cooled to 0° C. Hexanes (210 mL) were then slowly added so as to maintain the temperature at 0° C. The mixture was further maintained at this temperature for 1 h after which it was filtered cooled and the resulting solid was dried under vacuum at 0° C.

Alternate Recrystallization Procedure for IIa-I

Chloroform (2200 m L) was added to the crude product (1100 g). Hexanes (6600 L) were then added slowly and the resulting mixture was cooled to less than 0° C. The mixture was further mixed at temperature below 0° C. for 1 h after which it was filtered at less than 0° C. and the resulting solid was dried under vacuum at temperature below 0° C.

Example 2

Preparation of crystalline N-Fmoc-(S)-α-methyl-α-aminohept-6-enoic acid

Example 2a

Preparation of (S)-2-[N—(N'-Boc-prolyl)amino]benzophenone

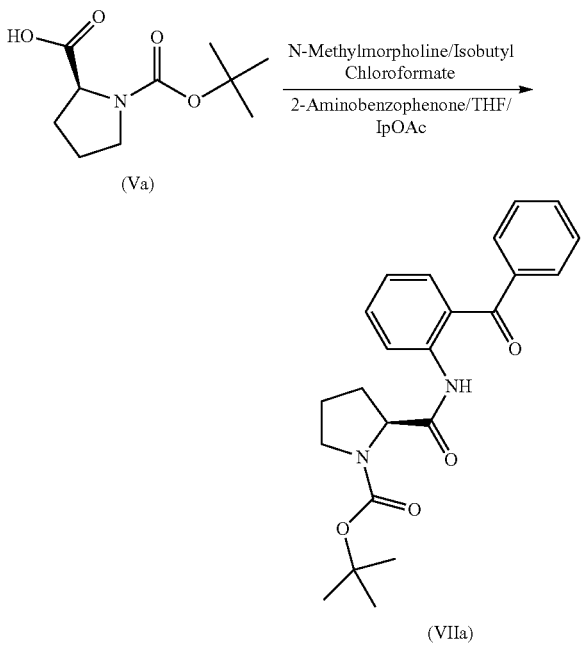

Tetrahydrofuran and 7.5 kg (1.0 equivs.) of Boc-L-proline (Va) were added to a reactor and the resulting solution was cooled to −5° C. 4.2 kg (1.05 equivs.) of N-methylmorpholine were charged, followed by slow addition of 5.3 kg (1.0 equivs.) of isobutyl chloroformate in tetrahydrofuran while maintaining an internal temperature of <5° C. The mixture was allowed to agitate at 20-25° C. for 45-60 minutes and then was analyzed by TLC for completion. A solution of 6.2 kg (0.9 equvs.) of 2-aminobenzophenone/tetrahydrofuran was charged and the mixture was allowed to agitate at 20-25° C. until the reaction was shown to be complete by TLC. The mixture was concentrated to ½ A volume and isopropyl acetate was charged. The organic product layer was then washed with a 5% sodium bicarbonate solution, water was charged, and then pH adjusted to 2.0-2.5 with 25% sulfuric acid. Layers were split and the organic product layer was washed again with water. The organic product solution/layer was then concentrated and crystallized from isopropyl acetate and washed with methyl tert-butyl ether. Product (Vila) was then isolated and dried under heat and vacuum. Yield: 9.3 kg, 75%.

Example 2b

Preparation of L-Proline-2-Aminobenzophenone amide

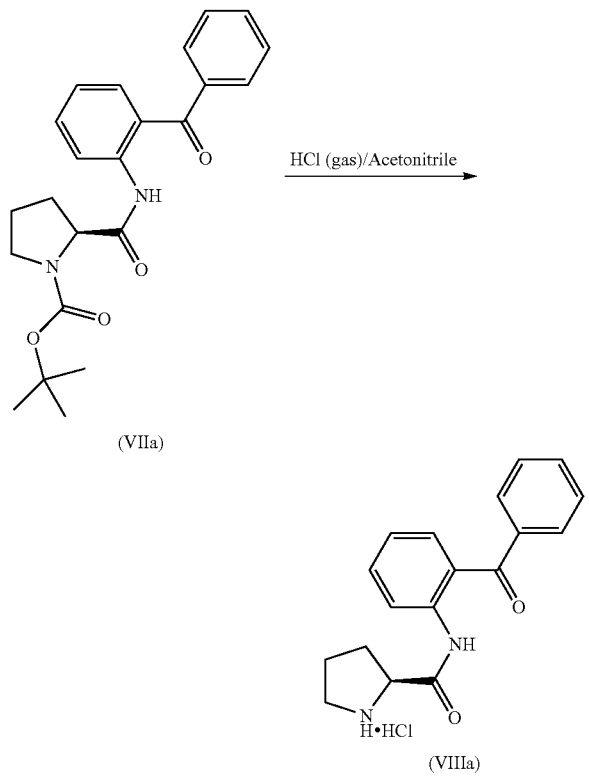

(VIIa)

(VIIIa)

9.4 kg (1.0 equivs.) of Boc-L-proline-2-aminobenzophenone amide (VIIa) was dissolved into acetonitrile. 1.7 kg (2.0 equivs.) of hydrogen chloride gas were then charged/bubbled into the solution. This mixture was allowed to agitate at 20-25° C. until the reaction was demonstrated to be complete by TLC. Methyl tert-butyl ether was added and a solid product was isolated out of the reaction solution and washed with additional methyl tert-butyl ether. The product (VIIIa) was dried under heat and vacuum. Yield: 7.0 kg, 100%.

Example 2c

Preparation of (S)-2-[N—(N'-benzylprolyl)amino] benzophenone (L-BPB)

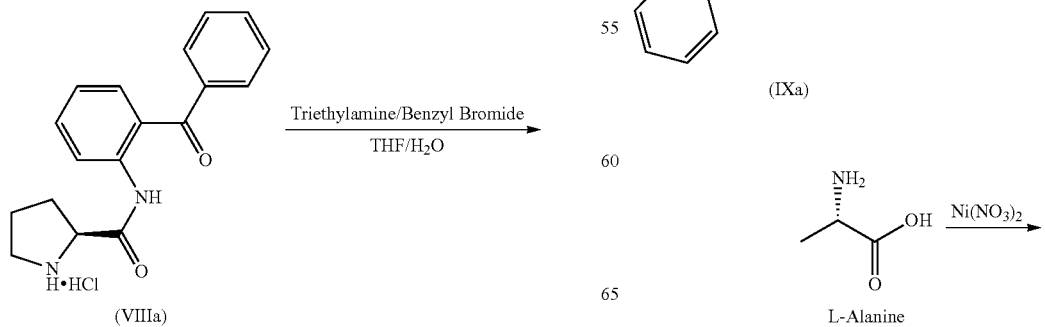

(VIIIa)

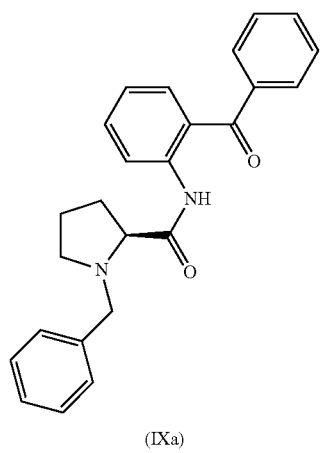

(IXa)

7.1 kg (1.0 equivs.) of L-proline-2-aminobenzophenone amide.HCl (VIIIa) was dissolved into tetrahydrofuran and water. 5.8 kg (2.4 equivs.) of triethylamine were then charged followed by a slow addition of 5.9 kg (1.4 equivs.) of benzyl bromide. The mixture was then allowed to agitate at 20-25° C. until the reaction was complete. Methyl tert-butyl ether and water were added and the solution pH was adjusted to 2.0-2.5 with a 1N hydrochloric acid solution. The mixture was concentrated to remove all the tetrahydrofuran. The product slurry was then isolated and washed with methyl tert-butyl ether. The product (IXa) was dried under heat and vacuum. Yield 7.7 kg, 84.0%.

Example 2d

Preparation of (S)-Ala-Ni-BPB

-continued

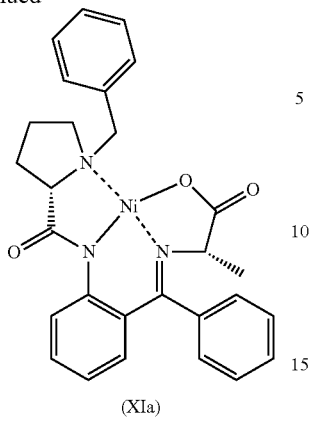

(XIa)

7.9 kg (1.0 equivs.) of L-BPB (IXa), 12.1 kg (1.78 equivs.) nickel (II) nitrate hexahydrate, 3.7 kg (2.0 equivs) of L-alanine, and methanol were charged to a reactor. The mixture was heated to 40° C. and a solution of 8.2 kg (8.0 equivs.) of potassium hydroxide/methanol was slowly added while maintaining the internal temperature at <50° C. The reaction mixture was then heated up to 60° C. and allowed to agitate at temperature until the reaction was complete. The mixture was subsequently cooled to 20-25° C. and 8.9 kg (5.0 equivs.) of acetic acid was slowly charged while maintaining the internal temperature at <35° C. The reaction solution was then concentrated to a solid. Tetrahydrofuran and isopropyl acetate were added to dissolve the solids and the organic product layer was washed twice with water. The solution was concentrated again and material crystallized out of tetrahydrofuran and methyl tert-butyl ether. The product was isolated, rinsed with additional methyl tert-butyl ether and analyzed for purity. To improve purity the product (XIa) was recrystallized out of isopropyl alcohol and then isolated, and dried under heat and vacuum. Yield: 6.0 kg, 56.0%.

Recrystallization procedure for XIa

Methyl tertiary-butyl ether (550 mL per 50 g of starting material L-BPB) was added to the crude product (S)-Ala-Ni-BPB and the slurry was then heated to 50° C. before cooling it to 20° C. The mixture was mixed at 20° C. for 16 h. The mixture was filtered and the resulting solid was washed with methyl tertiary-butyl ether (100 mL) to obtain the crystalline product XIa.

Alternate Recrystallization Procedure for XIa-I

Methyl tertiary-butyl ether (600 mL per 50 g of starting material L-BPB) was added to the crude product (S)-Ala-Ni-BPB and the slurry was then heated to 50-60° C. and maintained at this temperature for 1 h. The mixture was then filtered at 35° C. and washed with methyl tertiary-butyl ether (100 mL) to obtain the crystalline product XIa.

Alternate Recrystallization Procedure for XIa

Methyl tertiary-butyl ether (500 mL per 50 g of starting material L-BPB) was added to the crude product (S)-Ala-Ni-BPB and the slurry was then heated to 45-50° C. and maintained at this temperature for 1 h. The mixture was then filtered at 35° C. and washed with methyl tertiary-butyl ether (100 mL) to obtain the crystalline product XIa.

Alternate Recrystallization Procedure-III

Methyl tertiary-butyl ether (2000 mL per 280 g of starting material L-BPB) was added to the crude product (S)-Ala-Ni-BPB and the slurry was then heated to 45-50° C. and maintained at this temperature for 30 min. The mixture was then cooled to 20° C. and mixed at this temperature for 8 h. The resulting solid was then filtered and washed with methyl tertiary-butyl ether (100 mL).

(S)-Ala-Ni-BPB (300 g) was recrystallized by dissolving in THF (450 mL). The mixture was heated to 50° C. for 1 h followed by the addition of methyl tertiary-butyl ether (1500 mL) at 50° C. The resulting mixture was mixed at this temperature for additional 1 h. The slurry was then cooled to 20° C. and mixed at 20° C. for 1 h. The resulting solid was then filtered and washed with methyl tertiary-butyl ether (300 mL) to obtain the crystalline product XIa.

Example 2e

Preparation of S5-Ni-BPB

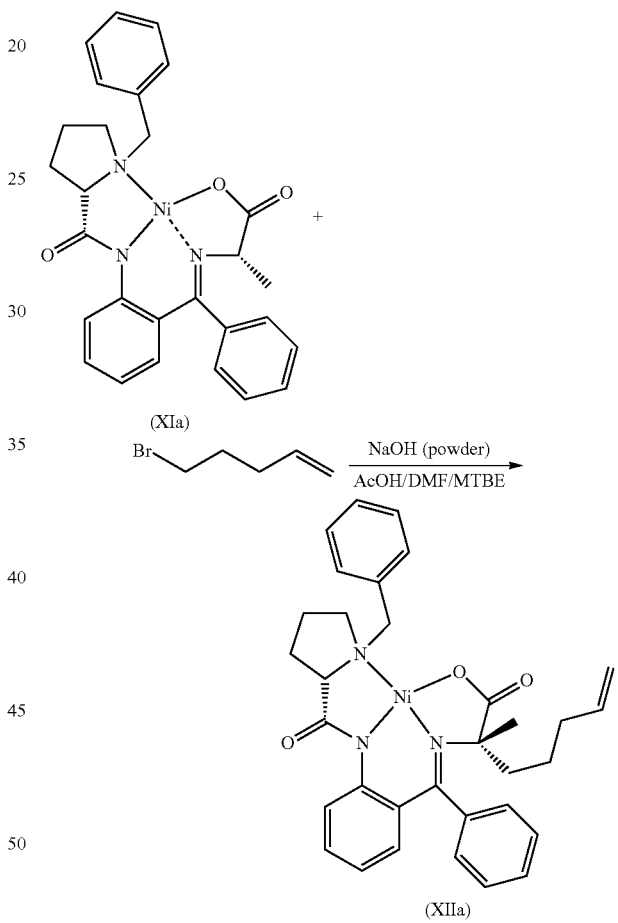

5.8 kg (1.0 equivs.) of (S)-Ala-Ni-BPB (XIa) was charged to a reactor and dissolved up into dimethylformamide and cooled to 10° C. 1.2 kg (2.5 equivs.) of sodium hydroxide (powder) was then charged to the same reactor and the mixture was sparged with nitrogen and agitated until a solution formed at 10° C. 3.3 kg (2.0 equivs.) of 5-bromo-1-pentene was then charged to the reactor maintaining the internal temperature of <20° C. The mixture was then allowed to agitate at 20-25° C. until the reaction was complete. Once the reaction was complete, the solution was cooled to 10° C. and 0.4 kg (1.5 equivs.) of acetic acid was charged maintaining an internal temperature of <25° C. Water was then charged, followed by methyl tert-butyl ether, and the organic layer was washed. The organic layer was then washed 2 more times with water and then concentrated. The product (XIIa) was crystallized out of isopropyl acetate, isolated and dried under heat and vacuum. Yield: 2.2 kg, 32.4%.

Recrystallization Procedure

Isopropyl acetate (200 mL per 12.5 g of starting material XIa) was added to the crude product S5-Ni-BPB and the mixture was mixed at 20° C. for 30 min then hexanes (500 mL) were added. The mixture was further mixed for 30 min following which it was filtered to obtain the crystalline product XIIa.

Alternate Recrystallization Procedure-I

Isopropyl acetate (80 mL per 39 g of starting material XIa) was added to the crude product S5-Ni-BPB and the mixture was mixed at 20° C. for 2 h. The mixture was filtered and washed with isopropyl acetate (35 mL). The filtrate and the washed were combined and heptanes (170 mL) were added. The resulting slurry was mixed for 1 h, then filtered and washed with heptanes (360 mL) to obtain the crystalline product XIIa.

Alternate Recrystallization Procedure-II

Isopropyl acetate (1000 mL per 205 g of starting material XIa) was added to the crude product S5-Ni-BPB and the mixture was dissolved at 70-80° C. The solution was cooled to 20° C. and the mixture was mixed at this temperature for 1 h during which no crystallization was observed. The mixture was filtered over celite and the solvent was removed under vacuum at 40° C. Methyl tertiary-butyl ether (1000 mL) was added and the mixture was heated to 60° C. then cooled to 20° C. and mixed for 24 h. The solid was filtered and washed with methyl tertiary-butyl ether (300 mL) and to obtain the crystalline product XIIa.

Alternate Recrystallization Procedure-III

Ethyl acetate (100 mL per 12.5 g of starting material XIa) was added to the crude product S5-Ni-BPB and the mixture was mixed at 20° C. for 30 min. hexanes (500 mL) were added and the resulting slurry was mixed for further 30 min after which it was filtered to obtain the crystalline product XIIa.

Alternate Recrystallization Procedure-IV

Methyl tertiary-butyl ether (100 mL per 12.5 g of starting material XIa) was added to the crude product S5-Ni-BPB and the mixture was heated to 45-50° C. Heptanes (400 mL) were added 45-50° C. The resulting slurry was cooled to 20° C. and filtered to obtain the crystalline product XIIa.

Example 2f

Preparation of (S)-2-Amino-2-methyl-hept-6-enoic acid

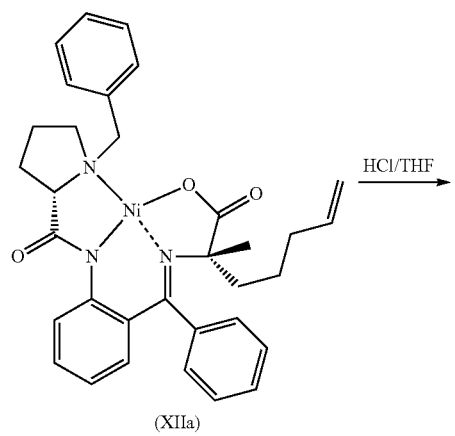

(XIIa)

HCl/THF

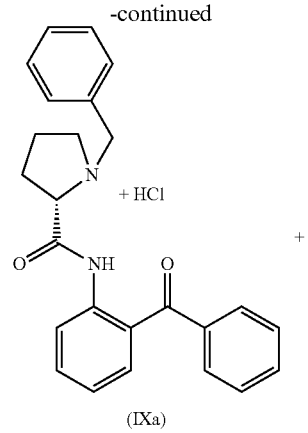

(IXa)

+

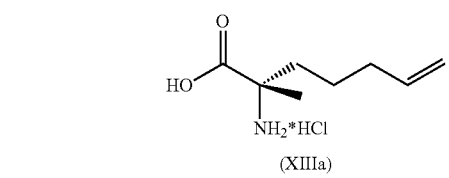

(XIIIa)

2.2 kg (1.0 equivs.) of S5-Ni-BPB (XIIa) was charged to a 15-L chem-glassreactor. Tetrahydrofuran was added and the mixture agitated at 20-25° C. until a solution formed. 1.8 kg (4.5 equvs.) of 32% hydrochloric acid was charged slowly while maintaining an internal temperature of <30° C. The mixture was then allowed to agitate for 6-8 hours at ambient temperature. The mixture was concentrated to remove tetrahydrofuran to yield a slurry. Additional water was added and the slurry was agitated at ambient temperature for 1-2 hours. The solid BPB salts were isolated by filtration and rinsed with additional water followed by methyl tert-butyl ether. The product filtrates were then re-charged to the reactor yielding a tri-phased solution. The lower-most layer was split from the upper two layers. The combined two organic layers were then washed 3× with water and concentrated to an oil. Acetonitrile was added and the mixture was warmed to 70° C. for 30 minutes. The mixture was then cooled to 25-30° C. and the solid product was isolated. The solid filter-cake was washed with acetonitrile and methyl tert-butyl ether, then analyzed for chemical purity. The product was then re-slurried out of additional acetonitrile and washed with acetonitrile and methyl tert-butyl ether. The material (XIIIa) was isolated and dried under heat and vacuum. Yield: 0.585 kg, 80.0%

Recrystallization Procedure for XIIIa

Acetonitrile (100 mL per 20 g of starting material S5-Ni-BPB (XIIa)) was added to the crude product and the mixture was mixed at 20° C. for 1 h. The mixture was then filtered and washed with acetonitrile (40 mL) to obtain the crystalline product XIIIa.

Alternate Recrystallization Procedure for XIIIa-I

Acetonitrile (500 mL per 185 g of starting material XIIa) was added to the crude product S5-Ni-BPB and the slurry was dissolved at 45-50° C. The solvent was removed under vacuum at 45-50° C., 500 mL acetonitrile was added and the resulting mixture was heated to 45-50° C. The mixture was then cooled to 35° C., filtered and washed with acetonitrile (50 mL) to obtain the crystalline product XIIIa.

Alternate Recrystallization Procedure for XIIIa

Acetonitrile (270 mL per 35 g of starting material XIIa) was added and the slurry was heated to 45-50° C.

The mixture was then cooled to 20° C. and mixed at this temperature for 2 h. The mixture was then filtered and washed with acetonitrile (50 mL) and methyl tertiary-butyl ether (50 mL) to obtain the crystalline product XIIIa.

Alternate Recrystallization Procedure for XIIIa

Isopropyl acetate (60 mL per 15 g of XIIIa) was added and the mixture was heated to 70° C. Acetonitrile (180 mL) was added and the resulting mixture was cooled to 20° C. The mixture was filtered and the resulting solid was washed with acetonitrile (50 mL) to obtain the crystalline product XIIIa.

Example 2g

Preparation of
N-Fmoc-(S)-α-methyl-α-aminohept-6-enoic acid

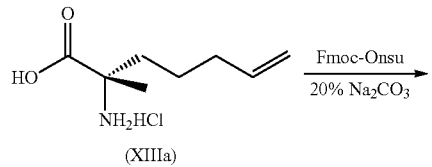

(XIIIa)

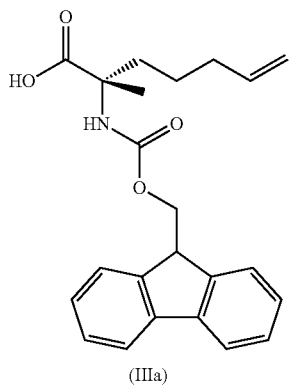

(IIIa)

0.585 kg (1.0 equiv.) of 2-amino-2-methyl-hept-6-enoic acid.HCl (XIIIa) was suspended in water and polished filtered to remove trace amounts of L-BPB.HCl from the solution. Methyl tert-butyl ether was added and the aqueous product layer extracted once with methyl tert-butyl ether. The aqueous product layer was re-charged and tetrahydrofuran was added. An aqueous 20% sodium carbonate solution (2.75 equiv.) was charged to the mixture, followed by Fmoc-Onsu (0.95 equiv.). The mixture was allowed to react at 20-25° C., while maintaining the pH between 8.5-9.0 with additional amounts of the 20% sodium carbonate solution until the reaction was complete. The mixture was pH adjusted down to pH 2.0-2.5 with conc. hydrochloric acid. Tetrahydrofuran was distilled off and methyl tert-butyl ether is charged. The layers were separated and the organic layer was washed 3 more times with additional water. The organic layer was then concentrated under vacuum and co-stripped with methyl tert-butyl ether. The organic product layer was concentrated and co-stripped with hexanes to a loose oil. The product (IIIa) was then crystallized out of chloroform and hexanes and dried at <0° C. under a 1.0 cfm nitrogen sweep.

Yield: 0.831 kg, 76.0%.

Recrystallization Procedure for IIa

Chloroform (30 mL per 9 g of starting material XIIIa) was added to the crude product. Hexanes (100 mL) were added and the mixture was cooled to 0° C. The resulting solid was filtered at 0° C. and washed with cold hexanes to obtain the crystalline product IIIa.

Recrystallization Procedure for Cyclohexylamine Salt of IIIa

Acetonitrile (300 mL per 19.04 g of starting material XIIIa) was added to the crude product and the pH was adjusted to 8-9 using cyclohexylamine at 20° C. The resulting mixture was mixed at 20° C. for 2 h and then filtered and washed with acetonitrile (50 mL) to obtain the crystalline cyclohexylamine salt of IIIa.

Alternate recrystallization procedure for cyclohexylamine salt of IIIa-I

Methyl tertiary-butyl ether (200 mL per 5 g of starting material XIIIa) was added to the crude product and the pH was adjusted to 8-9 using cyclohexylamine at 20° C. The resulting mixture was mixed at 20° C. for 1 h and then filtered and washed with methyl tertiary-butyl ether (50 mL) to obtain the crystalline cyclohexylamine salt of IIIa.

What is claimed is:
1. A crystalline salt of a compound of Formula (I):

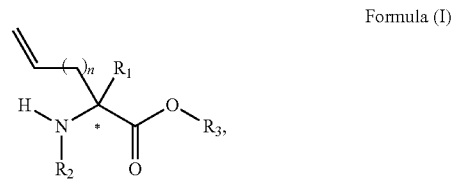

Formula (I)

wherein:
$R_1$ is $C_1$-$C_3$ alkyl, $C_1$-$C_3$ deuteroalkyl, or $C_1$-$C_3$ haloalkyl;
\* is a stereocenter;
n is an integer from 3 to 11;
$R_2$ is 9-Fluorenylmethoxycarbonyl (Fmoc); and
$R_3$ is —H; and wherein the salt is a cyclic amine salt.

2. The crystalline salt of claim 1, wherein $R_1$ is $C_1$-$C_3$ alkyl.

3. The crystalline salt of claim 1, wherein $R_1$ is methyl.

4. The crystalline salt of claim 1, wherein n is selected from the group consisting of: 3 and 6.

5. The crystalline salt of any one of claims 1-3 and 4, wherein the stereocenter \* is (S).

6. The crystalline salt of any one of claims 1-3 and 4, wherein the stereocenter \* is (R).

7. The crystalline salt of claim 1, having a chemical purity ranging from about 90% to 100%.

8. The crystalline salt of claim 1, having an optical purity ranging from about 90% to 100%.

9. The crystalline salt of claim 1, having an optical purity ranging from about 95% to 100%.

10. The crystalline salt of claim 1, having an enantiomeric excess ranging from about 90% to 100%.

11. The crystalline salt of claim 1, having an enantiomeric excess ranging from about 95% to 100%.

12. The crystalline salt of claim 1, wherein the compound has a Formula (IIa):

(IIa)

13. The crystalline salt of claim 12, wherein the crystalline salt has an enantiomeric excess of about 95% to 100%.

14. The crystalline salt of claim 1, wherein the compound has a Formula (IIb):

(IIb)

15. The crystalline salt of claim 14, wherein the crystalline salt has an enantiomeric excess of about 95% to 100%.

16. The crystalline salt of claim 1, wherein the compound has a Formula (Ma):

(IIIa)

17. The crystalline salt of claim 16, wherein the compound or its crystalline salt has an enantiomeric excess of about 95% to 100%.

18. The crystalline salt of claim 1, wherein the compound has a Formula (IIIb):

(IIIb)

19. The crystalline salt of claim 18, wherein the crystalline salt has an enantiomeric excess of about 95% to 100%.

20. The crystalline salt of claim 1, wherein n is 3.

21. The crystalline salt of claim 1, wherein the cyclic amine is selected from a group consisting of cyclopropylamine, cyclobutylamine, cyclopentylamine, cyclohexylamine, cycloheptylamine, and cyclooctylamine.

22. The crystalline salt of claim 1, wherein the cyclic amine is cyclohexylamine.

23. A method of making a peptide, the method comprising reacting the crystalline salt of claim 1 with an amino acid building block in presence of a coupling agent, thereby forming a peptide bond.

24. The method of claim 23, wherein the peptide comprises an α-helix.

25. The method of claim 23, further comprising crosslinking a pair of terminal alkene side chains of at least two amino acids of the peptide.

26. The method of claim 25, wherein the crosslinking comprises a metal-catalyzed olefin metathesis reaction.

* * * * *